(12) United States Patent
Datla et al.

(10) Patent No.: US 8,704,042 B2
(45) Date of Patent: Apr. 22, 2014

(54) TOR-INTERACTING PROTEINS (TIPS) AND GENES THEREFOR

(75) Inventors: Raju Datla, Saskatchewan (CA); Maozhi Ren, Saskatchewan (CA); Shuqing Qiu, Saskatchewan (CA); Gopalan Selvaraj, Saskatchewan (CA)

(73) Assignee: National Research Council of Canada, Ottawa, Ontario ( * ) Notice: Subject to any disclaimer, the term of this patent is extended or adjusted under 35 U.S.C. 154(b) by 200 days.

(21) Appl. No.: 13/138,005

(22) PCT Filed: Dec. 22, 2009

(86) PCT No.: PCT/CA2009/001874
§ 371 (c)(1),
(2), (4) Date: Jun. 23, 2011

(87) PCT Pub. No.: WO2010/071995
PCT Pub. Date: Jul. 1, 2010

(65) Prior Publication Data
US 2011/0258738 A1    Oct. 20, 2011

Related U.S. Application Data

(63) Continuation-in-part of application No. PCT/CA2009/001211, filed on Sep. 1, 2009.

(60) Provisional application No. 61/193,809, filed on Dec. 24, 2008.

(51) Int. Cl.
*C12N 15/82* (2006.01)
*C12N 15/87* (2006.01)
*A01H 5/00* (2006.01)

(52) U.S. Cl.
USPC ............ 800/289; 800/290; 800/298; 435/468

(58) Field of Classification Search
USPC ........................................................ 800/289
See application file for complete search history.

(56) References Cited

U.S. PATENT DOCUMENTS

2006/0150283 A1*  7/2006  Alexandrov et al. ......... 800/288
2006/0183137 A1   8/2006  Harper et al.
2007/0214517 A1   9/2007  Alexandrov et al.

FOREIGN PATENT DOCUMENTS

EP       1033405      9/2000
WO       03/008440    1/2003

(Continued)

OTHER PUBLICATIONS

GenBank Accession No. EU708610 [online], [retrieved on Mar. 29, 2013], retrieved from the internet <http://www.ncbi.nlm.nih.gov/nuccore/EU708610>.*

(Continued)

*Primary Examiner* — Shubo (Joe) Zhou
*Assistant Examiner* — Rebecca Coobs
(74) *Attorney, Agent, or Firm* — Laura Catherine Eckenswiller

(57) ABSTRACT

Broad experimental tools that include biochemical molecular developmental global genomics and loss and gain of function transgenic approaches have been applied to address target of rapamycin (TOR) signaling pathway in plants especially using *Arabidopsis* model system and *Brassica napus* crop Towards this objective, putative TOR interacting proteins (TIPs) have been identified and functions of these implicated in diverse developmental and biochemical processes have been investigated Functional studies including over-expression and silencing of TIPs have shown a range of phenotypes that include nutrition-use-efficiency, altered plant architecture and stress resistance in transgenic *Arabidopsis* and *Brassica* lines Some of these phenotypes are relevant to important developmental pathways implicated in canola crop yield and performance.

10 Claims, 27 Drawing Sheets

Transgenic Arabidopsis and Brassica Napus plants with 35S::TIP2 showing efficient growth in low nitrogen and potassium media

(56) References Cited

FOREIGN PATENT DOCUMENTS

| WO | 2004035798 | | 4/2004 |
|---|---|---|---|
| WO | WO 2004/035798 | * | 4/2004 |
| WO | 2007/078280 | | 7/2007 |
| WO | 2009/077611 | | 6/2009 |

OTHER PUBLICATIONS

UniProtKB Accession No. B3GN40 [online], [retrieved on Mar. 29, 2013], retrieved from the internet <http://www.uniprot.org/uniprot/B3GN40>.*
Extended European Search Report dated May 16, 2012 on European application 09833980.7.
Anderson, Garrett H et al. The *Arabidopsis* AtRaptor genes are essential for post-embryonic plant growth. BMC Biology, Biomed Central, vol. 3, No. 1. Apr. 21, 2005.
De Prost, D et al. An *Arabidopsis* homolog of Raptor/KOG1 is essential for early embryo development. Biochemical and Biophysical Research Communications. vol. 326. No. 4, Jan. 28, 2005, pp. 844-850.
Mahfouz, MM. *Arabidopsis* Target of Rapamycin Interacts with Raptor, Which Regulates the Activity of 56 Kinase in Response to Osmotic Stress Signals. The Plant Cell Online. vol. 18. No. 2, Feb. 1, 2006, pp. 477-490.
De La Cruz et al. Functional Characterization of a Maize Ribosomal S6 Protein Kinase (ZmS6K). a Plant Ortholog of Metazoan p70 S6K+. Biochemistry. vol. 43. No. 2, Jan. 1, 2004, pp. 533-539.
Dinkova et al. Dissecting the TOR?S6K signal transduction pathway in maize seedlings: relevance on cell growth regulation. Physiologia Plantarum. vol. 130. No. 1, May 1, 2007, pp. 1-10.
UniProt Database accession No. B3GN40, Jul. 22, 2008.
UniProt Database accession No. Q9XF67, Nov. 1, 1999.
Geneseq Database accession No. AWK66675, Oct. 29, 2009.
UniProt Database accession No. Q9SIZ2, May 1, 2000.
Geneseq Database accession No. ARM93560, Aug. 7, 2008.
Geneseq Database accession No. ALJ94416, Dec. 28, 2007.
Tzeng et al. Overexpression of the Lily p70s6k Gene in *Arabidopsis* Affects Elongation of Flower Organs and Indicates TOR-Dependent Regulation of AP3. Plant and Cell Physiology. vol. 50. No. 9, Sep. 1, 2009, pp. 1695-1709.
Zhang J, Xiao1 Q, Li K, Chen M, Chang J, Luo L, Li Y, Liu Y, Shewry PR, He G. (2006) An optimal pooling strategy applied to high-throughput screening for rare marker-free transformants. Biotechnology Letters. 28(19):1537-1544.
Zheng XF, Florentino D, Chen J, Crabtree GR, Schreiber SL (1995) TOR kinase domains are required for two distinct functions, only one of which is inhibited by rapamycin. Cell. Jul. 14; 82(1):121-30.
GenBank Accession No. AAD37165, Sep. 1999.
GenBank Accession No. AAG43423, May 2002.
GenBank Accession No. AAL67045, Sep. 2002.
GenBank Accession No. AB014076, Sep. 2001.
GenBank Accession No. AY056336, Sep. 2002.
GenBank Accession No. NM103891, Aug. 2009.
SwissProt Accession No. P42644, Nov. 1, 1995.
SwissProt Accession No. Q8LDQ4, Dec. 6, 2005.
SwissProt Accession No. Q9M272, Oct. 1, 2000.
SwissProt Accession No. Q9SIY9, May 1, 2000.
SwissProt Accession No. Q9SIZ2, May 1, 2000.
SwissProt Accession No. Q9SXL2, May 1, 2000.
SwissProt Accession No. Q9XEF6, Nov. 1, 1999.
SwissProt Accession No. Q93YQ1, Dec. 1, 2001.
SwissProt Accession No. Q39030, Dec. 1, 2000.
SwissProt Accession No. Q41969, Jul. 15, 1998.
Alvarez JP, Pekker I, Goldshmidt A, Blum E, Amsellem Z, Eshed Y (2006) Endogenous and synthetic microRNAs stimulate simultaneous, efficient, and localized regulation of multiple targets in diverse species. Plant Cell. 8: 1134-51.
Andrade MA, Bork P (1995) Heat repeats in the Huntington's disease protein. Nat Genet. Oct.;11(2):115-6.
Barbet NC, Schneider U, Helliwell SB, Stansfield I, Tuite MF, Hall MN (1996) TOR controls translation initiation and early G1 progression in yeast. Mol Biol Cell. Jan.; 7(1):25-42.
Bechtold N, Ellis J, Pellefer G (1993) In planta *Agrobacterium*-mediated gene transfer by infiltration of adult *Arabidopsis thaliana* plants. C.R. Acad. Sci. Ser. III Sci. Vie, 316: 1194-1199.
Becker D, Brettschneider R, Lorz H. (1994) Fertile transgenic wheat from microprojectile bombardment of scutellar tissue. Plant J. 5: 299-307.
Bla'Zquez MA, Soowal L, Lee I, Weigel D (1997) Leafy expression and flower initiation in *Arabidopsis*. Development 124, 3835-3844.
Bosotti R, Isacchi A, Sonnhammer EL (2000) Fat: A novel domain in PIK-related kinases. Trends Biochem Sci. May; 25(5):225-7.
Clough S J., Bent A (1998) Floral dip: A simplified method for *Agrobacterium*-mediated transformation of *Arabidopsis thaliana*. Plant J. 16:735-743.
Datla RS, Hammerlindl JK, Panchuk B, Pelcher LE, Keller W (1992) Modified binary plant transformation vectors with the wild-type gene encoding NPTII. Gene. 122, 383-384.
Datla R, Anderson JW, Selvaraj G (1997) Plant promoters for transgene expression. Biotechnology Annual Review. 3: 269-296.
De Virgilio C, Loewith R (2006) Cell growth control: little eukaryotes make big contributions. Oncogene. 25: 6392-6415.
Deblock M, DeBrouwer D, Tenning P (1989) Transformation of *Brassica napus* and *Brassica oleracea* using *Agrobacterium tumefaciens* and the expression of the bar and neo genes in the transgenic plants. Plant Physiol. 91: 694-701.
Dellaporta SJ, Wood J, Hicks JB (1983) A plant DNA minipreparation: Version II. Plant Mol. Biol. Reporter. 1: 19-21.
Depicker A, Montagu MV (1997) Post-transcriptional gene silencing in plants. Curr Opin Cell Biol. 9: 373-82.
Deprost D, Yao L, Sormani R, Moreau M, Leterreux G, Nicolai M, Bedu M, Robaglia C, Meyer C (2007) The *Arabidopsis* TOR kinase links plant growth, yield, stress resistance and mRNA translation. EMBO Reports 8: 864-870.
Gangloff YG, Mueller M, Dann SG, Svoboda P, Sticker M, Spetz JF, Um SH, Brown EJ, Cereghini S, Thomas G, Kozma SC (2004) Disruption of the mouse mTOR gene leads to early postimplantation lethality and prohibits embryonic stem cell development. Mol Cell Biol. N.
Helliwell CA, Waterhouse PM (2005) Constructs and methods for hairpin RNA-mediated gene silencing in plants. Methods Enzymology 392: 24-35.
Henikoff S, Till BJ, Comai L (2004) Tilling. Traditional mutagenesis meets functional genomics. Plant Physiol. 135: 630-6.
Hirayama T, Ohto C, Mizoguchi T, Shinozaki K (1995) A gene encoding a phosphatidylinositol-specific phospholipase C is induced by dehydration and salt stress in *Arabidopsis thaliana*. Proc. Natl. Acad. Sci. USA. 92: 3903-3907.
Inoki K, Guan KL (2006). Complexity of the TOR signaling network. Trends Cell Biol. Apr. 2006;16(4):206-12. Epub Mar. 3.
Katavic Y, Haughn GW, Reed D, Martin M, Kunst L (1994) In planta transformation of *Arabidopsis thaliana*. Mol. Gen. Genet. 245: 363-370.
Kim YJ, Kim JE, Lee JH, Lee MH, Jung HW, Bahk YY, Hwang BK, Hwang I, Kim WT (2004) The Vr-PLC3 gene encodes a putative plasma membrane-localized phosphoinositide-specific phospholipase C whose expression is induced by abiotic stress in mung bean (*Vigna radiata* L.). FEBS Lett., 556: 127-136.
Kunz J, Schneider U, Howald I, Schmidt A, Hall MN (2000) Heat repeats mediate plasma membrane localization of Tor2p in yeast. J Biol Chem. Nov. 24;275(47):37011-20.
Li X, Song Y, Century K, Straight S, Ronald P, Dong X, Lassner M, Zhang Y (2001) A fast neutron deletion mutagenesis-based reverse genetics system for plants. Plant J. 27: 235-242.
Loewith R, Jacinto E, Wullschleger S, Lorberg A, Crespo JL, Bonenfant D, Oppliger W, Jenoe P, Hall MN (2002) Two TOR complexes, only one of which is rapamycin sensitive, have distinct roles in cell growth control. Mol Cell. Sep.; 10(3):457-68.
Mahfouz MM, Kim S, Delauney AJ, Verma DPS (2006) *Arabidopsis* Target of Rapamycin interacts with Raptor which regulates the activity of S6 kinase in response to osmotic stress. The Plant Cell. 18: 477-490.

(56) References Cited

OTHER PUBLICATIONS

Martin DE, Hall MN (2005) Current Opinion in Cell Biology. 17:158-166.

Menand B, Desnos T, Nussaume L, Berger F, Bouchez D, Meyer C, Robaglia C (2002) Expression and disruption of the *Arabidopsis* TOR (target of rapamycin) gene. PNAS. 99: 6422-6427.

Meyer P (1995) Understanding and controlling transgene expression. Trends in Biotechnology. 13: 332-337.

Moloney MM, Walker JM, Sharma KK (1989) High efficiency transformation of *Brassica napus* using *Agrobacterium* vectors. Plant Cell Rep. 8: 238-242.

Munnik T. (1999) Phosphatidic acid: an emerging plant lipid second messenger. Trends in Plant Sci. 6: 227-233.

Murakami M, Ichisaka T, Maeda M, Oshiro N, Hara K, Edenhofer F, Kiyama H, Yonezawa K, Yamanaka S (2004) mTOR is essential for growth and proliferation in early mouse embryos and embryonic stem cells. Mol Cell Biol. Aug.;24(15):6710-8.

Neddleman and Wunsch (1970) J. Mol. Biol. 48: 443.

Nehra NS, Chibbar RN, Leung N, Caswell K, Mallard C, Steinhauer L, Baga M, Kartha KK (1994) Self-fertile transgenic wheat plants regenerated from isolated scutellar tissues following microprojectile bombardment with two distinct gene constructs. Plant J. 5: 285-297.

Pearson and Lipman (1988) Proc. Natl. Acad. Sci. (U.S.A.). 85: 2444.

Potrykus L (1991) Gene transfer to plants: Assessment of publish approaches and results. Annu. Rev. Plant Physiol. Plant Mol. Biol. 42: 205-225.

Powers T, Walter P (1999) Regulation of ribosome biogenesis by the rapamycin-sensitive TOR-signaling pathway in *Saccharomyces cerevisiae*. Mol Biol Cell. Apr.;10(4):987-1000.

Rhodes CA, Pierce DA, Mettler IJ, Mascarenhas D, Detmer JJ (1988) Genetically transformed maize plants from protoplasts. Science. 240: 204-207.

Sanford JC, Klein TM, Wolf ED, Allen N (1987) Delivery of substances into cells and tissues using a particle bombardment process. J. Part. Sci. Technol. 5: 27-37.

Schwab R, Ossowski S, Riester M, Warthmann N, Weigel D (2006) Highly specific gene silencing by artificial microRNAs in *Arabidopsis*. Plant Cell.18: 1121-33.

Shimamoto K, Terada R, Izawa T, Fujimoto H (1989) Fertile transgenic rice plants regenerated from transformed protoplasts. Nature. 335: 274-276.

Smith and Waterman. (1981) Ad. App. Math. 2: 482.

Songstad DD, Somers DA, Griesbach RJ (1995) Advances in alternative DNA delivery techniques. Plant Cell, Tissue and Organ Culture. 40: 1-15.

Stam M, de Bruin R, van Blokland R, van der Hoorn RA, Mol JN, Kooter JM (2000) Distinct features of post-transcriptional gene silencing by antisense transgenes in single copy and inverted T-DNA repeat loci. Plant J. 21: 27-42.

Vasil IK (1994) Molecular improvement of cereals. Plant Mol. Biol. 5: 925-937.

Vergnolle C, Vaultier M-N, Taconnat L, Renou J-P, Kader J-C, Zachowski A, Ruelland E (2005) The Cold-Induced Early Activation of Phospholipase C and D Pathways Determines the Response of Two Distinct Clusters of Genes in *Arabidopsis* Cell Suspensions. Plant Physiol. 139: 1217-1233.

Walden R, Wingender R (1995) Gene-transfer and plant regeneration techniques. Trends in Biotechnology. 13: 324-331.

Weisman R, Choder M (2001) The fission yeast TOR homolog, tor1+, is required for the response to starvation and other stresses via a conserved serine. J Biol Chem. Mar. 9;276(10):7027-32. Epub Nov. 28, 2000.

Wullschleger S, Loewith R, Hall MN (2006) TOR signaling in growth and metabolism. Cell. Feb. 10;124(3):471-84.

Young K (1998) Yeast two-hybrid: so many interactions, (in) so little time. Biol Reprod. 58 (2): 302-11.

GenBank Accession No. EU708610—*Brassica rapa* serine/threonine-protein kinase ATPK19/ATPK2 mRNA complete cds, sequence submitted May 8, 2008 and published by at least Jun. 3, 2008.

EP Application 09833908.7, Office Action dated Jul. 2, 2013.

\* cited by examiner

Transgenic Arabidopsis and Brassica Napus plants with 35S::TIP2 showing efficient growth in low nitrogen and potassium media Engineering transgenes TIP15 increasing canola seed yield Km: kanamycin resistance gene for plants selection marker
Spec: Spectinomycin resistance gene for bacteria selection marker
P35S: cauliflower mosaic virus 35S promoter
Tocs: octopine synthase gene terminator
Pmas: mannopine synthase gene promoter
Tmas: mannopine synthase gene terminator

TOR-INTERACTING PROTEINS (TIPS) AND GENES THEREFOR

CROSS-REFERENCE TO RELATED APPLICATIONS

This application is a national entry of International Patent Application PCT/CA2009/001874 filed Dec. 22, 2009 and is a continuation-in-part of International Patent Application PCT/CA2009/001211 filed Sep. 1, 2009 and claims the benefit of United States Provisional Patent Application U.S. Ser. No. 61/193,809 filed Dec. 24, 2008, the entire contents of both all of which are herein incorporated by reference.

FIELD OF THE INVENTION

This invention relates generally to biotechnology and, more particularly to the modification of plant growth and development and the enhancement of crop performance through manipulation of TOR gene expression and TOR interacting protein (TIPs) gene expression.

BACKGROUND OF THE INVENTION

TOR (target of rapamycin) encodes a large Ser/Thr protein kinase which is structurally and functionally conserved in eukaryotic species from yeast to animals to plants. TOR is a catalytic subunit of a large protein complex and plays a central role in the regulation of cell growth, differentiation, proliferation, survival, protein synthesis and transcription by integrating signals from hormones, nutrients and the environment (De Virgilo 2006: Wullschleger 2006; Inoki 2006).

In yeast, TOR is encoded by two genes (TOR1 and TOR2), which have 80% overall amino acid similarity, and interacts with other regulatory proteins to form two distinct complexes, TOR complex 1 (TORC1) and TOR complex 2 (TORC2), respectively. TORC1 in yeast is inhibited by rapamycin and is responsive to nutrient and growth factor cues to regulate temporal cell growth and metabolism, while TORC2 is not inhibited by rapamycin and is implicated in the regulation of cytoskeleton and spatial aspects of cell growth such as cell polarity (De Virgilo 2006: Weissman 2001).

In contrast to yeast other eukaryotes possess only a single TOR gene but as in yeast, TOR exists in two distinct complexes: TORC1 and TORC2. In mammals and *C. elegans*. TORC1 is rapamycin sensitive, while TORC2 is insensitive. The *Arabidopsis* genome contains only one copy of TOR which is insensitive to rapamycin. It remains to be determined if there are two functional TOR complexes in plants analogous to other eukaryotes, (Loewth 2002: Wullschleger 2006)

The TOR protein possesses several different functional domains. The N-terminal 1200 residues consist of 20 HEAT repeats, which typically mediate protein-protein interactions. Following the HEAT repeat region is the focal adhesion target (FAT) domain which has been suggested to facilitate protein binding. The TOR protein further comprises the FRB domain, the binding site for the FKBP-rapamycin complex. The catalytic serine/threonine kinase domain, which contains a conserved lipid kinase motif, is adjacent to FATC domain, a putative scaffolding domain, which is located at the extreme carboxyl terminus. (Kunz 2000; Andrade 1995; Bosotti 2000: Zheng 1995).

TOR1 knockout yeast strains display small cell size, slow growth rate, and hypersensitivity to temperature and osmotic stress. In contrast, loss of TOR2 function arrests growth in the early G1 phase of the cell cycle. In mice, disruption of TOR causes lethality at embryonic day 5.5 (E5.5) and proliferation arrest in embryonic stem cells. The protein sequence of TOR from *Arabidopsis* shows 60% and 59% identity with TOR2 and TOR1 from yeast. Disruption of AtTOR leads to the premature arrest of endosperm and embryo development at a very early globular stage, (16-64 cells) (Barbet 1996; Gangloff 2004; Murakamie 2004; Menand 2002; Mahfouz 2006).

In yeast and mammals, inhibition of the TOR signaling pathway by nutrient starvation or rapamycin treatment leads to a rapid down regulation of 18S, 5.8S, 25S and 5S rRNA synthesis and subsequent transcription of the majority of the 130 ribosome protein genes. The rate of cell proliferation and growth directly depends on the rate of protein synthesis, and in turn, protein synthesis depends on ribosome biogenesis. Ribosome biogenesis requires coordination of the production of ribosome components, including 4 different rRNA molecules and 130 ribosome proteins. TOR is suggested be a central regulator for ribosome biogenesis through RNA polymerase I dependent modulation of 18S, 5.8S and 25S ribosomal RNA transcription (RNA polymerase II drives expression of ribosome proteins and RNA polymerase III controls 5SrRNA synthesis) (Warner 2001; Powers 1999).

Plant growth and development is highly dependent on environmental interactions that are pivotal for survival. Plants adjust growth and development in relation to nutrient availability, light intensity, water availability and additional environmental parameters. The mechanisms that are involved in the perception and transduction of these environmental cues are poorly understood (Mahfouz 2006: Deprost 2007).

There remains a need for methods of regulating plant growth and development.

SUMMARY OF THE INVENTION

Recently it has been appreciated that growth in plants is positively correlated with expression of the (TOR) gene and that TOR may be fundamentally involved in control of growth and development. The TOR signaling network comprises a complex nexus of regulatory proteins that when manipulated by silencing or over-expression lead to many different changes in plant growth and development.

The present invention relates to AtTOR nucleic acid molecules and proteins from *Arabidopsis thaliana* and BnTOR nucleic acid molecules and proteins from *Brassica napus* that are important controlling factors for the regulation of growth and development in plants.

The present invention further relates to 30 or more TOR-Interacting Proteins, (TIPs) that form part of a regulatory protein complex that affects many aspects of growth and development, and to nucleic acid molecules encoding the TIPs.

The present invention further relates to a method of regulating plant growth and development. More specifically the present invention relates to the expression of nucleic acid molecules of the present invention in recombinant plants to effect changes in plant growth and development.

Thus, there is provided a method of regulating growth and development in a plant comprising: introducing into the plant a nucleic acid molecule encoding a target of rapamycin (TOR)-interacting protein (TIP), a target of rapamycin (TOR) protein or a protein kinase domain of a target of rapamycin (TOR) protein, under conditions whereby the nucleic acid molecule is over-expressed thereby altering plant growth and development.

The present invention further relates to a method of increasing ribosome biogenesis by increasing ribosomal RNA and ribosomal protein synthesis in a plant cell comprising: introducing into the plant cell a nucleic acid molecule encoding a target of rapamycin (TOR) protein or a protein kinase domain of a TOR protein under conditions whereby the nucleic acid molecule is over-expressed thereby increasing ribosomal RNA expression and ribosome biogenesis in the plant cell.

The present invention further relates to decreasing ribosome biogenesis by decreasing ribosomal RNA expression and ribosome protein synthesis in a plant cell comprising: silencing a native nucleic acid molecule encoding a target of rapamycin (TOR) protein or a protein kinase domain of a TOR protein thereby decreasing ribosome biogenesis and ribosomal RNA expression in the plant cell.

The present invention further relates to a method of altering phenotype of a plant comprising over-expressing in the plant a nucleic acid molecule encoding a target of rapamycin (TOR) protein, a protein kinase domain of a TOR protein, or a TOR-interacting protein (TIP).

Phenotypic changes that may result from over-expression of a nucleic acid molecule encoding a TOR protein, a protein kinase domain of a TOR protein or a TOR-interacting protein (TIP) in a plant include, for example, increased cell number, increased leaf size, increased meristem size, increased stem size, increased nutrient-use-efficiency (e.g. nitrogen and/or potassium use efficiency), increased water-use-efficiency, increased seed size, increased seed number, increased flower number, earlier flowering, shorter or longer life span, increased branching, increased silique size, increased silique number, multiple siliques in one flower, increased gynoecium size, increased oil content or any combination thereof, compared to a wild-type plant grown under the same conditions.

In one embodiment, over-expression of a nucleic acid molecule encoding a target of rapamycin (TOR) protein or a protein kinase domain of a TOR protein in a plant results in a phenotypic change in the plant, for example, increased cell number, increased cell size, increased water-use-efficiency, increased seed size, increased seed number, earlier flowering or any combination thereof, compared to a wild-type plant grown under the same conditions.

In one embodiment, there is provided a method of modulating the flowering time of a plant comprising: introducing into cells of said plant a nucleic acid molecule encoding a target of rapamycin (TOR) protein or a protein kinase domain of a TOR protein under conditions whereby the nucleic acid molecule is over-expressed thereby modulating the flowering time of said plant. Preferably, the method reduces the time required for a plant to commence flowering and complete the life cycle (seed to seed).

In one embodiment, there is provided a method of increasing the size of seed produced by a plant said method comprising: introducing into cells of said plant a nucleic acid molecule encoding a target of rapamycin (TOR) protein or a protein kinase domain of a TOR protein under conditions whereby the nucleic acid molecule is over-expressed thereby increasing seed size of said plant.

In one embodiment, there is provided a method of increasing the drought (water stress) tolerance of a plant said method comprising: introducing into cells of said plant a nucleic acid molecule encoding a target of rapamycin (TOR) protein or a protein kinase domain of a TOR protein under conditions whereby the drought tolerance of said plant is increased.

There is also provided a method of regulating growth and development in a plant comprising silencing in the plant expression of a TOR protein, a protein kinase domain of a TOR protein or a protein that interacts with TOR. Regulation of growth and development can lead to altered phenotypes that are commercially useful.

There is also provided a use of a TOR protein or a protein kinase domain of a TOR protein for identifying proteins involved in developmental pathways in a plant associated with TOR. Thus, a method of identifying a TOR-interacting protein (TIP) involved in developmental pathways in a plant comprises: providing a test organism having a phenotypic deficiency arising from non-functioning of a transcription factor; introducing into the organism a protein construct comprising a TOR protein or a protein kinase domain of a TOR protein and a binding domain of the transcription factor; introducing into the organism a protein construct comprising a protein of interest and an activation domain of the transcription factor; and, determining whether the transcription factor functions thereby determining that the protein of interest is a TOR-interacting protein.

There is also provided an isolated or purified polypeptide comprising an amino acid sequence having at least 85% sequence identity to the amino acid sequence as set forth in SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34. SEQ ID NO: 36, SEQ ID NO: 38, SEQ ID NO: 40, SEQ ID NO: 42 or SEQ ID NO: 79, or a conservatively substituted amino acid sequence thereof.

There is also provided an isolated or purified nucleic acid molecule comprising a nucleotide sequence having at least 85% sequence identity to the nucleotide sequence as set forth in SEQ ID NO: 3. SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19. SEQ ID NO: 21, SEQ ID NO: 23. SEQ ID NO: 25, SEQ ID NO: 27, SEQ ID NO: 29, SEQ ID NO: 31, SEQ ID NO: 33, SEQ ID NO: 35. SEQ ID NO: 37, SEQ ID NO: 39, SEQ ID NO: 41 or SEQ ID NO: 78, or a codon degenerate nucleotide sequence thereof.

The present invention further relates to a plant cell, plant seed or plant having introduced therein a nucleic acid molecule encoding a target of rapamycin (TOR) protein, a protein kinase domain of a TOR protein, or a TOR-interacting protein (TIP), expression of the nucleic acid molecule altering growth and development of the cell, seed or plant in comparison to a cell, seed or plant in which the nucleic acid molecule is not introduced.

Particularly preferred plants for modification, either through over-expression or silencing, include *Arabidopsis thaliana, Brassica* spp. (e.g. *B. napus. B. oleracea, B. rapa, B. carinata, B. juncea*), *Borago* spp. (e.g. borage), *Ricinus* spp (e.g. castor (*Ricinus communis*)), *Theobroma* spp. (e.g. cocoa bean (*Theobroma cacao*)), *Zea* spp. (e.g. corn (*Zea mays*)), *Gossypium* spp. (e.g. cotton), *Crambe* spp., *Cuphea* spp., *Linum* spp. (e.g. flax), *Lesquerella* spp., *Limnanthes* spp., *Linola, Tropaeolum* spp. (e.g. nasturtium), *Oenothera* spp., *Olea* spp. (e.g. olive), *Elaeis* spp. (e.g. palm). *Arachis* spp. (e.g. peanut), *Carthamus* spp., (e.g. safflower), *Glycine* spp and *Soja* spp. (e.g. soybean), *Helianthus* spp. (e.g. sunflower), *Nicotiana* spp (e.g. tobacco), *Vemonia* spp., *Triticum* spp. (e.g. wheat), *Hordeum* spp. (e.g. barley), *Oryza* spp. (e.g. rice). *Avena* spp. (e.g. oat), *Sorghum* spp., *Secale* spp. (e.g. rye), *Medicago sativa* (alfalfa), *Lens culinaris* (lentils), and *Cicer arietinum* (chick pea). *Brassica* spp. are most preferred.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Figure 1:
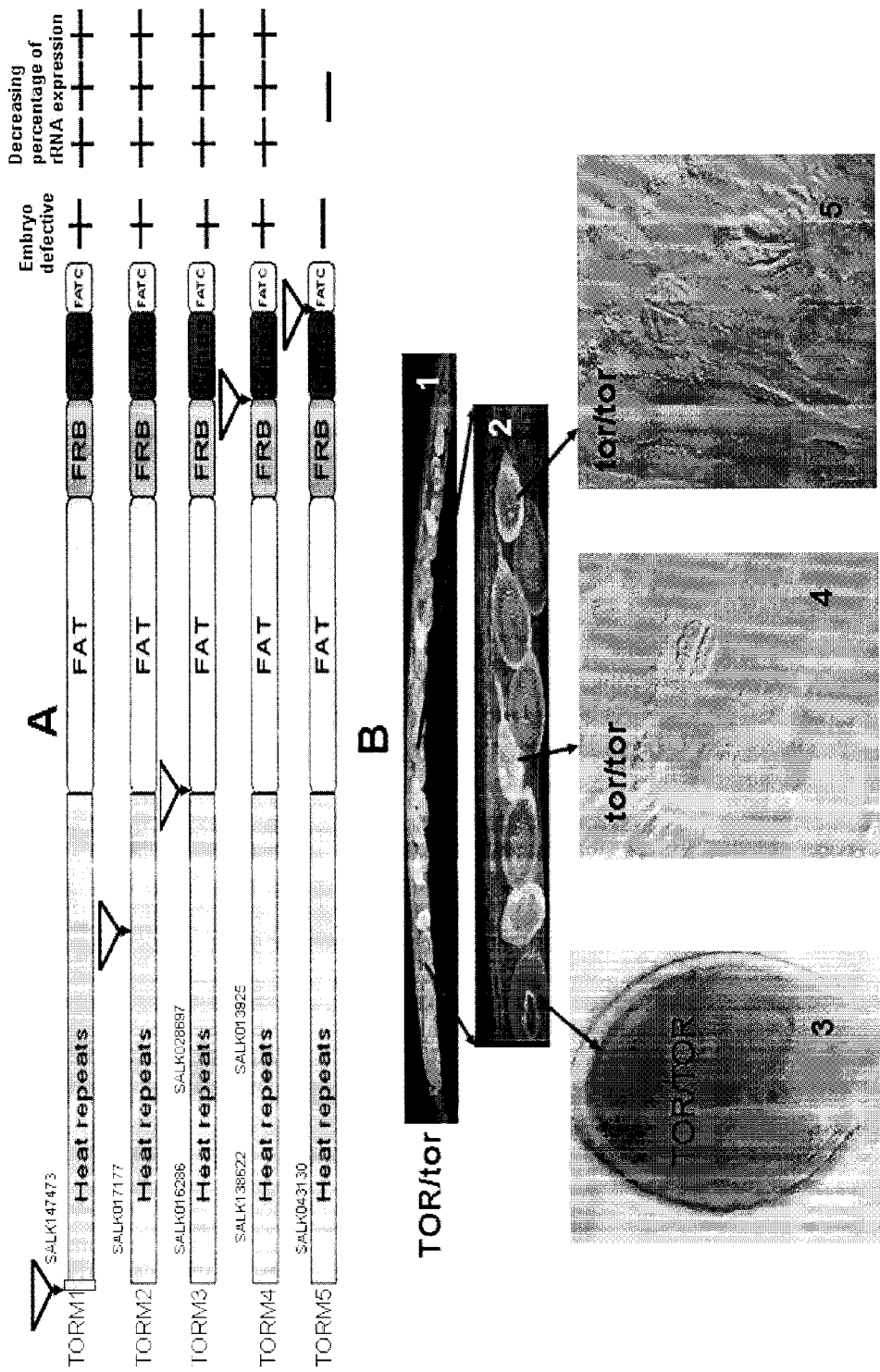
FIG. 1A depicts a series of insertion/knockout mutants from N to C terminal of TOR that were genotyped and phenotyped.
FIG. 1B depicts pictures showing that embryo development is blocked at 16-32 cells in AtTOR mutant lines. Embryo phenotype of AtTOR knockout line (1 and 2) and Nomarski optics images of TOR/TOR (3) and tor/tor (4 and 5) are shown. Pictures 3, 4 and 5 are shown at the same magnification, respectively.

Sequence Identity:

Two amino-acid or nucleotide sequences are said to be "identical" if the sequence of amino-acids or nucleotidic residues in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman (Smith 1981), by the homology alignment algorithm of Neddleman and Wunsch (Neddleman 1970), by the search for similarity method of Pearson and Lipman (Pearson 1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection. Isolated and/or purified sequences of the present invention may have a percentage identity with the bases of a nucleotide sequence, or the amino acids of a polypeptide sequence, of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%. This percentage is purely statistical, and it is possible to distribute the differences between the two nucleotide sequences at random and over the whole of their length.

It will be appreciated that this disclosure embraces the degeneracy of codon usage as would be understood by one of ordinary skill in the art and as illustrated in Table 1. Further-more, it will be understood by one skilled in the art that conservative substitutions may be made in the amino acid sequence of a polypeptide without disrupting the structure or function of the polypeptide. Conservative substitutions are accomplished by the skilled artisan by substituting amino acids with similar hydrophobicity, polarity, and R-chain length for one another. Additionally, by comparing aligned sequences of homologous proteins from different species, conservative substitutions may be identified by locating amino acid residues that have been mutated between species without altering the basic functions of the encoded proteins. Table 2 provides an exemplary list of conservative substitutions.

TABLE 1

Codon Degeneracies

| Amino Acid | Codons | Amino Acid | Codons |
|---|---|---|---|
| Ala/A | GCT, GCC, GCA, GCG | Lys/K | AAA, AAG |
| Arg/R | CGT, CGC, CGA, CGG, AGA, AGG | Met/M | ATG |
| Asn/N | AAT, AAC | Phe/F | TTT, TTC |
| Asp/D | GAT, GAC | Pro/P | CCT, CCC, CCA, CCG |
| Cys/C | TGT, UGC | Ser/S | TCT, TCC, TCA, TCG, AGT, AGC |
| Gln/Q | CAA, CAG | Thr/T | ACT, ACC, ACA, ACG |
| Glu/E | GAA, GAG | Trp/W | TGG |
| Gly/G | GGT, GGC, GGA, GGG | Tyr/Y | TAT, TAC |
| His/H | CAT, CAC | Val/V | GTT, GTC, GTA, GTG |
| Ile/I | ATT, ATC, ATA | START | ATG |
| Leu/L | TTA, TTG, CTT, CTC, CTA, CTG | STOP | TAG, TGA, TAA |

TABLE 2

Conservative Substitutions

| Type of Amino Acid | Substitutable Amino Acids |
|---|---|
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

The definition of sequence identity given above is the definition that would be used by one of skill in the art. The definition by itself does not need the help of any algorithm, said algorithms being helpful only to achieve the optimal alignments of sequences, rather than the calculation of sequence identity. From the definition given above, it follows that there is a well defined and only one value for the sequence identity between two compared sequences which value corresponds to the value obtained for the best or optimal alignment.

In the BLAST N or BLAST P "BLAST 2 sequence", software which is habitually used by the inventors and in general by the skilled man for comparing and determining the identity between two sequences, gap cost which depends on the sequence length to be compared is directly selected by the software (i.e. 11.2 for substitution matrix BLOSUM-62 for length>85).

Over-Expression:

DNA isolation and cloning is well established. Similarly, an isolated gene may be inserted into a vector and transformed into plant cells by conventional techniques. Nucleic acid molecules may be transformed into a plant. As known in the art, there are a number of ways by which genes and gene constructs can be introduced into plants and a combination of transformation and tissue culture techniques have been successfully integrated into effective strategies for creating transgenic plants. These methods, which can be used in the invention, have been described elsewhere (Potrykus 1991; Vasil 1994; Walden 1995; Songstad 1995), and are well known to persons skilled in the art. For example, one skilled in the art will certainly be aware that, in addition to *Agrobacterium* mediated transformation of *Arabidopsis* by vacuum infiltration (Bechtold 1993) or wound inoculation (Katavic 1994), it is equally possible to transform other plant species, using *Agrobacterium* Ti-plasmid mediated transformation (e.g., hypocotyl (DeBlock 1989) or cotyledonary petiole (Moloney 1989) wound infection), particle bombardment/biolistic methods (Sanford 1987; Nehra 1994; Becker 1994) or polyethylene glycol-assisted, protoplast transformation (Rhodes 1988; Shimamoto 1989) methods.

As will also be apparent to persons skilled in the art, and as described elsewhere (Meyer 1995; Datla 1997), it is possible to utilize plant promoters to direct any intended regulation of transgene expression using constitutive promoters (e.g., those based on CaMV35S), or by using promoters which can target gene expression to particular cells, tissues (e.g., napin promoter for expression of transgenes in developing seed cotyledons), organs (e.g., roots), to a particular developmental stage, or in response to a particular external stimulus (e.g., heat shock). Promoters for use herein may be inducible, constitutive, or tissue-specific or cell specific or have various combinations of such characteristics. Useful promoters include, but are not limited to constitutive promoters such as carnation etched ring virus (CERV), cauliflower mosaic virus (CaMV) 35S promoter, or more particularly the double enhanced cauliflower mosaic virus promoter, comprising two CaMV 35S promoters in tandem (referred to as a "Double 35S" promoter). Meristem specific promoters include, for example, STM. BP, WUS, CLV gene promoters. Seed specific promoters include, for example, the napin promoter. Other cell and tissue specific promoters are well known in the art.

Promoter and termination regulatory regions that will be functional in the host plant cell may be heterologous (that is, not naturally occurring) or homologous (derived from the plant host species) to the plant cell and the gene. Suitable promoters which may be used are described above. The termination regulatory region may be derived from the 3' region of the gene from which the promoter was obtained or from another gene. Suitable termination regions which may be used are well known in the art and include *Agrobacterium tumefaciens* nopaline synthase terminator (Tnos), *A. tumefaciens* mannopine synthase terminator (Tmas) and the CaMV 35S terminator (T35S). Particularly preferred termination regions for use herein include the pea ribulose bisphosphate carboxylase small subunit termination region (TrbcS) or the Tnos termination region. Such gene constructs may suitably be screened for activity by transformation into a host plant via *Agrobacterium* and screening for the desired activity using known techniques.

Preferably, a nucleic acid molecule construct for use herein is comprised within a vector, most suitably an expression vector adapted for expression in an appropriate plant cell. It will be appreciated that any vector which is capable of producing a plant comprising the introduced nucleic acid sequence will be sufficient. Suitable vectors are well known to those skilled in the art and are described in general technical references (Pouwels 1986). Particularly suitable vectors include the Ti plasmid vectors.

Transformation techniques for introducing the DNA constructs into host cells are well known in the art and include such methods as micro-injection, using polyethylene glycol, electroporation, or high velocity ballistic penetration. A preferred method relies on *Agrobacterium*-mediated transformation. After transformation of the plant cells or plant, those plant cells or plants into which the desired nucleic acid molecule has been incorporated may be selected by such methods as antibiotic resistance, herbicide resistance, tolerance to amino-acid analogues or using phenotypic markers. Various assays may be used to determine whether the plant cell shows an increase in gene expression, for example. Northern blotting or quantitative reverse transcriptase PCR (RT-PCR). Whole transgenic plants may be regenerated from the transformed cell by conventional methods.

Various assays may be used to determine whether the plant cell shows an increase in gene expression, for example, Northern blotting or quantitative reverse transcriptase PCR (qRT-PCR). Whole transgenic plants may be regenerated from the transformed cell by conventional methods. Such plants produce seeds containing the genes for the introduced trait and can be grown to produce plants that will produce the selected phenotype.

Silencing:

Silencing may be accomplished in a number of ways generally known in the art, for example. RNA interference (RNAi) techniques, artificial microRNA techniques, virus-induced gene silencing (VIGS) techniques, antisense techniques, sense co-suppression techniques and targeted mutagenesis techniques.

RNAi techniques involve stable transformation using RNA interference (RNAi) plasmid constructs (Helliwell 2005). Such plasmids are composed of a fragment of the target gene to be silenced in an inverted repeat structure. The inverted repeats are separated by a spacer, often an intron. The RNAi construct driven by a suitable promoter, for example, the Cauliflower mosaic virus (CaMV) 35S promoter, is integrated into the plant genome and subsequent transcription of the transgene leads to an RNA molecule that folds back on itself to form a double-stranded hairpin RNA. This double-stranded RNA structure is recognized by the plant and cut into small RNAs (about 21 nucleotides long) called small interfering RNAs (siRNAs). siRNAs associate with a protein complex (RISC) which goes on to direct degradation of the mRNA for the target gene.

Artificial microRNA (amiRNA) techniques exploit the microRNA (miRNA) pathway that functions to silence endogenous genes in plants and other eukaryotes (Schwab 2006; Alvarez 2006). In this method, 21 nucleotide long fragments of the gene to be silenced are introduced into a pre-miRNA gene to form a pre-amiRNA construct. The pre-miRNA construct is transferred into the plant genome using transformation methods apparent to one skilled in the art. After transcription of the pre-amiRNA, processing yields amiRNAs that target genes which share nucleotide identity with the 21 nucleotide amiRNA sequence.

In RNAi silencing techniques, two factors can influence the choice of length of the fragment. The shorter the fragment the less frequently effective silencing will be achieved, but very long hairpins increase the chance of recombination in bacterial host strains. The effectiveness of silencing also appears to be gene dependent and could reflect accessibility of target mRNA or the relative abundances of the target mRNA and the hpRNA in cells in which the gene is active. A fragment length of between 100 and 800 bp, preferably between 300 and 600 bp, is generally suitable to maximize the efficiency of silencing obtained. The other consideration is the part of the gene to be targeted. 5' UTR, coding region, and 3' UTR fragments can be used with equally good results. As the mechanism of silencing depends on sequence homology there is potential for cross-silencing of related mRNA sequences. Where this is not desirable a region with low sequence similarity to other sequences, such as a 5' or 3' UTR, should be chosen. The rule for avoiding cross-homology silencing appears to be to use sequences that do not have blocks of sequence identity of over 20 bases between the construct and the non-target gene sequences. Many of these same principles apply to selection of target regions for designing amiRNAs.

Virus-induced gene silencing (VIGS) techniques are a variation of RNAi techniques that exploits the endogenous antiviral defenses of plants. Infection of plants with recombinant VIGS viruses containing fragments of host DNA leads to post-transcriptional gene silencing for the target gene. In one embodiment, a tobacco rattle virus (TRV) based VIGS system can be used.

Antisense techniques involve introducing into a plant an antisense oligonucleotide that will bind to the messenger RNA (mRNA) produced by the gene of interest. The "antisense" oligonucleotide has a base sequence complementary to the gene's messenger RNA (mRNA), which is called the "sense" sequence. Activity of the sense segment of the mRNA is blocked by the anti-sense mRNA segment, thereby effectively inactivating gene expression. Application of antisense to gene silencing in plants is described in more detail by Stam 2000.

Sense co-suppression techniques involve introducing a highly expressed sense transgene into a plant resulting in reduced expression of both the transgene and the endogenous gene (Depicker 1997). The effect depends on sequence identity between transgene and endogenous gene.

Targeted mutagenesis techniques, for example TILLING (Targeting Induced Local Lesions IN Genomes) and "delete-a-gene" using fast-neutron bombardment, may be used to knockout gene function in a plant (Henikoff 2004; Li 2001). TILLING involves treating seeds or individual cells with a mutagen to cause point mutations that are then discovered in genes of interest using a sensitive method for single-nucleotide mutation detection. Detection of desired mutations (e.g. mutations resulting in the inactivation of the gene product of interest) may be accomplished, for example, by PCR methods. For example, oligonucleotide primers derived from the gene of interest may be prepared and PCR may be used to amplify regions of the gene of interest from plants in the mutagenized population. Amplified mutant genes may be annealed to wild-type genes to find mismatches between the mutant genes and wild-type genes. Detected differences may be traced back to the plants which had the mutant gene thereby revealing which mutagenized plants will have the desired expression (e.g. silencing of the gene of interest) These plants may then be selectively bred to produce a population having the desired expression. TILLING can provide an allelic series that includes missense and knockout mutations, which exhibit reduced expression of the targeted gene. TILLING is touted as a possible approach to gene knockout that does not involve introduction of transgenes, and therefore may be more acceptable to consumers. Fast-neutron bombardment induces mutations, i.e. deletions, in plant genomes that can also be detected using PCR in a manner similar to TILLING.

Silencing of the nucleic acid molecule encoding a target of rapamycin (TOR) protein or a protein kinase domain of a TOR protein in a plant results in an embryo defective phenotype, increasing the likelihood of embryo fatality or severe developmental deficiencies in the plant. In view of the fundamental importance of TOR gene expression constitutive expression of a TOR gene silencing construct is less desirable than selective cell and tissue specific expression of TOR silencing sequences. Thus, silencing of TOR, a protein kinase domain of TOR or a TIP in a selective cell or tissue specific manner can lead to a variety of useful phenotypes arising from such genetic ablation, for example, male sterility or female sterility. Cell or tissue specific promoters, for example napin seed specific promoter or meristem specific promoters of STM, BP, WUS, CLV genes can aid in targeting silencing to specific cells or tissues. Other cell and tissue specific promoters are well known in the art.

Screening for TOR-Interacting Proteins (TIPs):

Screening for TOR-interacting proteins (TIPs) using the TOR protein or the kinase domain of the TOR protein can be accomplished by any suitable method. For example, two-hybrid screening is one technique used to identify protein-protein interactions [Young 1998]. The two-hybrid screen utilizes the fact that, in most eukaryotic transcription factors, the activating and binding domains are modular and can function in close proximity to each other without direct binding. Thus, even though the transcription factor is split into two fragments, it can still activate transcription when the two fragments are indirectly connected.

In the yeast two-hybrid assay system (one variation of the two-hybrid screen), a yeast strain deficient in a transcription factor and therefore deficient in the biosynthesis of certain nutrients is utilized. This yeast strain can be transformed simultaneously with two separate plasmids, a first plasmid engineered to produce a protein product in which the DNA-binding domain (BD) fragment of the deficient transcription factor is fused onto the TOR protein of kinase domain of the TOR protein, while a second plasmid is engineered to produce a protein product in which the activation domain (AD) fragment of the deficient transcription factor is fused onto a putative TIPs. If the TOR and putative TIPs proteins interact (i.e. bind), then the AD and BD of the transcription factor are indirectly connected, bringing the AD in proximity to the transcription start site and transcription of a reporter gene can occur. If the TOR and putative TIPs proteins do not interact, there is no transcription of the reporter gene. In this way, a successful interaction between the fused protein is linked to a change in the cell phenotype.

Example 1

Plant Growth Methods

Arabidopsis plants were grown in growth chamber with temperature set at 22° C. with 16 h light/8 h dark cycle. The Arabidopsis ecotype Columbia (Col) was used in all transformation and comparative analysis. All the Arabidopsis growth and screening of primary transformants were performed according to the methods described in Zhang et al. (Zhang 2006). Brassica napus plants were grown in growth chamber using 16 h photoperiod with 20° C. day/15° C. night cycle settings. The Brassica napus DH12075 line was used in the transformation and comparative analysis.

Example 2

AtTOR

Isolation of DNA, Purification of Total RNA and cDNA Synthesis

Genomic DNA and Total RNA was isolated from 1-week-old Arabidopsis thaliana seedlings (ecotype Columbia) using DNeasy Plant Mini Kit (Cat. No. 69104) and RNeasy Plant Mini Kit (QIAGEN, Cat. No. 74904) following the manufacturer's instructions. A SMART RACE cDNA amplification kit (Clontech, cat. No. 634914) was used for cDNA amplification following the manufacturer's instructions.

The full-length cDNAs of the wild type TOR and various truncated fragments thereof were amplified by RT-PCR using the Advantage® 2 Polymerase Mix kit (Clontech, Cat. No. 639201) following the manufacturer's instructions. Three overlapping fragments were amplified and fused together by using the restriction enzymes (BspEI and BlpI) to generate the full-length clone. The sequences were verified by DNA sequencing.

AtTOR is a single copy gene in Arabidopsis that encodes a 279 KD protein with Ser/Thr kinase activity. Full length (7446 bp) cDNA clones of corresponding AtTOR and its homolog in B. napus were isolated. The predicted TOR protein (2481 aa. SEQ ID NO: 2) contains conserved HEAT repeats, FAT, FRB, kinase and FATC domains.

Generation of p8GWG (attL1/AsisI/TOR::GUS/AscI/attL2) and GUS Histochemical Analysis 1.8 kb β-glucuronidase (GUS) marker gene was PCR amplified using forward primer GUSF and reverse primer GUSR (see Table 3) inserted into pCR8/GW/TOPO using the TA cloning kit (Invitrogen, Cat. K2500-20).

TABLE 3

Primers

| Primer name | SEQ ID | Primer sequence | RE sites |
|---|---|---|---|
| TORF1F | 43 | 5'-GCGGCCGATGTCTACCTCGTCGCAATC-3' | Not I |
| TORF1R | 44 | 5'-CCCGGGTGAGGATCCAAAGCGCCCATAAT-3' | Xma I |
| TORF2F | 45 | 5'-GCGGCCGCGCCATCTTATACAGTTGTTGACCTA-3' | Not I |
| TORF2R | 46 | 5'-CCCGGGCACATATTCGGCCATTTGATCCCACTCTCC-3' | Xma I |
| TORF3F | 47 | 5'-GCGGCCGCAAAGAGTACTGGAGTCCTGCTGAG-3' | Not I |

TABLE 3-continued

Primers

| Primer name | SEQ ID | Primer sequence | RE sites |
|---|---|---|---|
| TORF3R | 48 | 5'-CCCGGGCCAGAAAGGGCACCACCCAACATAG-3' | Xma I |
| TORF4F | 49 | 5'-GCGGCCGCATGAGTCATGTCAACATTAACACATG-3' | Not I |
| TORF5F | 50 | 5'-GCGGCCGCATGTTGGAATCTGTTTCTCCTGAGTTG-3' | Not I |
| TORF6R | 51 | 5'-CCCGGGCTCATTTAAAACTTCATTAGCATC-3' | Xma I |
| TORF8F | 52 | 5'-GCGGCCGCATGTTTGGCTCGAGCAGGTCAACAC-3' | Not I |
| TORR8R | 53 | 5'-CCCGGGGGCCATTTCCAAGCTCCTAACTA-3' | Xma I |
| TORF9F | 54 | 5'-GCGGCCGCATGGATGCCAACCCAGTTGCTG-3' | Not I |
| TORR9R | 55 | 5'-CCCGGGAACCACCTCTTGAGCCGCAGC-3' | Xma I |
| TORF10F | 56 | 5'-GCGGCCGCATGTCGCATTACATTTCAAGAGG-3' | Not I |
| TORR10R | 57 | 5'-CCCGGGACGGGGCATCTGCACGATATG-3' | Xma I |
| PTORF | 58 | 5'-GCGATCGCAAGACGACGATGATGACGACGGTGAT-3' | Asis I |
| PTORR | 59 | 5'-GCGGCCGCCGCTGCAGGGCCAGTCCAGCCAC-3' | Not I |
| GUSF | 60 | 5'-GCGATCGCAAAGCGGCCGCATGTTACGTCCTGTAGAAAC-3' | Asis I, Not I |
| GUSR | 61 | 5'-GGCGCGCCTCATTGTTTGCCTCCCTGCTG-3' | Asc I |
| VGFPF | 62 | 5'-CCCGGGATGACCATGATTACGTCAAG-3' | Xma I |
| VGFPR | 63 | 5'-GGCGCGCCTTACTTGTACAGCTCGTCCATGC-3' | Asc I |
| TORR1L | 64 | CAGTCCTGAAACTATCTGCGG | |
| TORR1R | 65 | TACGGCACGCTCATTTAAAAC | |
| TORR23L | 66 | AACCCTTACATGACATGCTCG | |
| TORR23R | 67 | AATCACCTGCATAACACGCTC | |
| TORR4L | 68 | GGCTTTGATGATCTGCTGAAC | |
| TORR4R | 69 | AACACGGCACTACAAAGTTGG | |
| TORR56L | 70 | TGTAATCATTAAACCGCTCGG | |
| TORR56R | 71 | ATCACATGGTGAAGTTCCTCG | |
| TORR7L | 72 | AGAATTCGCATAAGCGAGTTG | |
| TORR7R | 73 | CTTTAATGGATGGAGCTGCTG | |
| TORR8L | 74 | TGCACTTGTTATCTGCACTGC | |
| TORR8R | 75 | TTTCTGGCATCACACAATTTG | |
| TORR9L | 76 | TGTCCCTGTAGATTGCTCCAC | |
| TORR9R | 77 | GGCAGTCAAACTATCAGCCTG | |

Sequencing was done to verify in-frame between attL1 and GUS ORF. A 2.7 Kb region upstream of the TOR translational start site was amplified using forward primer PTORF and reverse primer PTORR (see Table 3). PCR products, were cloned into TA cloning vector pCR2.1-TOPO (Invitrogen, Cat. K2000-01) for sequencing. After digestion by Asis I and Not I, it was subcloned into the Asis I/Not I cassettes upstream of the GUS coding region to generate p8GWG(TOR::GUS) TOR::GUS was transferred into pEarleyGate303 through LR recombination reactions. GUS assays were as described (Bla'zquez 1997).

Generation of p8GWC (attL1/AsisI/TOR::TORKD:vGFP/AscI/attL2) and Constructions for Protein Localization Based on p8GWN, p8GWC (TOR::TORKD:vGFP) vector was created using the forward primer and reverse primer. 813 bp vGFP was PCR amplified by forward primer and reverse primer. As above, 2.7 kb TOR promoter and 813 bp vGFP were fused upstream and downstream of TORKD. TOR::TORKD:vGFP was transferred into pEarleyGate303 through LR recombination reactions. The resulting plasmids were transformed into different TOR knockout lines *Arabidopsis* plants (Col) by the floral dipping method (Clough 1998).

Isolation of T-DNA Insertion Lines

To identify TOR insertional, the following salk lines were ordered from ABRC: SAIL_1149_B04; SALK_043130; SALK_138622: SALK_013925; SALK_016286; SALK_028697; SALK_017177; SALK_147473; SALK_007654; SALK_036379. The knockout lines were identified by PCR with primers designed from T-DNA Primer Design website: http://signal.salk.edu/tdnaprimers.2.html.

Referring to FIGS. 1A and 1B, insertion/knockout mutants (tor-1, tor-2, tor-3, tor-4, tor-5) from N to C terminal of TOR are depicted. In tor-1, HEAT repeats. FAT, FRB, kinase and FATC domains are knocked-out and the line was embryo defective with decreased rRNA expression. In mutants tor-2 and tor-3, part or all of the HEAT repeats were not knocked out while FAT, FRB, kinase and FATC were knocked-out resulting in a line that was also embryo defective with decreased rRNA expression. In tor-4, the FAT and FRB domains as well as the HEAT repeats remained with the kinase and FATC domains knocked-out also resulting in a line that was embryo defective with decreased rRNA expression. However, in tor-5, the kinase domain as well as the HEAT repeats, FAT and FRB domains were not knocked-out with only the FATC domain knocked-out resulting in a line that was not embryo defective and did not have decreased rRNA expression pr detectable embryo or post-embryo phentoypes. Thus, it appears that TOR kinase domain is essential for embryo development and rRNA synthesis in *Arabidopsis*. The kinase domain in AtTOR is a 300 amino acid sequence from amino acid 2050 to 2350 of SEQ ID NO: 2.

TOR Kinase and NLS Mutant and Truncation Plasmid Constructions

The TOR1 kinase and NLS mutation was introduced by PCR overlap mutagenesis using primers and the cDNA clone. The PCR product was cloned into PCR2.1 TOPO using the TA cloning Kit and the recommandent plasmids had been cleaved with NotI and XmaI and subcloned into plasmid p8WGC. All other internal deletions were generated by PCR overlap mutagenesis using the TaKaRa long-range PCR system from Intergen Deletion 1962-2051 was generated with overlapping primers.

Figure 2:
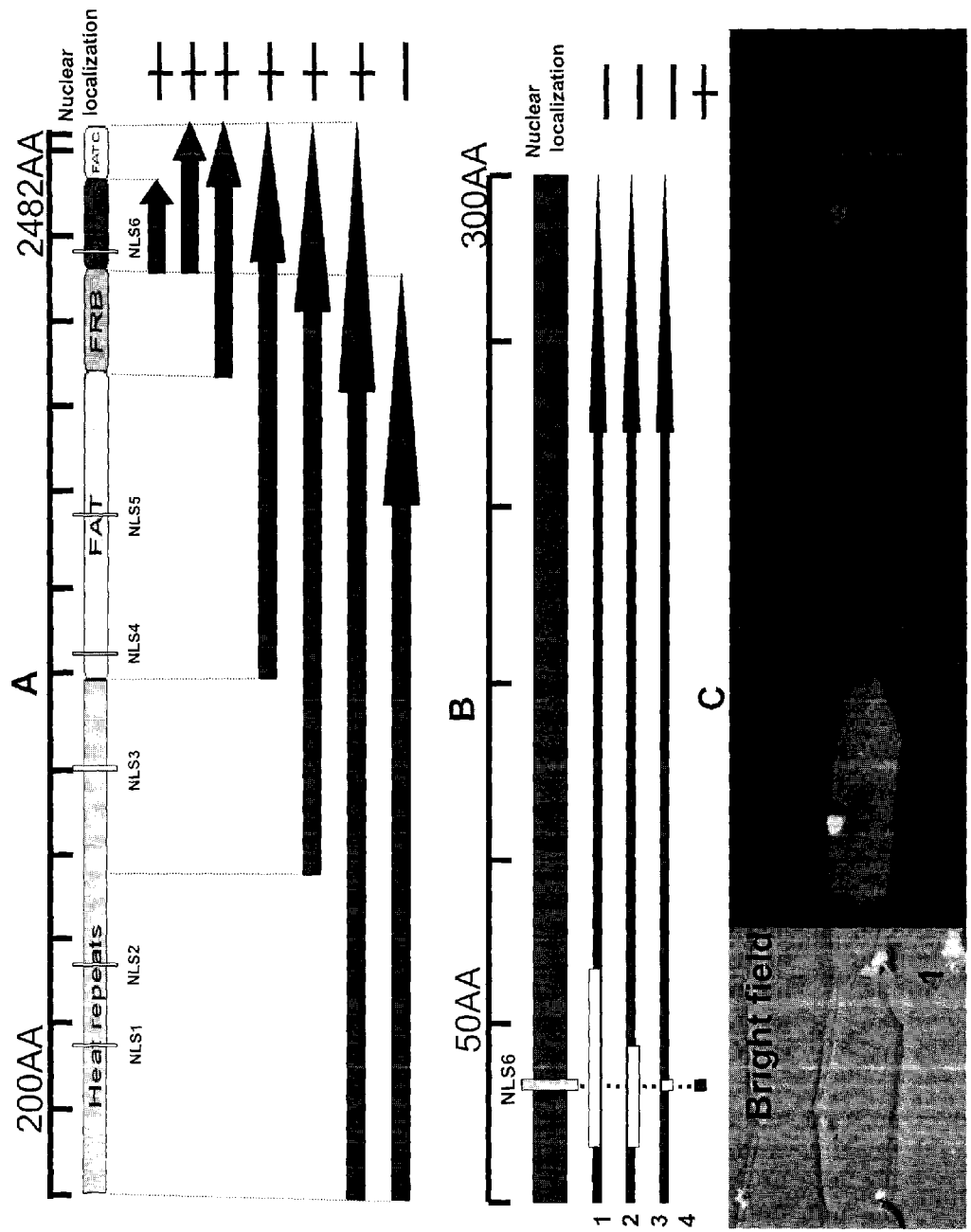
FIG. 2A depicts distribution of six putative nuclear localization sites (NLS) in AtTOR and generation of a series of AtTOR deletion mutants fused with green fluorescent protein (GFP) and expression in onion epidermal cells show that NLS of AtTOR resides in kinase domain
FIG. 2B illustrates that RPRK motif is essential for AtTOR nuclear localization.
FIG. 2C depicts representative images of AtTOR nuclear localization. Onion epidermal cells were examined under bright-field (1). Transient expression of AtTOR:GFP construct in onion epidermal cells show the localization of GFP signal in both nucleus and cytoplasm (2). DAPI nuclear staining (3). DAPI+GFP co-localization (4).

Referring to FIGS. 2A, 2B and 2C, domains required for nuclear localization of AtTOR were characterized. Six putative nuclear localization sites (NLS1-NLS6) were identified and six deletion mutants (TOR2050-2350, TOR2031-2482, TOR1832-2482, TOR1433-2482, TOR652-2482 and TOR1-2050, where the numbers refer to the amino acids remaining in the deletion mutant) were compared to the full-length TOR (TOR) to identify which of the six putative putative nuclear localization sites (NLS) is the correct one. FIG. 2A demonstrates that NLS6 located in the kinase domain is the NLS. To more exactly determine the amino acid sequence responsible for nuclear localization, three deletion mutants within the kinase domain surrounding NLS6 were made (FIG. 2A) and it appears that RPRK motif (aa 2077-2080 of SEQ ID NO: 2) is essential for AtTOR nuclear localization. In BnTOR, the kinase domain is located at aa 2049-2349 of SEQ ID NO: 4 and the RPRK motif at aa 2076-2079 of SEQ ID NO: 4.

Figure 3:
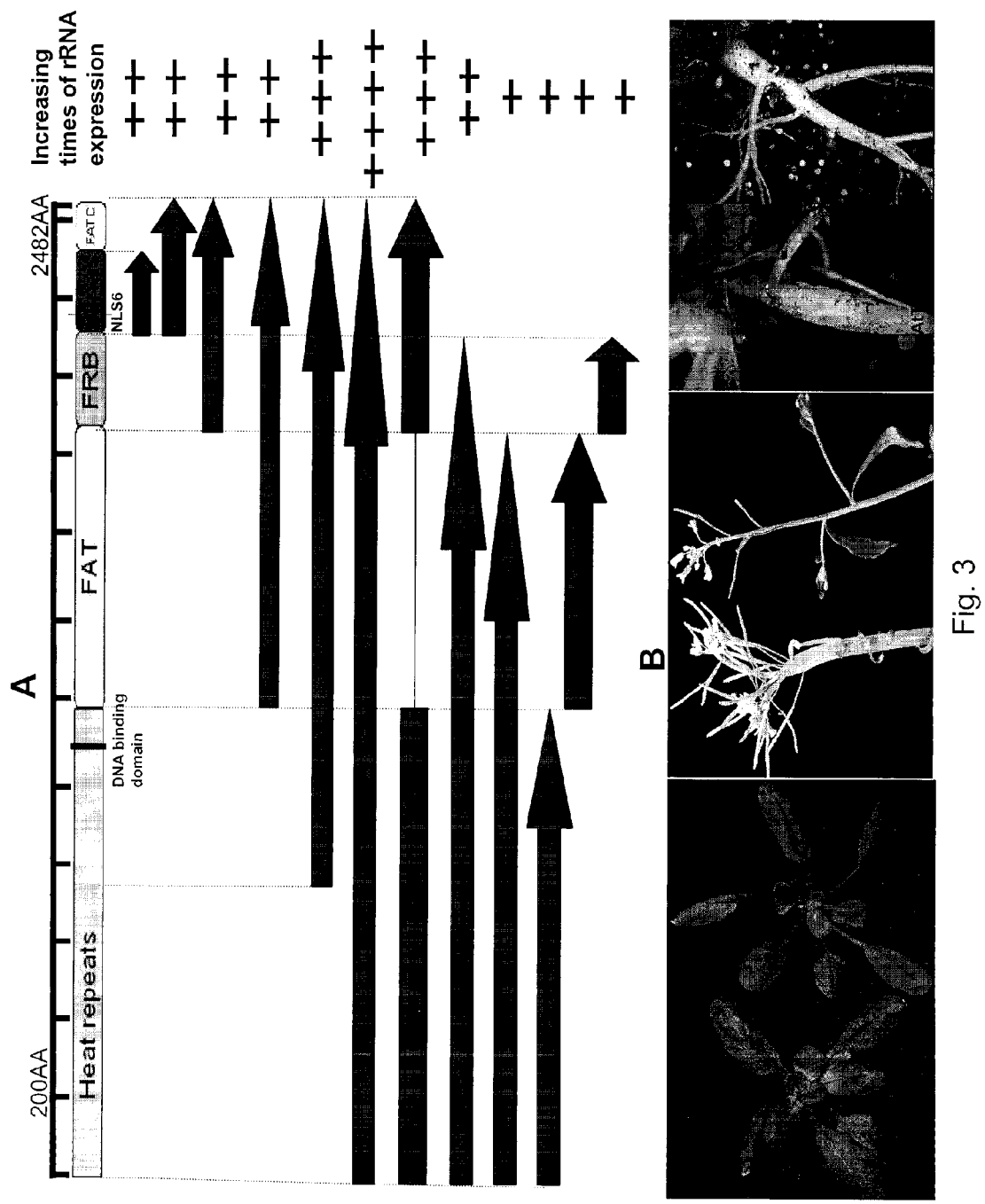
FIG. 3A depicts full-length AtTOR and deletion derivatives of AtTOR, and phenotypes of ectopically expressed AtTOR and it's deletion derivatives with reference to ribosomal RNA (rRNA) expression. The symbols: +, ++, +++ and ++++ corresponds to 1, 2, 3 and 4 fold increases in rRNA expression, respectively.
FIG. 3B depicts representative phenotypes of over-expressed AtTOR and its deletion derivates in transgenic *Arabidopsis*: (1) larger and thicker leaves, (2) enlarged stem, (3) altered root architecture.

Referring to FIGS. 3A and 3B, AtTOR (TOR) and eleven deletion derivatives of AtTOR (TOR2050-2350, TOR2031-2482, TOR1832-2482, TOR1433-2482, TOR652-2482, TOR1-1399/1801-2482), TOR1-2050, TOR1-1900, TOR1-1400, TOR1400-1800 and TOR1900-2050, where the numbers refer to the amino acids remaining in the deletion derivative) were over-expressed in *A. thaliana* under the control of the CaMV 35S promoter. (The deletion derivative TOR1-1399/1801-2482 has amino acids 1400-1800 deleted.) Overexpression of the full-length AtTOR and the eleven deletion derivatives corresponding to different functional domains of AtTOR in transgenic plants showed up-regulation of ribosomal RNA expression, and a range of developmental phenotypes. It is evident from FIG. 3A that, in most cases, the kinase domain is important for up-regulation of rRNA expression in transgenic plants. All deletion derivatives retaining the kinase domain show up-regulated rRNA expression while only one of the five deletion derivatives not having the kinase domain show up-regulation, and that one (TOR1-2050) is only a effective at up-regulating rRNA expression as the least of the deletion derivatives that retains the kinase domain. FIG. 3B shows that transgenic plants over-expressing AtTOR have larger and thicker leaves, enlarged stems and altered root architecture compared to wild-type (WT) plants grown under the same conditions.

Figure 4:
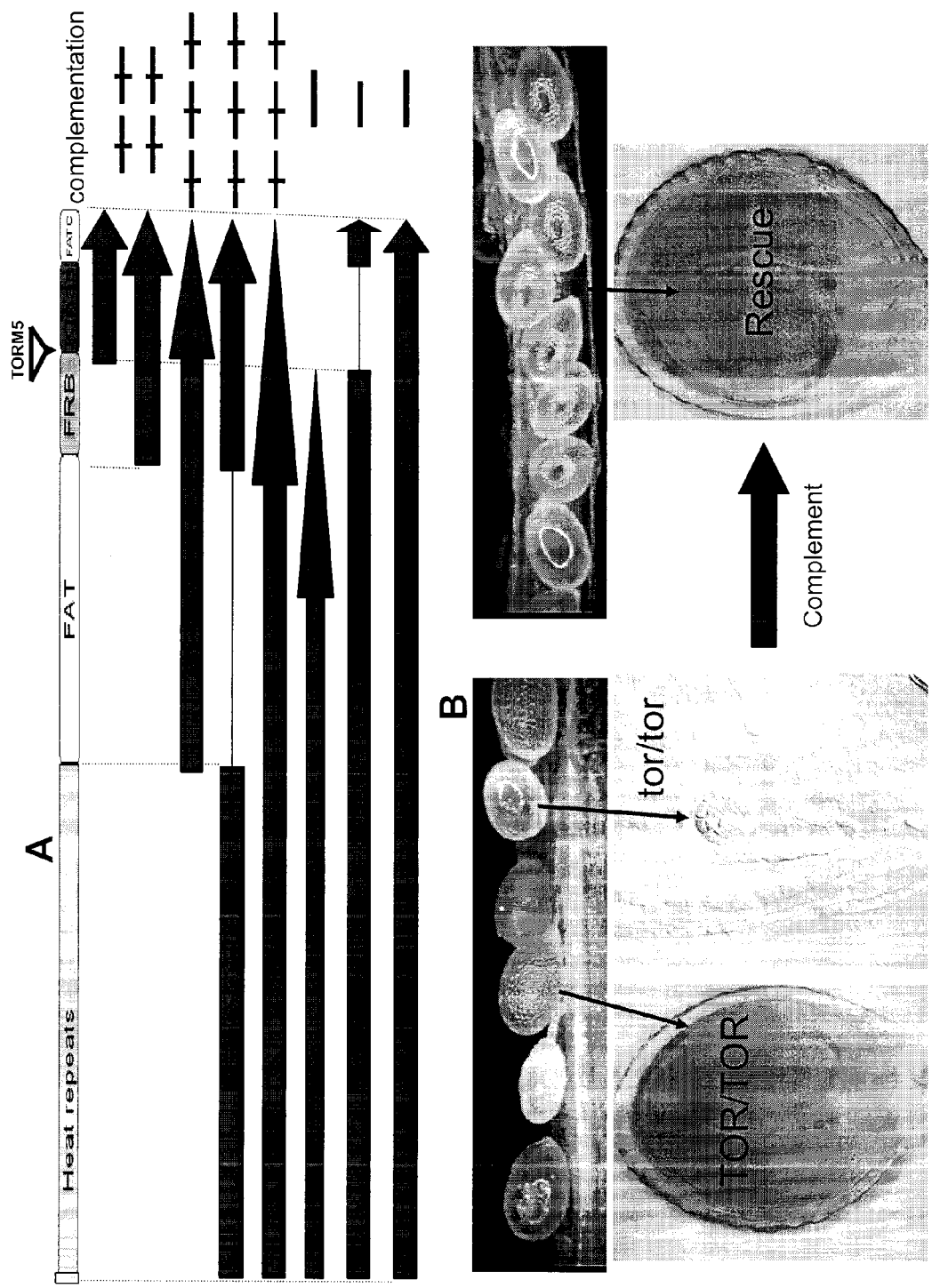
FIG. 4A depicts a functional complementation assay in TORM5/torm5 background which shows that NLS6 can partially rescue the torm5/torm5 mutant phenotypes, while deletions without NLS6 fail to rescue embryo lethality.
FIG. 4B depicts representative images of the AtTOR functional complementation.

Referring to FIGS. 4A and 4B, functional complementation assays in TORM5/torm5 background demonstrate that nuclear localization of AtTOR is important for embryo/seed development in *Arabidopsis*. Full-length AtTOR (TOR) and four deletion derivatives (TOR2031-2482, TOR1832-2482, TOR1433-2482, and TOR1-1399/1801-2482, where the numbers refer to the amino acids remaining in the deletion derivative) retaining the NLS6 site were shown to at least partially rescue the torm5/torm5 mutant phenotypes. However, three deletion derivatives (TOR1-2050. TOR1-2049/2351-2482 and TOR1-2076/2081-2482, where the numbers refer to the amino acids remaining in the deletion derivative) not containing NLS6 failed to rescue embryo lethality. (The deletion derivative TOR1-1399/1801-2482 has amino acids 1400-1800 deleted, TOR1-2049/2351-2482 has amino acids 2050-2350 deleted, and TOR1-2076/2081-2482 has amino acids 2077-2080 deleted.)

Figure 5:
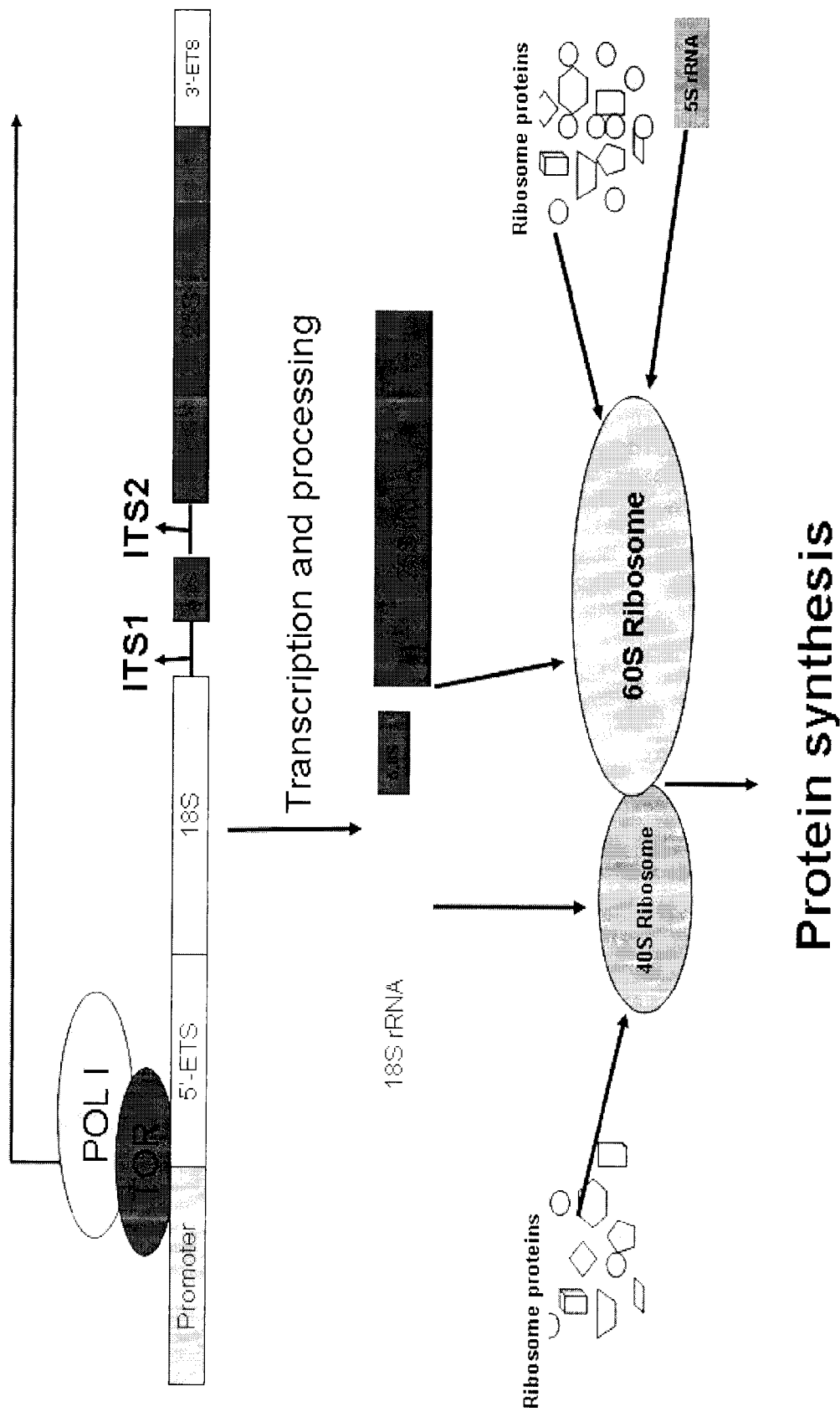
FIG. 5 depicts a model for TOR regulation of ribosome biogenesis in *Arabidopsis*.

Referring to FIG. 5, a proposed model for TOR regulation of ribosome biogenesis in *Arabidopsis* is illustrated. Over-expression of AtTOR leads to a pronounced increase of ribosome RNA expression, while loss function of AtTOR causes severe repression of ribosome RNA synthesis. *Arabidopsis* Columbia ecotype was used in all the transformation studies.

Example 3

Identification of TOR-Interacting Proteins (TIPs)

Figure 6:
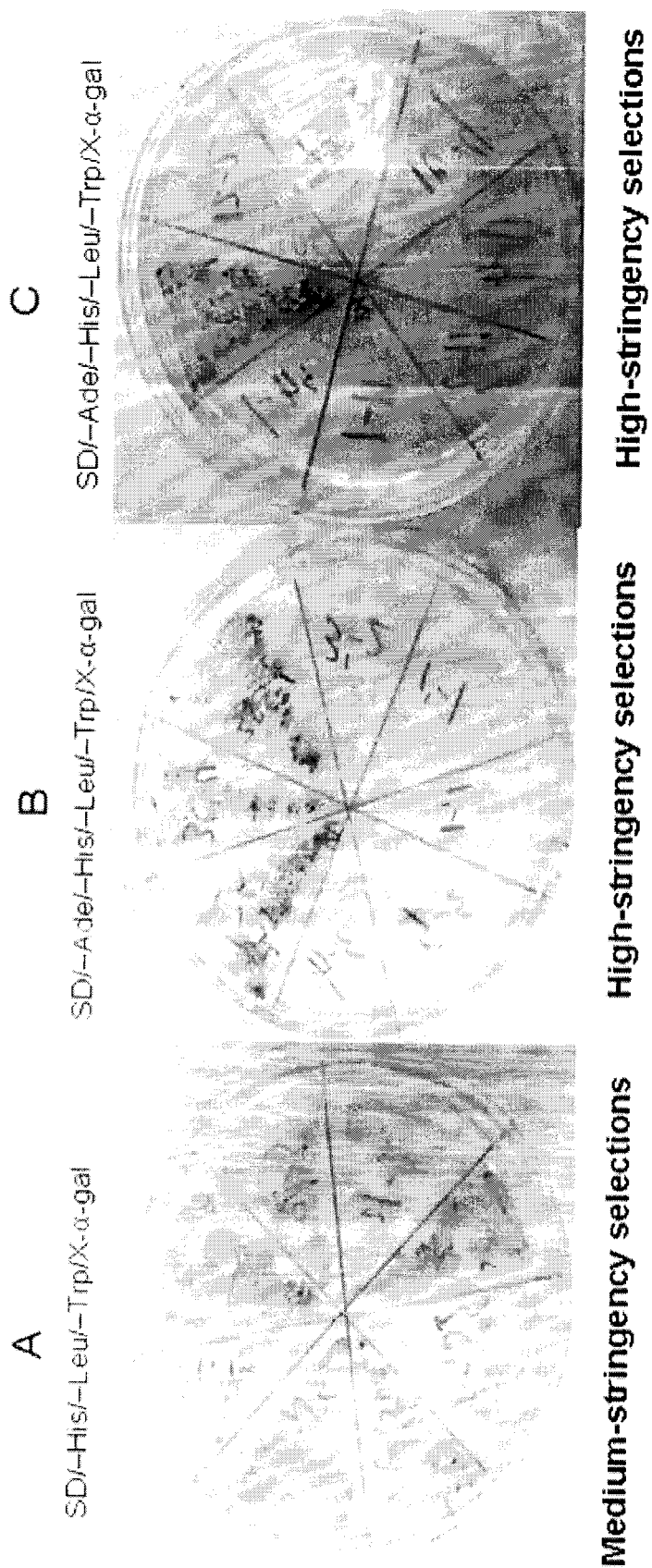
FIG. 6 depicts yeast culture dishes showing identification of TOR interacting proteins (TIPs) using a yeast two hybridization system.

Referring to FIG. 6, a yeast two hybridization system was used to identify thirty TOR interacting proteins (TIP1 to TIP30) in *Arabidopsis* from screening of more than 100 putative candidates in the TOR signaling network in *Arabidopsis*. Proteins that show interaction with AtTOR in the yeast two hybrid assay are designated as TOR-Interacting Proteins (TIPs). It was found that TOR itself is a TIP, thus the label TIP1 is synonymous with TOR in this description. Throughout the Figures, reference to a TIP is made in the context of the plant species from which the TIP is derived. Thus, when the context is *A. thaliana*, TIP1 (TOR) is AtTIP1 (AtTOR), TIP2 is AtTIP2, etc., and in the context of *B. napus*, TIP1 (TOR) is BnTIP1 (Bn(TOR). TIP2 is BNTIP2, etc.

In the yeast two hybrid method, cDNAs of TOR and its truncations as well as AtTIP2, AtTIP5. AtTIP6, AtTIP7, AtTIF8. AtTIP9, AtTIP13, AtTIP15. AtTIP16 and AtTIP28 were generated by RT-PCR, cloned into p8GWN NotI/XmaI cassettes box, transferred into pDEST™ 32 (Ampicillin resistance) and pDEST™ 22 (Gentamicin resistance) by LR recombination reactions respectively, and transformed into the yeast host strains MaV203 for interaction assays. All the Y2H procedures were performed according to the manufacture's instruction (Invitrogen; cat no PQ10001-01). As above, based on the pCR8/GW/TOPO backbone, the Entry vector p8GWG with Asis I-promoter-Not I-GUS-Asc I and p8GWC with Asis I-promoter-Not I-CDS-Xma I+vGFP+Asc I cassettes was created PCR strategy. In this system, the Pearleygate gateway-compatible vectors were used for destination vectors and the pCR8/GW/TOPO (Invitrogen, Cat. K2500-20) was used as the backbone plasmid of entry clones. As above, the Pearleygate gateway-compatible vectors were used for destination vectors and the pCR8/GW/TOPO (Invitrogen, Cat. K2500-20) was used as the backbone plasmid of entry clones. To recombine the sequences of interest into the pCR8/GW/TOPO vector, inserts were generated by PCR.

Example 4

Silencing of TOR-Interacting Proteins (TIPs)

Figure 7:
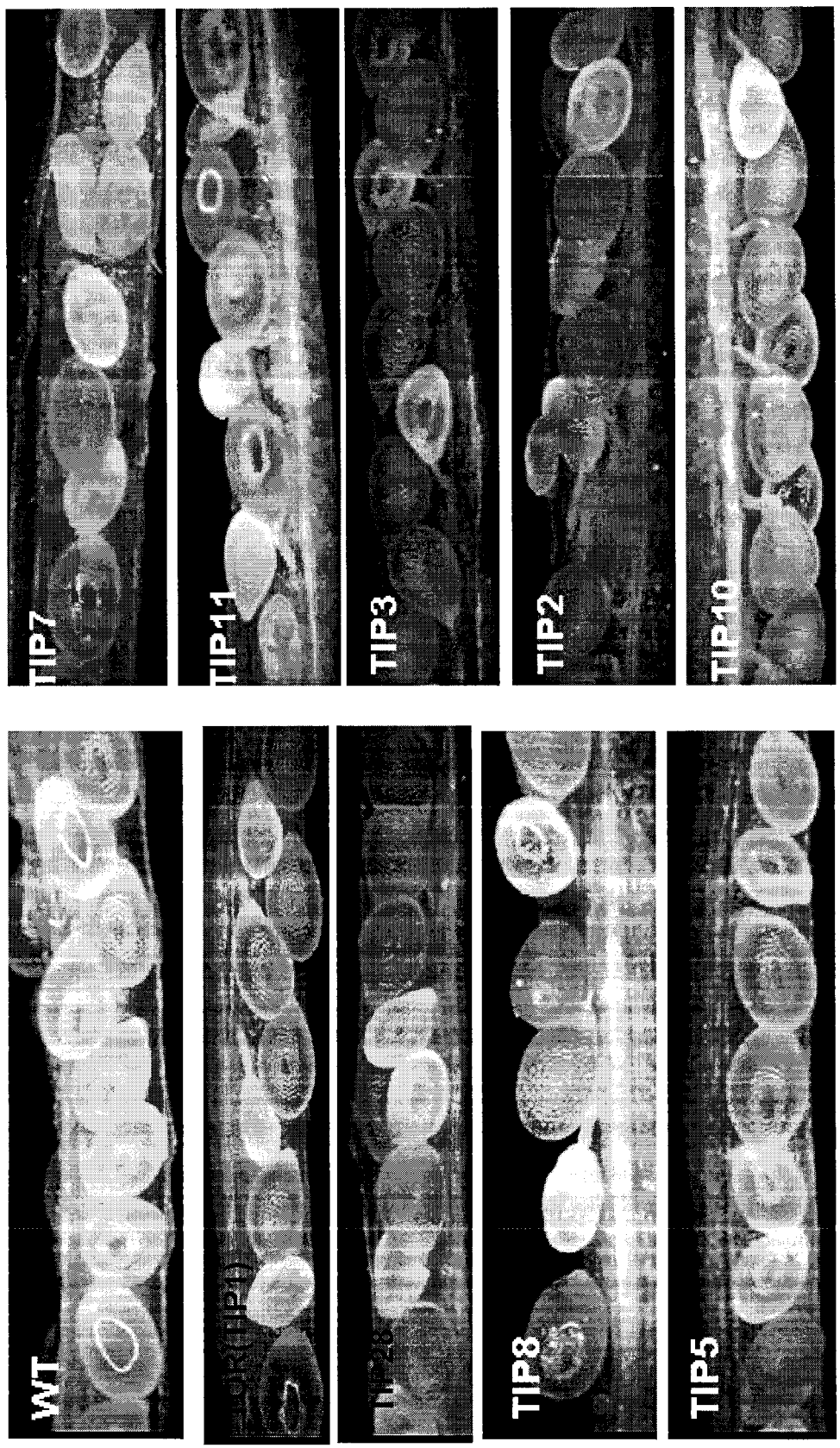
FIG. 7 depicts illustrations of embryos grown from cells in which expression of various TOR interacting proteins (TIPs) has been knocked-out.

Referring to FIG. 7, knockout of several TIPs (TIP1(TOR), TIP2, TIP3, TIP5, TIP7, TIP8, TIP10, TIP11) implicated in TOR pathway leads to *Arabidopsis* lines having embryo defective phenotypes. Wild-type (WT) and full-length AtTOR over-expression lines are shown as controls. Analysis of the TIP knockout lines revealed developmental blocks leading to embryo lethality phenocopying AtTor mutants, suggesting likely conserved functions as a complex in similar pathways. It is evident that TIPs are required for normal embryo/seed development in *Arabidopsis*.

Example 5

Over-Expression of TOR-Interacting Proteins (TIPs)

Isolation of DNA, Purification of Total RNA and cDNA Synthesis

Genomic DNA and Total RNA was isolated from 2-week-old *Arabidopsis thaliana* seedlings (ecotype Columbia) using DNeasy Plant Mini Kit (Cat. No. 69104) and RNeasy Plant Mini Kit (QIAGEN, Cat. No. 74904) following the manufacturer's instructions. A SMART RACE cDNA amplification kit (Clontech, cat. No. 634914) was used for cDNA amplification following the manufacturer's instructions.

The full-length cDNAs of AtTIP2, AtTIP5, AtTIP6, AtTIP7, AtTIP8, AtTIP9, AtTIP13, AtTIP15, AtTIP16, AtTIP28 and corresponding *B. napus* TIPs were amplified by RT-PCR using the Advantage® 2 Polymerase Mix kit (Clontech, Cat. No. 639201) following the manufacturer's instructions. Three overlapping fragments were amplified and fused together by using the restriction enzymes (BspEI and BlpI) to generate the full-length clone. The sequences were verified by DNA sequencing.

Construction of the p8GWN(attL1/NotI/TORKD/AscI/attL2) Entry Vector and Over-Expression Constructions A gateway system for creating various expression plasmids using the LR recombination reaction (Invitrogen) was used. The construction of the Entry vector p8GWN is based on the pCR8/GW/TOPO (Invitrogen, Cat. K2500-20) plasmid, comprising a TOPO AT cloning site flanked by attL1 and attL2 sites. This was used as the backbone plasmid in LR recombination reactions containing the bacterial selection marker (spectionomycin resistance) which differs from the destination vectors: pEarleyGate vectors comprising (kanamycin resistance), pDEST15 comprising (Ampicillin resistance), pDEST™ 32 comprising (Ampicillin resistance) and pDEST™ 22 comprising (Gentamicin resistance). To create p8GWN, inserts were amplified by PCR using forward primers adding a Not I site at the 5' end and reverse primers with XmaI I site at the 5' end. Cloned PCR products were directly inserted into pCR8/GW/TOPO and sequenced to make sure the in-frame between attL1 sequence and ORF of target gene.

After confirming the sequence, wild type AtTIP2, AtTIP5, AtTIP6, AtTIP7, AtTIP8, AtTIP9, AtTIP13, AtTIP15, AtTIP16 and AtTIP28 sequences were cloned as PCR products into p8GWN to generate the gateway system Entry vector. Respective plant expression constructs were generated by transferring to pEarleyGate 203 vectors through LR recombination reactions. A map of the construct is depicted in FIG. 12C using TIP2 as an example. The resulting plasmid was used to transform wild-type *Arabidopsis* plants (Col) by the floral dipping method (Clough 1998) and *Brassica napus* by the Moloney cotyledonary petiole method (Moloney 1989).

Nutrient Utilization

Figure 8A:
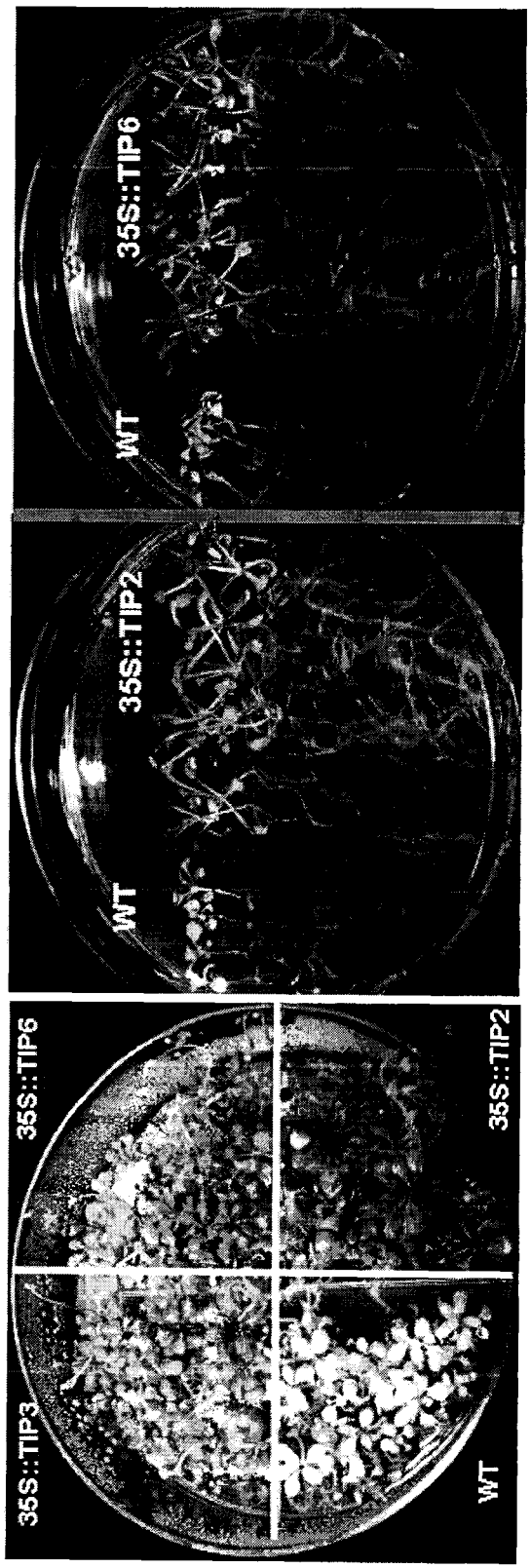
FIG. 8A depicts plant cultures comparing nutrient use-efficiency phenotype of wild-type (WT) *Arabidopsis* plants to gain of function lines (AtTIP2, AtTIP3 and AtTIP6) produced with some of the TIPs.

Referring to FIG. 8A, it is apparent that *Arabidopsis* plants transformed with TIP2, TIP3 or TIP6 under the control of the CaMV 35S promoter exhibit increased nutrient utilization as the transgenic plantlets are bigger and healthier than the wild-type (Col WT) plantlets grown under the same conditions. The in vitro assay for nutrient use was performed under nitrogen limiting conditions ($1/10^{th}$ of normal levels).

Figure 8B:
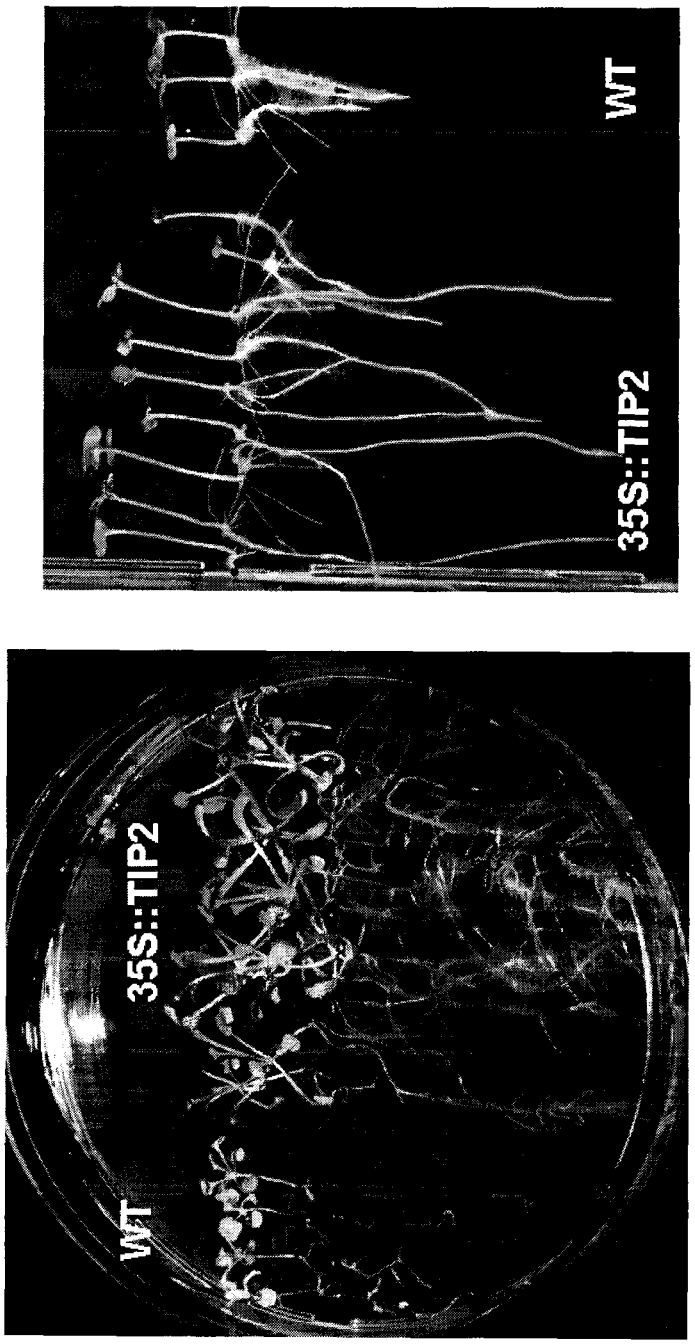
FIG. 8B depicts plant cultures of transgenic *Arabidopsis* and *B. napus* plants transformed with TIP2 under the control of the CaMV 35S promoter showing efficient growth in low nitrogen and potassium media.

TIP2 encodes a putative protein kinase, which is a member of the AGC protein kinase family. Referring to FIG. 8B, transgenic plants with over-expression of TIP2 under the control of CaMV 35S promoter in *Arabidopsis* and *Brassica napus* show better nitrogen and potassium use efficiency. Compared with control plants, they displayed normal growth and development under limiting conditions with $1/30^{th}$ nitrogen and potassium levels in the medium. Results from this study showed that normal root growth is maintained in transgenic *Arabidopsis* and *B. napus* plants despite significantly lower levels of these nutrients.

Figure 8C:
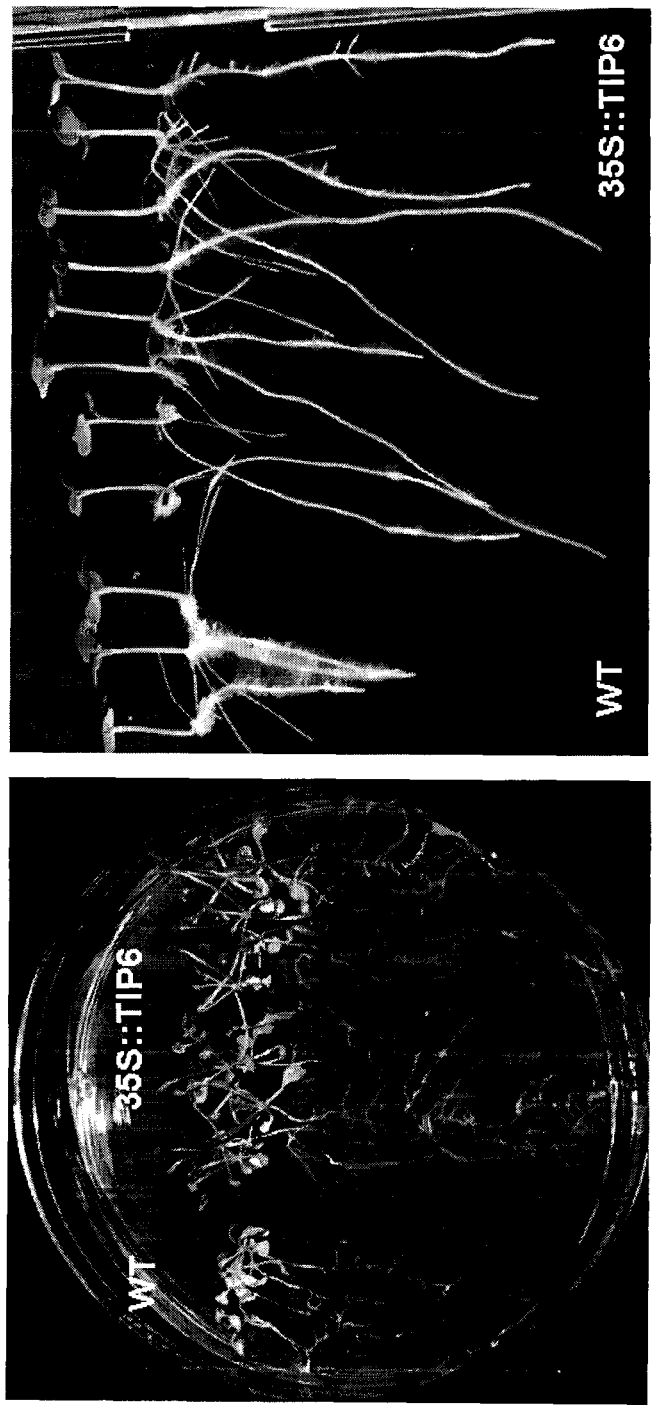
FIG. 8C depicts plant cultures of transgenic *Arabidopsis* and *B. napus* plants transformed with TIP6 under the control of the CaMV 35S promoter showing efficient growth in low nitrogen and potassium media.

TIP6 encodes a putative 3-phosphoinositide-dependent protein kinase and contains pleckstrin domain Referring to FIG. 8C, transgenic plants with over-expression of TIP6 under the control of the CaMV 35 promoter in *Arabidopsis* and *Brassica napus* show better nitrogen and potassium use efficiency. Compared with control plants, they displayed normal growth and development in $1/30^{th}$ nitrogen and potassium in in vitro assays.

Plant Morphology

Figure 9A:
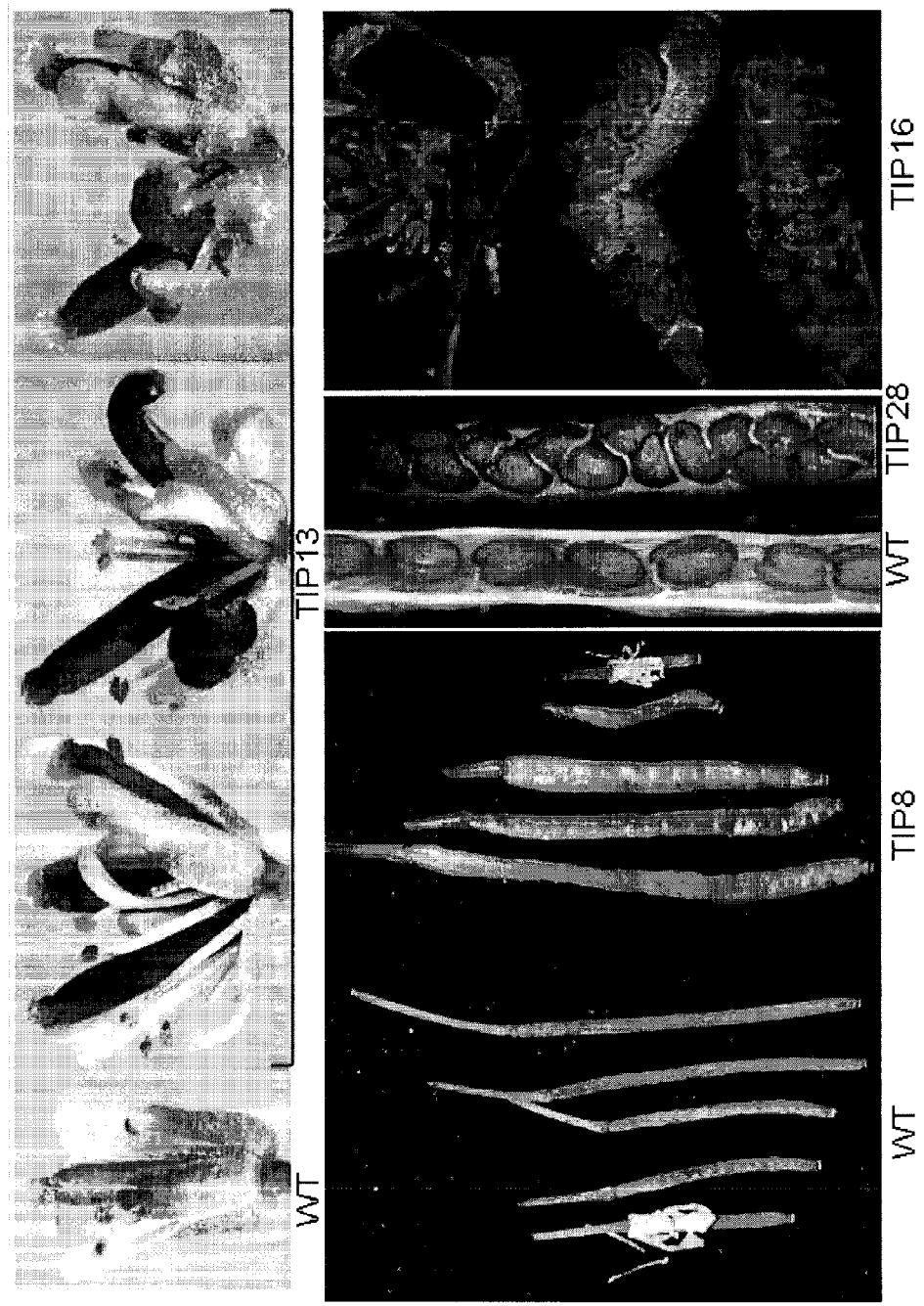
FIG. 9A depicts wild-type (WT) and transgenic TIP (AtTIP13, AtTIP8. AtTIP28 and AtTIP16) *Arabidopsis* plants or seeds comparing leaf, flower, inflorescence, architecture, silique and seed characteristics.
Figure 9B:
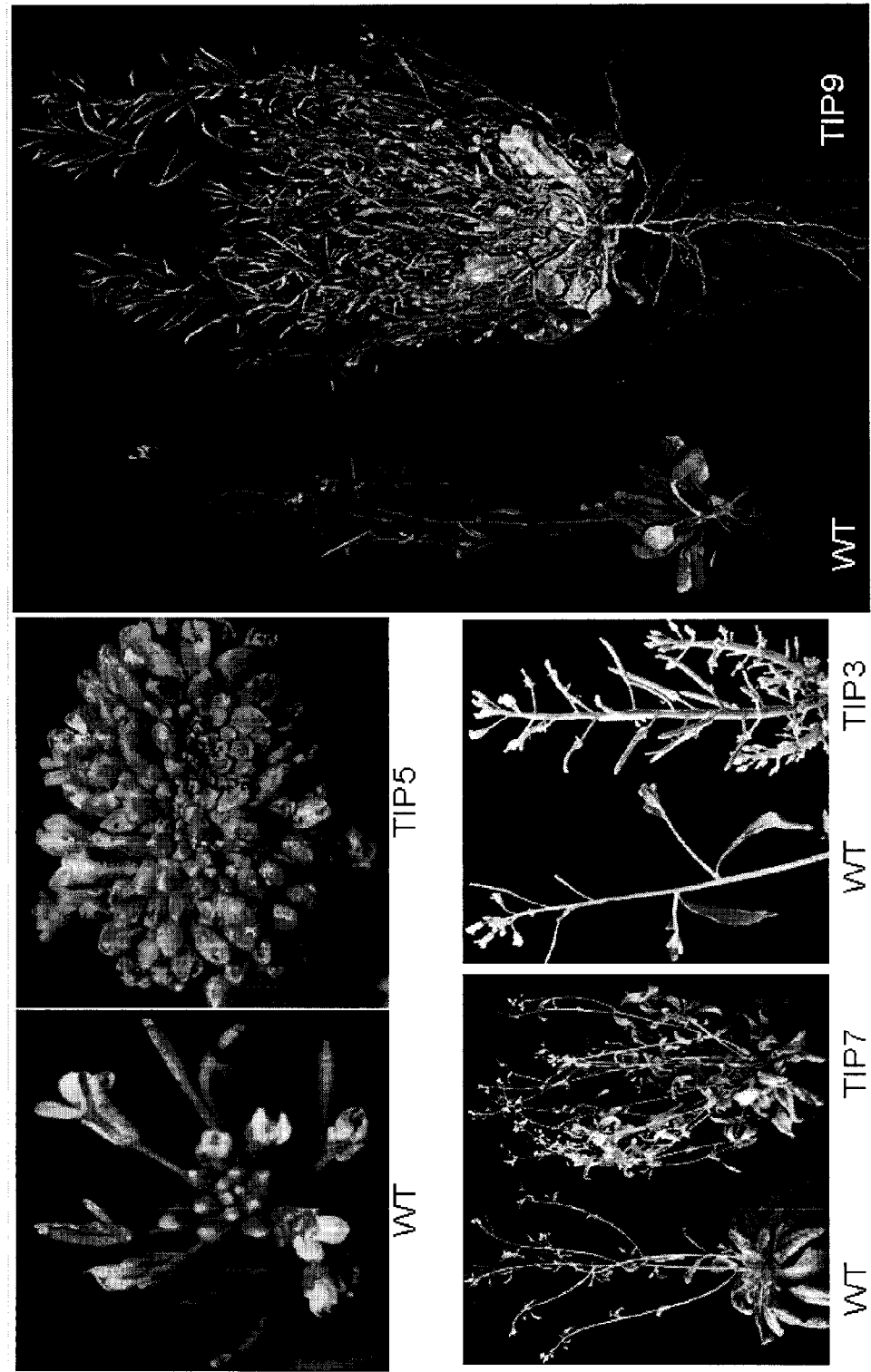
FIG. 9B depicts wild-type (WT) and transgenic TIP (AtTIP5. AtTIP7, AtTIP3 and AtTIP9) *Arabidopsis* plants comparing leaf, flower, inflorescence, architecture and silique characteristics.

Referring to FIGS. 9A and 9B, a comparison of plant and seed characteristics between wild-type (Col WT) and transgenic TIP (TIP3, TIP5, TIP7, TIP8. TIP13, TIP16 and TIP28) *Arabidopsis* plants or seeds shows that ectopic expression of TIPs alters developmental programs involving meristem, leaf, flower, inflorescence, architecture, silique and seed. Phenotypes produced by the over-expression of TIPs include increased seed number, flower number and branches. Earlier flowering times for TIPs plants of up to 14 days in greenhouses and up to 10 days in the field were noted, i.e. TIPs plant flowered up to 14 days sooner in greenhouses and up to 10 days sooner in the field than wild-type plants.

Figure 9C:
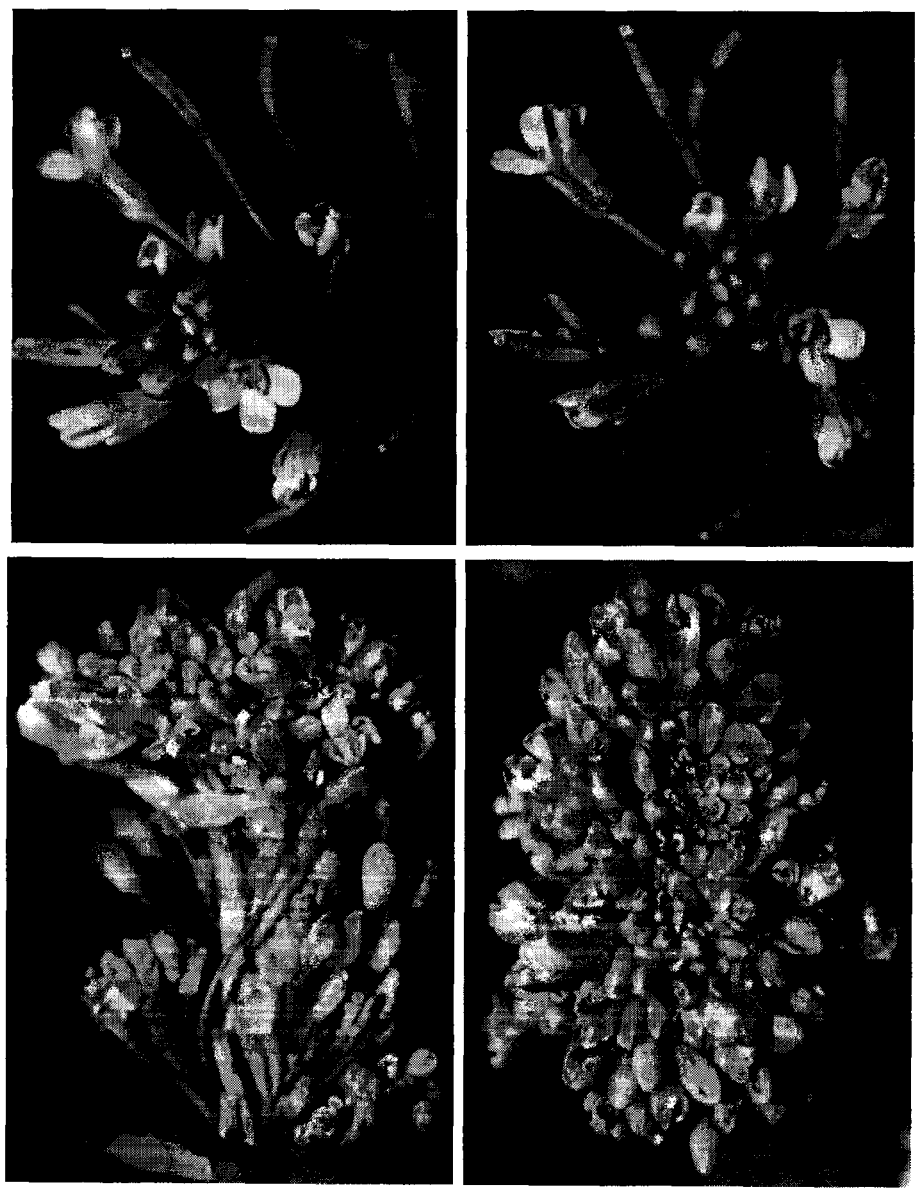
FIG. 9C depicts wild-type (WT) and transgenic AtTIP5 *Arabidopsis* plants showing larger meristem and more flowers.

TIP5 encodes a putative eukaryotic translation initiation factor 2 subunit 1(eIF-2A) and has translation initiation factor activity. Referring to FIG. 9C, ectopic expression TIP5 under the control of the CaMV35S promoter in *Arabidopsis* transgenic lines produced larger meristem and more flowers.

Figure 9D:
FIG. 9D depicts wild-type (WT) and transgenic AtTIP7 *Arabidopsis* plants showing more branches.

TIP7 encodes a putative signal transducin protein. This protein contains 7 WD-40 repeats. Referring to FIG. 9D, over-expression constructs of TIP7 under the control of the CaMV35S promoter in transgenic *Arabidopsis* lines produced more branches.

Figure 9E:
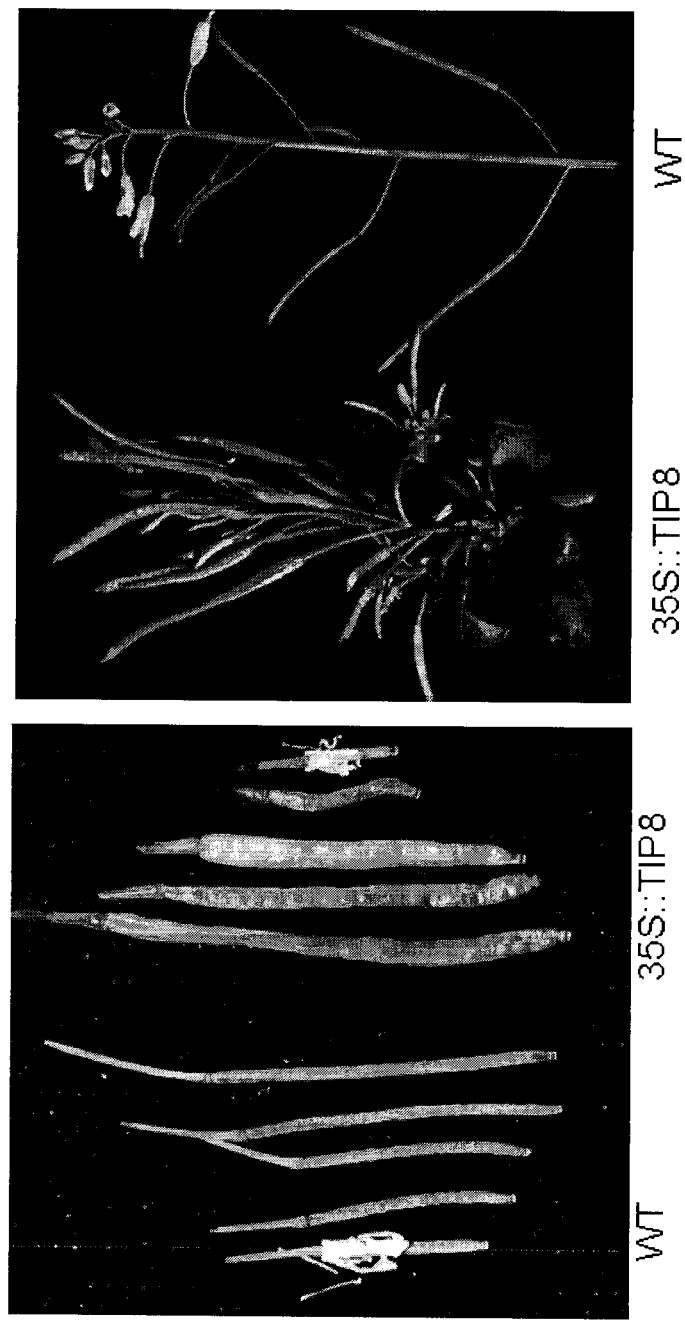
FIG. 9E depicts wild-type (WT) and transgenic AtTIP8 *Arabidopsis* plants showing larger siliques.

TIP8 encodes a putative 14-3-3 anchor protein. Referring to FIG. 9E, over-expression of TIP8 under the control of the CaMV35S promoter in *Arabidopsis* produced larger siliques.

TIP9 encodes a putative phosphatase 2A associated protein. Referring to FIG. 9B, over-expression of TIP9 under the control of the CaMV35S promoter in *Arabidopsis* produced plants with more branches.

TIP13 encodes a putative transducin protein. This protein contains 7 WD-40 repeats. Referring to FIG. 9A, over-expression constructs of TIP13 gene under the control of the CaMV35S promoter in *Arabidopsis* produced plants with multiple siliques in one flower.

Figure 10A:
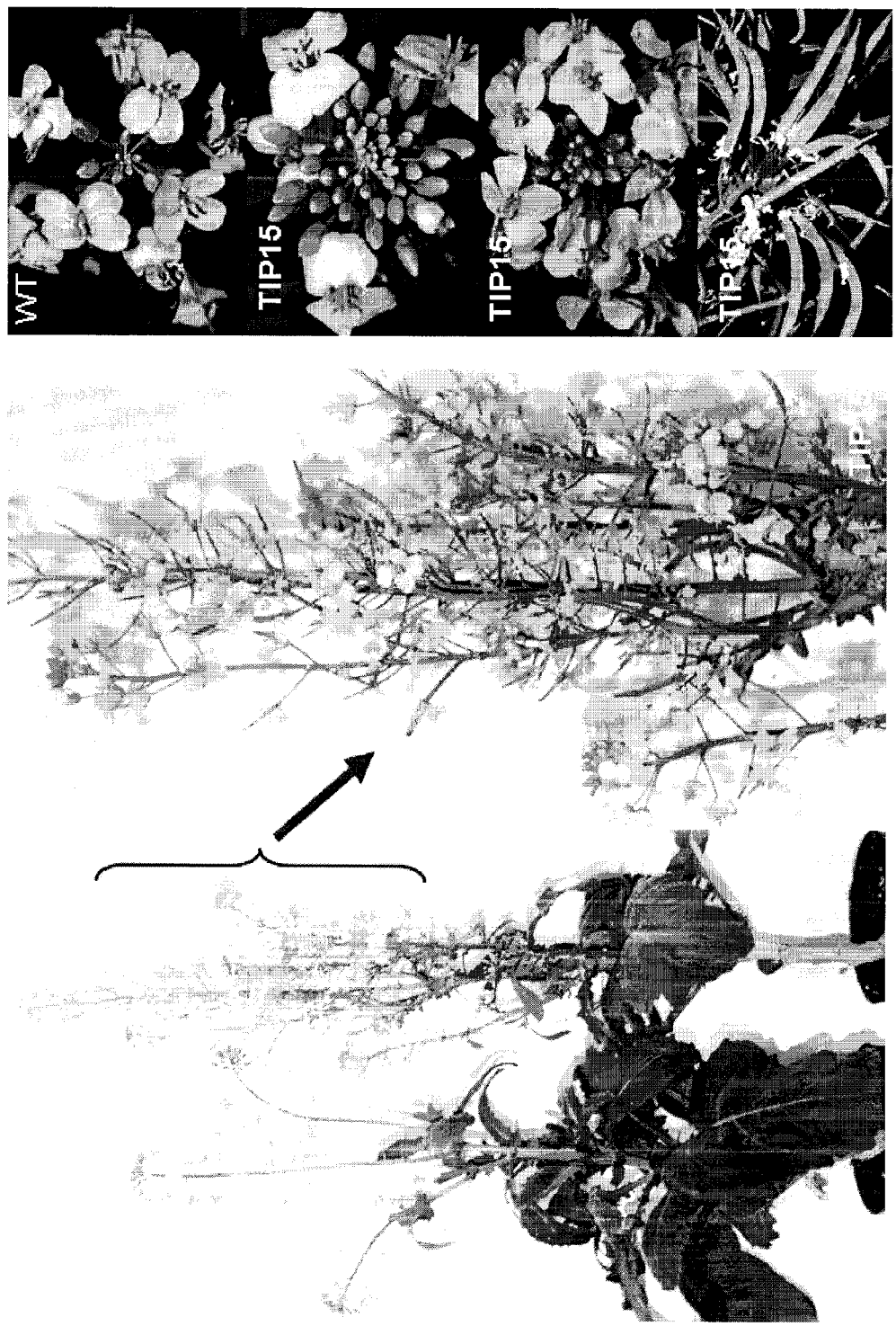
FIG. 10A depicts wild-type (WT) and transgenic BnTIP15 *Brassica napus* plants showing increased branching and increased flower and silique number.

TIP15 encodes a putative transducin family protein. This protein contains WD-40 repeats. Referring to FIG. 10A, over-expression of BnTIP15 under the control of the CaMV35S promoter in transgenic *B. napus* plants showed more branches, flowers and siliques compared to non-transformed control plants.

Figure 10B:
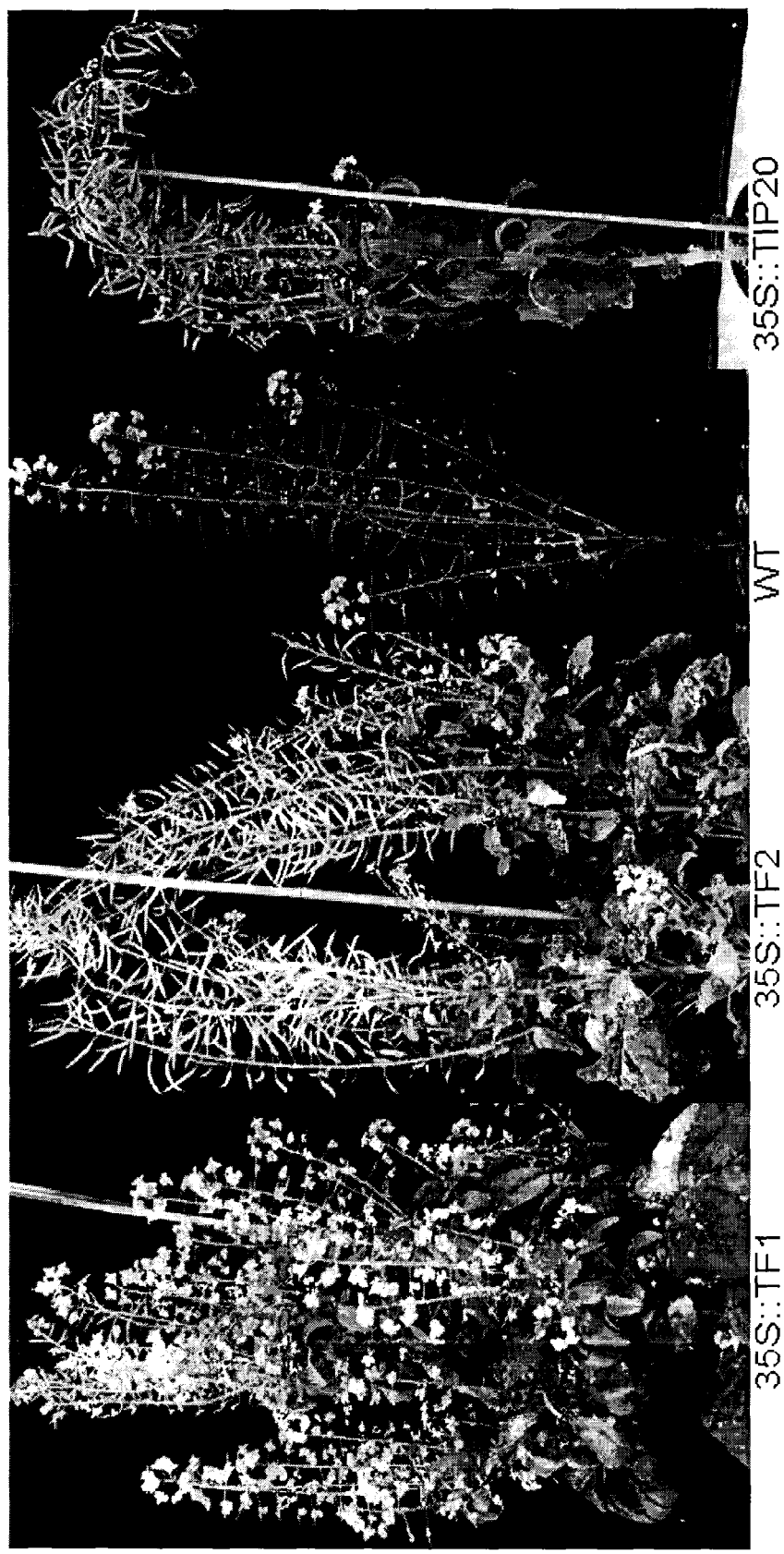
FIG. 10B depicts wild-type (WT), transgenic TF1 (TOR interacting Transcription Factor 1, transgenic TF2 (TOR interacting Transcription Factor 2) and transgenic BnTIP20 *Brassica napus* showing increased branching of transgenic BnTIP20 plants.

Referring to FIG. 10B, the effect of over-expression of BnTIP20 under the control of the CaMV35S promoter on crop performance and yield was demonstrated in *Brassica napus*. Comparison was made to wild-type (DH12075 line—WT) and transgenic (TF1 and TF2) *B. napus* lines. It is evident that transgenic BnTIP20 plants have increased branching in comparison to wild-type plants.

TIP16 encodes a putative serine decarboxylase. In *Arabidopsis*, AtTIP16 under the control of the CaMV35S promoter produced plants showing expanded gynoecium and siliques compared to wild type. In *Brassica napus*, transgenic BnTIP16 plants showed early flowering compared to wild type.

TIP28 shows homology to translation Initiation Factor 2 beta subunit (EIF-2 Beta). In *Arabidopsis*, over-expression of AtTIP28 under the control of the CaMV 35S promoter produced plants with early flowering compared to wild type. In transgenic *Brassica napus*, over-expression of BnTIP28 under the control of the CaMV 35S promoter also produced plants with early flowering.

Seed Morphology

Figure 11A:
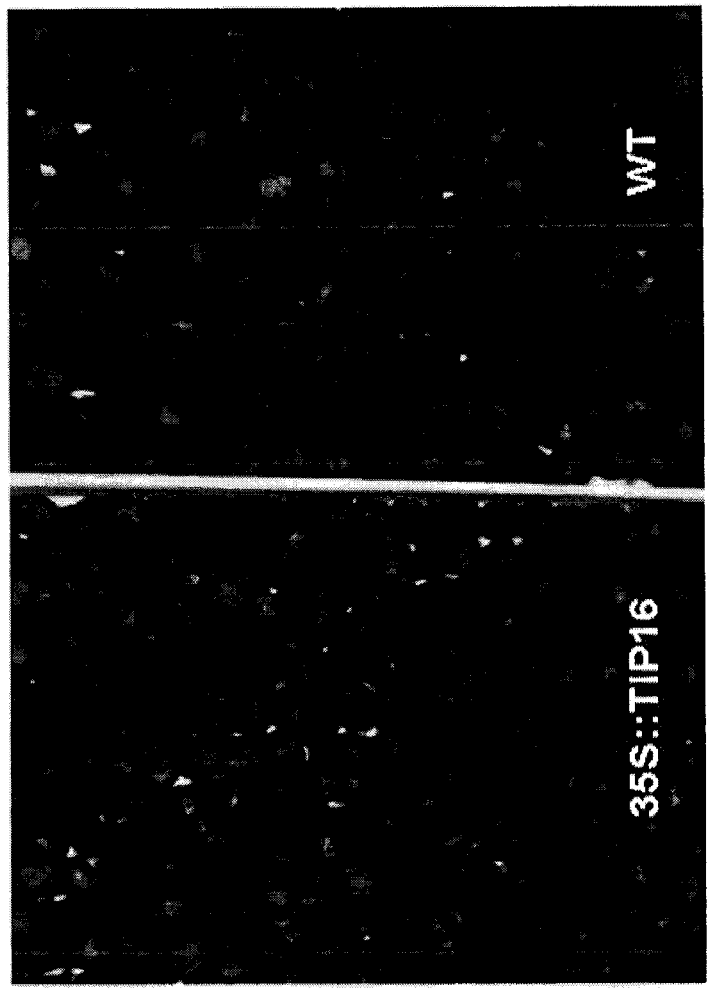
FIGS. 11A, 11B and 11C depict wild-type (WT) and transgenic TIP (BnTIP1 (TOR), BnTIP15 and BnTIP16) *Brassica napus* seeds comparing seed color and seed size.
Figure 11A:
Figure 11B:
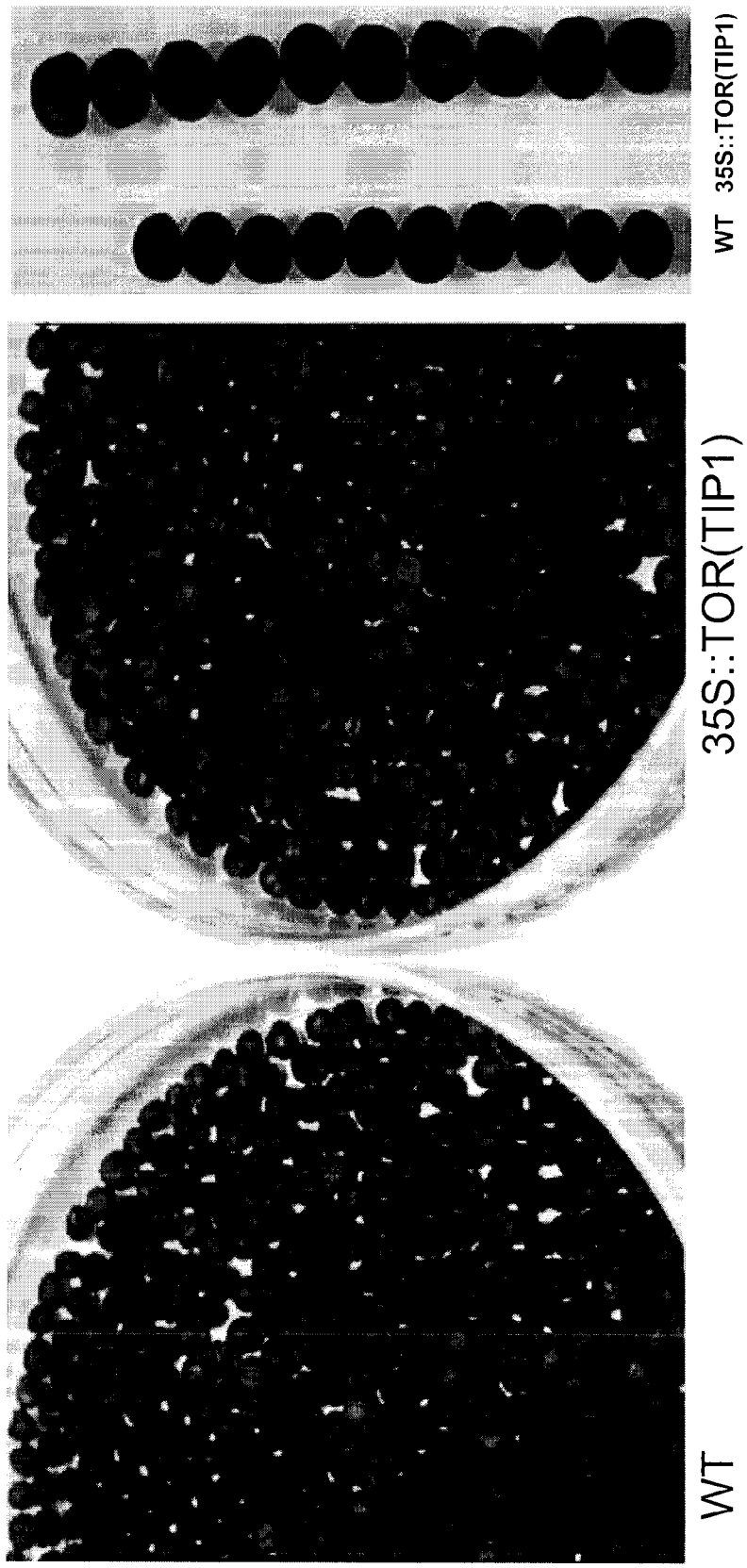

Referring to FIGS. 11A and 11B, the color and size of seed from wild-type (WT) *B. napus* was compared to the color and size of seeds from transgenic BnTIP *B. napus* lines. In BnTIP16 lines, BnTIP16 is over-expressed under the control of the CaMV 35S promoter and in TIP1 (TOR) lines, BnTIP1 (TOR) is over-expressed under the control of the CaMV35S promoter. BnTIP16 encodes a putative serine decarboxylase. Seeds from BnTIP16 transgenic plants are lighter in color than seeds from the wild-type line indicating a reduction in proanthocyanidins (PA) in the seeds of the BnTIP16 line. Seeds from BnTIP1 (TOR) transgenic plants are larger in size than seeds from the wild-type line.

Figure 11C:
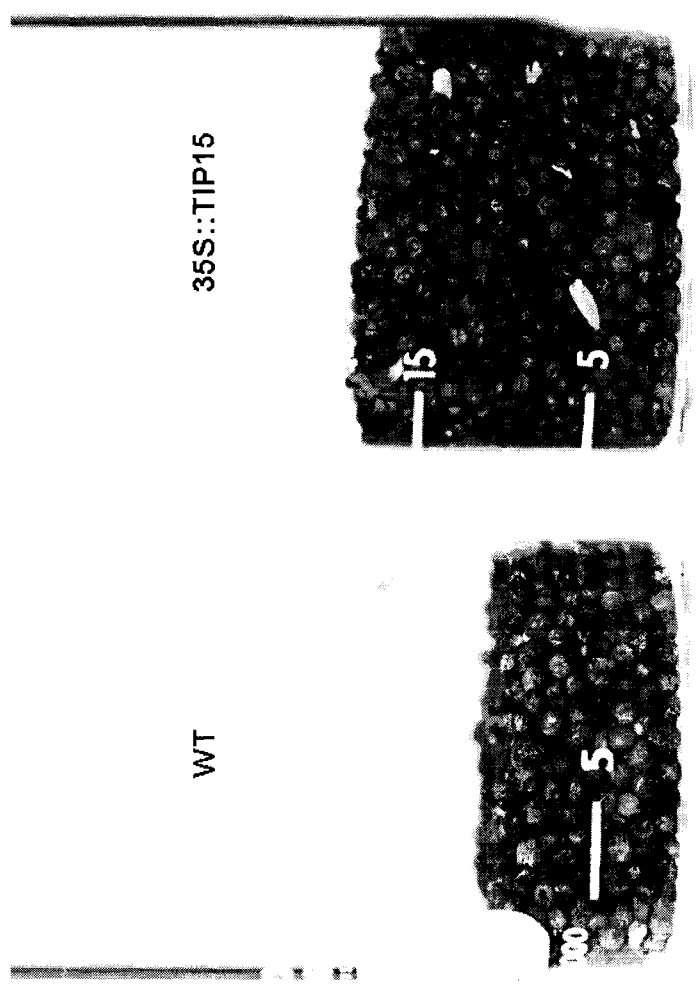

TIP15 encodes a putative transducin family protein. This protein contains WD-40 repeats. Referring to FIG. 11C, over-expression constructs of BnTIP15 under the control of the CaMV35S promoter in transgenic *B. napus* produced plants having about 15% more seeds per plant.

TIP8 encodes a putative 14-3-3 anchor protein. Referring to FIG. 9A and FIG. 9E, over-expression of TIP8 in *Arabidopsis* under the control of the CaMV35S promoter produced plants having increased seed size.

TIP28 shows homology to translation Initiation Factor 2 beta subunit (EIF-2 Beta). Referring to FIG. 9, in *Arabidopsis*, the over-expression of TIP28 under the control of CaMV 35S promoter produced more seeds in siliques.

Oil Content

TIP16 encodes a putative serine decarboxylase. TIP28 shows homology to translation Initiation Factor 2 beta subunit (EIF-2 Beta). In *Arabidopsis*, the over-expression of TIP16 or TIP28 under the control of CaMV 35S promoter increased oil content.

Example 6

Expression of BnTOR

Figure 12A:
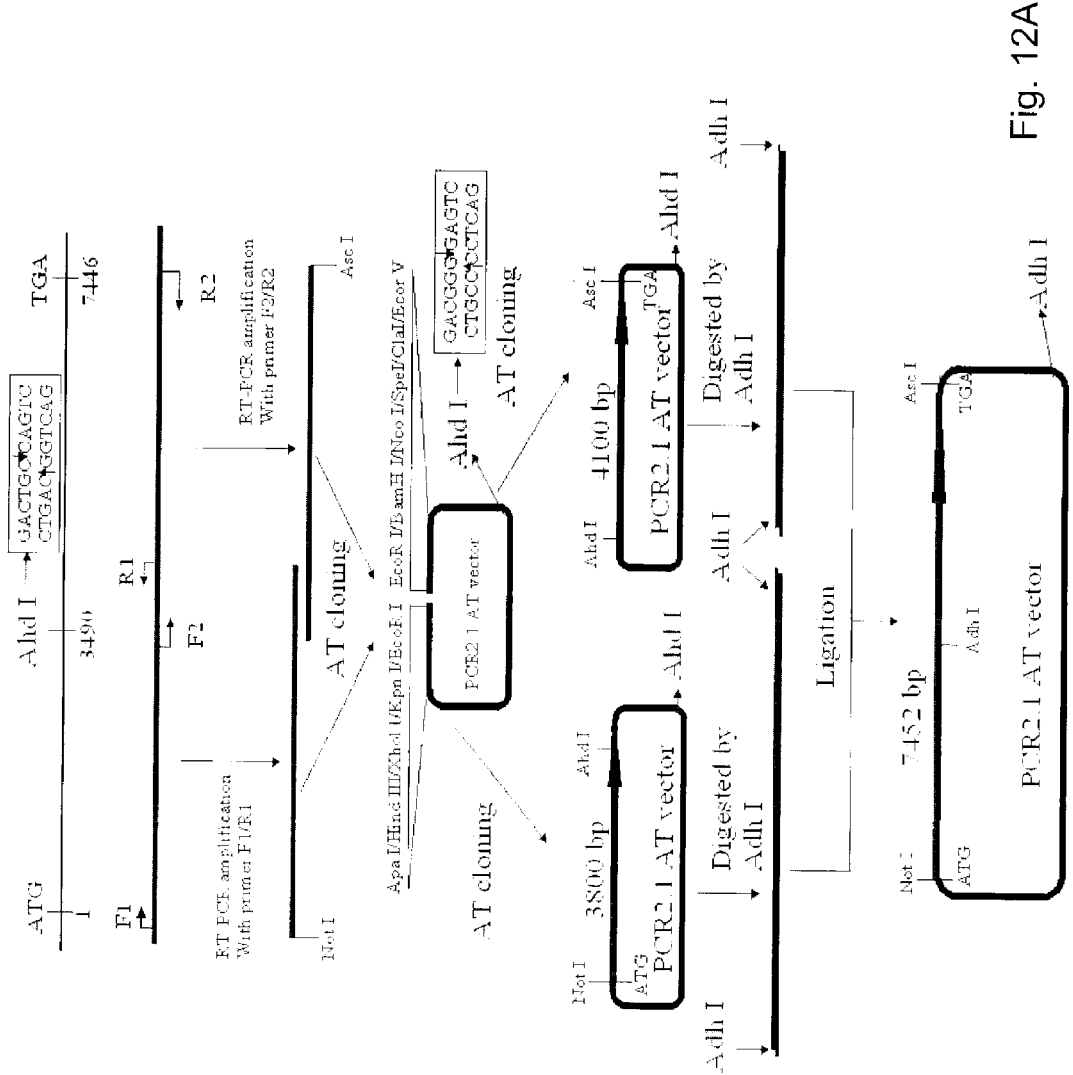
FIG. 12A depicts a flow chart illustrating isolation of TOR from *Brassica napus*.
Figure 12B:
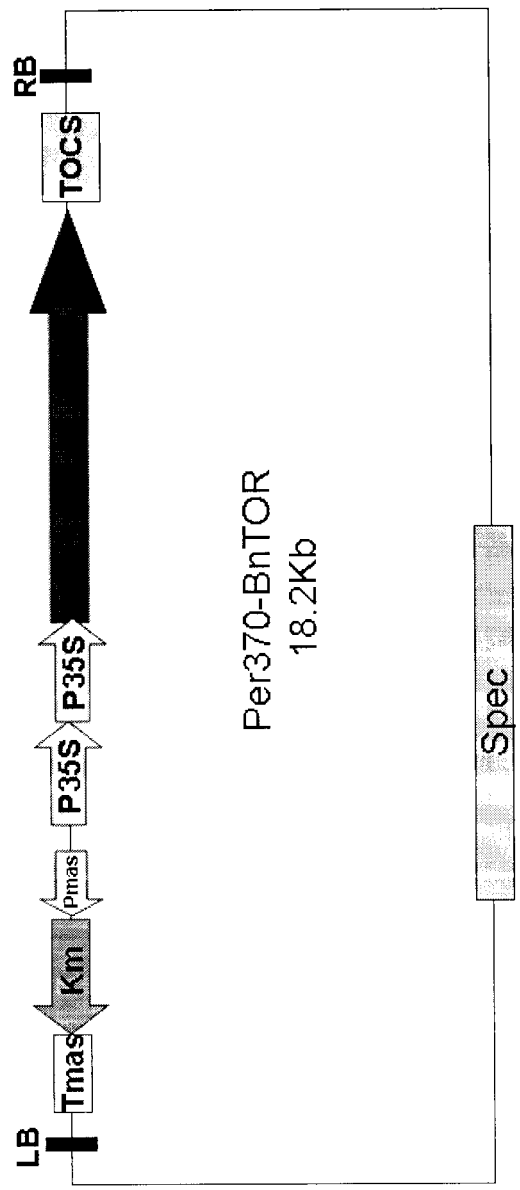
FIG. 12B depicts a map of a BnTOR over-expression construct.
Figure 12C:
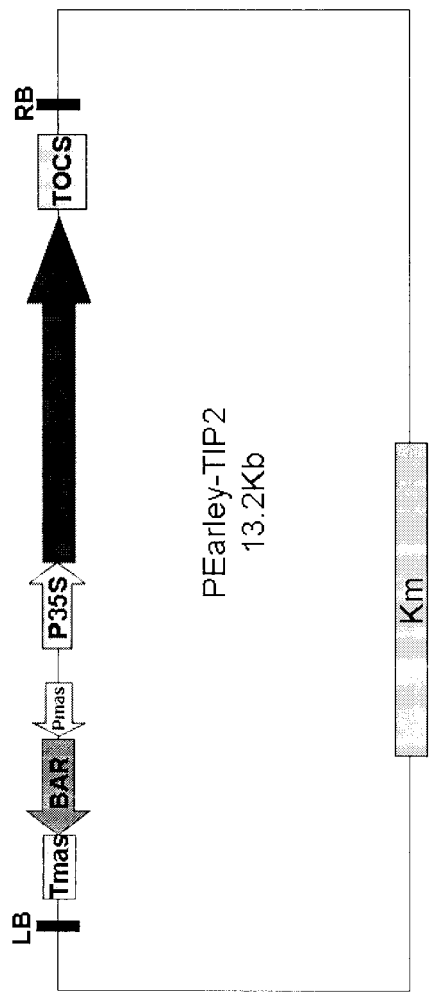
FIG. 12C depicts a map of a TIPs over-expression construct.

Referring to FIG. 12A, full length BnTOR was isolated from *B. napus* as follows. Partial cDNA clones corresponding to putative *B. napus* TOR gene was identified from embryo EST collection. Using this sequence information, RACE™ (rapid amplification of cDNA ends) kit (Invitrogen, Cat. No L1502-01) was employed for identification of BnTOR 5' and two overlapping RT-PCR reactions and sequencing of the products. The BnTOR generated from PCR amplification of two overlapping fragments that contains Not I restriction site at the 5' end and Asc I restriction site at the 3' end. The sequence of this clone was further confirmed by DNA sequencing. BnTOR shows 92% identity at the nucleotide level, and 93% identity at the amino acid level with AtTOR, respectively. The BnTOR was digested with Not I and Asc I restriction enzymes and cloned into Per380 plasmid vector to generate the gateway Entry vector system as further described below. The plant expression construct was generated by transferring BnTOR to destination vector Per370 to produce expression cassette that include double CaMV35S promoter to drive the expression of BnTOR transgene through LR recombination reactions. The details of BnTOR isolation and construction of recombinant expression cassette was described in the FIG. 12A. BnTOR is a 7443 bp DNA molecule (SEQ ID NO: 2) encoding a 2480 aa polypeptide (SEQ ID NO: 4).

Plant expression constructs were generated using the full length and different deletion derivatives of TOR to Per370 vector through LR recombination reactions. The resulting plasmids were used to transform wild-type *Arabidopsis* plants (Col) by the floral dipping method (Clough 1998) and *Brassica napus* by a method using cotyledonary petioles (Moloney 1989).

Figure 13:
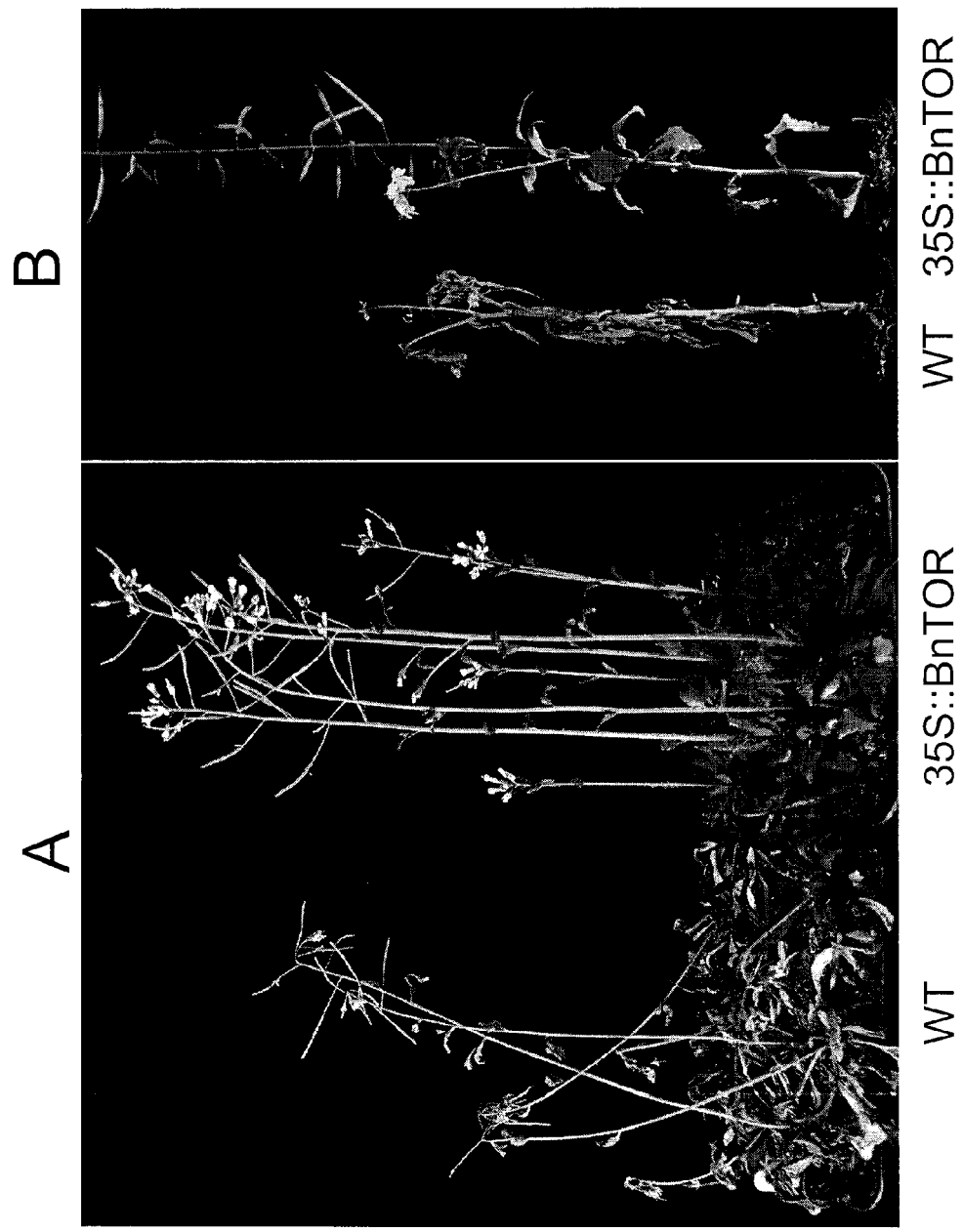
FIG. 13 depicts that ectopic expression of BnTOR confers better water use-efficiency in *Arabidopsis* (FIG. 13A) and *Brassica napus* (FIG. 13B) transgenic lines in a competitive environment.

Referring to FIG. 13. *Arabidopsis* lines with ectopic TOR over-expression showed better water utilization when compared to wild type plants. The transformed lines withstood lack of watering for a period of three weeks, while in comparison the control wild type plants (without the TOR transgene) did not survive and showed wilting (FIG. 13A). Similar results were obtained with transgenic *B. napus*, which exhibited resistance to no water for 10 days longer than wild type (FIG. 13B). In transgenic *Arabidopsis* and *B. napus* transgenic lines, normal growth was restored after watering, whereas the wild type plants did not recover. The results demonstrate that TOR over-expression or targeted expression in transgenic lines provides protection from limited water supply or drought.

Figure 14A:
FIG. 14 depicts that ectopic expression of BnTOR confers 10-15 days earlier flowering in a field (FIG. 14A) and in a greenhouse (FIG. 14B).
Figure 14B:
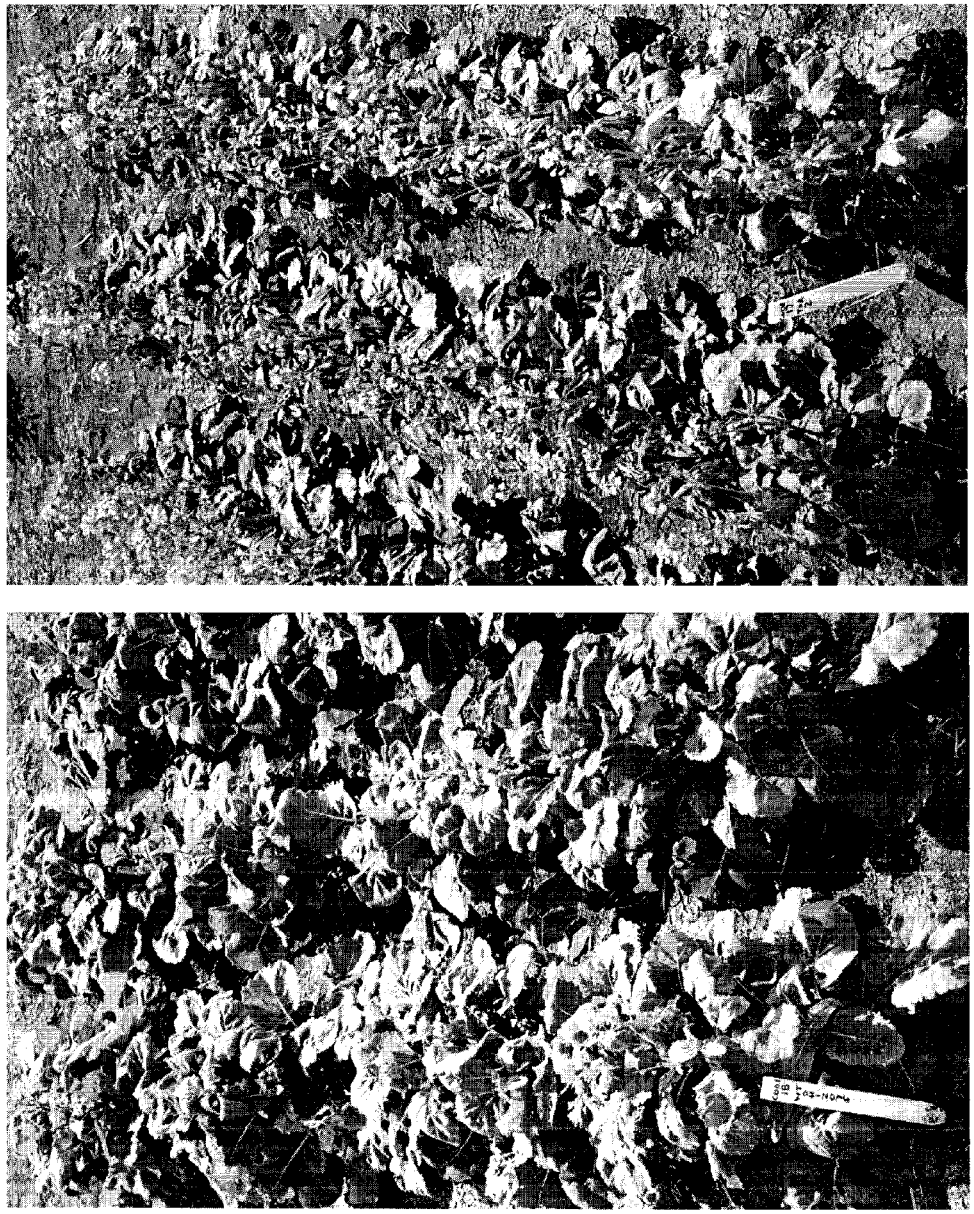

Referring to FIG. 14, transgenic *B. napus* lines with TOR over-expression displayed early flowering by 10-15 days in comparison to the wild type. The overall yield of these plants is not compromised and similar to the wild type. Homozygous *B. napus* lines that displayed this phenotype in greenhouse conditions (FIG. 14B) were tested in field conditions (FIG. 14A) and early flowering was observed. The results in the field (tested in 2008 and 2009) are consistent with the greenhouse. Thus, the growing period for *B. napus* or other crop or economically important crop species can be significantly reduced without compromising the yield.

Figure 15:
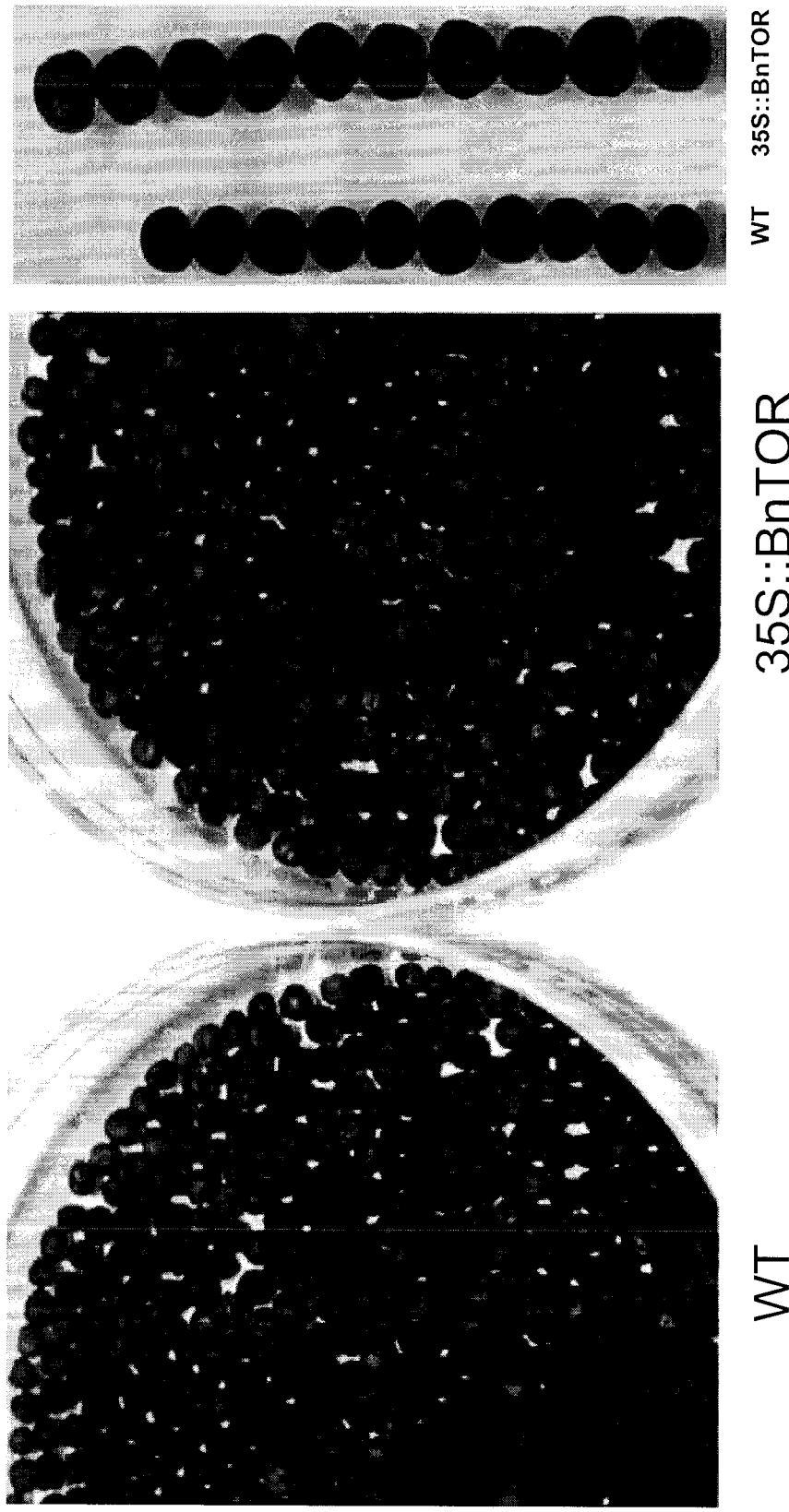
FIG. 15 depicts that ectopic expression of BnTOR confers 15% bigger seeds in *Brassica napus* transgenic lines.

Referring to FIG. 15, transgenic *B. napus* lines with TOR over-expression produced larger and heavier seeds. Seeds from wild type plants had an average seed weight of 0.3745 g per 100 seeds; seeds from BnTOR1 line had an average seed weight of 0.4343 g per 100 seeds; and, seeds from BnTOR2 line had an average seed weight of 0.4296 g per 100 seeds. All measurements were made with 15 repeats. Thus, seeds from the transgenic lines are consistently about 15% larger and heavier than the control wild type seeds. These findings were further tested in field conditions (2008 and 2009) and similar results were obtained. Thus, it is possible to manipulate seed size and weight by expressing, over-expressing or silencing TOR in a plant.

CONCLUSION

The TOR gene signaling pathway is fundamental to the control of growth and development in plants and the transduction of many environmental parameters that modulate plant growth and development. Experimental tools that include biochemical, molecular, developmental, genomic and loss and gain of function transgenic approaches have been applied to modulate the TOR signaling pathway in plants, using *Arabidopsis* model systems and *Brassica napus* crop species. A total of 30 proteins that interact with TOR (TIPs) have been identified and their functions are implicated in diverse developmental and biochemical processes have been investigated. Functional studies with selected gene targets have shown a range of commercially valuable phenotypes that include: reduced flowering time, improved nutrition-use-efficiency, improved water-use-efficiency, improved yield and enhanced stress tolerance in transgenic *Arabidopsis* and *Brassica* lines.

Listing of TOR and TIPs Sequences:
SEQ ID NO: 1—AtTOR (AtTIP1), nucleic acid molecule, 7446 bp, *Arabidopsis thaliana*
SEQ ID NO: 2—AtTOR (AtTIP1), protein, 2481 aa, *Arabidopsis thaliana*
SEQ ID NO: 3—BnTOR (BnTIP1), nucleic acid molecule, 7443 bp, *Brassica napus*
SEQ ID NO: 4—BnTOR (BnTIP1), protein, 2480 aa, *Brassica napus*
SEQ ID NO: 5—AtTIP2, nucleic acid molecule, 1416 bp. *Arabidopsis thaliana*
SEQ ID NO: 6—AtTIP2, protein, 471 aa, *Arabidopsis thaliana*
SEQ ID NO: 7—BnTIP2, nucleic acid molecule, 1389 bp, *Brassica napus*
SEQ ID NO: 8—BnTIP2, protein, 462 aa, *Brassica napus*
SEQ ID NO: 9—AtTIP3, nucleic acid molecule, 873 bp, *Arabidopsis thaliana*
SEQ ID NO: 10—AtTIP3, protein, 290 aa, *Arabidopsis thaliana*
SEQ ID NO: 11—BnTIP3, nucleic acid molecule, 873 bp, *Brassica napus*
SEQ ID NO: 12—BnTIP3, protein, 290 aa, *Brassica napus*
SEQ ID NO: 13—AtTIP5, nucleic acid molecule, 1035 bp. *Arabidopsis thaliana*
SEQ ID NO: 14—AtTIP5, protein, 344 aa, *Arabidopsis thaliana*
SEQ ID NO: 15—BnTIP5, nucleic acid molecule, 1035 bp, *Brassica napus*
SEQ ID NO: 16—BnTIP5, protein, 344 aa. *Brassica napus*
SEQ ID NO: 17—AtTIP6, nucleic acid molecule, 1476 bp. *Arabidopsis thaliana*
SEQ ID NO: 18—AtTIP6, protein, 491 aa. *Arabidopsis thaliana*
SEQ ID NO: 19—BnTIP6, nucleic acid molecule, 1471 bp, *Brassica napus*
SEQ ID NO: 20—BnTIP6, protein, 490 aa, *Brassica napus*
SEQ ID NO: 21—AtTIP7, nucleic acid molecule, 954 bp, *Arabidopsis thaliana*
SEQ ID NO: 22—AtTIP7, protein, 317 aa, *Arabidopsis thaliana*
SEQ ID NO: 23—AtTIP8, nucleic acid molecule, 768 bp. *Arabidopsis thaliana*
SEQ ID NO: 24—AtTIP8, protein, 255 aa. *Arabidopsis thaliana*
SEQ ID NO: 25—BnTIP8, nucleic acid molecule, 774 bp, *Brassica napus*
SEQ ID NO: 26—BnTIP8, protein, 257 aa, *Brassica napus*
SEQ ID NO: 27—AtTIP9, nucleic acid molecule, 1218 bp, *Arabidopsis thaliana*
SEQ ID NO: 28—AtTIP9, protein, 405 aa, *Arabidopsis thaliana*
SEQ ID NO: 29—BnTIP9, nucleic acid molecule, 1218 bp, *Brassica napus*
SEQ ID NO: 30—BnTIP9, protein, 405 aa, *Brassica napus*
SEQ ID NO: 31—AtTIP13, nucleic acid molecule, 4035 bp, *Arabidopsis thaliana*
SEQ ID NO: 32—AtTIP13, protein, 1344 aa, *Arabidopsis thaliana*
SEQ ID NO: 33—AtTIP15, nucleic acid molecule, 2262 bp, *Arabidopsis thaliana*
SEQ ID NO: 34—AtTIP15, protein, 753 aa, *Arabidopsis thaliana*
SEQ ID NO: 35—BnTIP15, nucleic acid molecule, 2205 bp, *Brassica napus*
SEQ ID NO: 36—BnTIP15, protein, 734 aa. *Brassica napus*
SEQ ID NO: 37—AtTIP16, nucleic acid molecule, 1449 bp, *Arabidopsis thaliana*
SEQ ID NO: 38—AtTIP16, protein, 482 aa, *Arabidopsis thaliana*
SEQ ID NO: 39—AtTIP28, nucleic acid molecule, 807 bp. *Arabidopsis thaliana*
SEQ ID NO: 40—AtTIP28, protein, 268 aa, *Arabidopsis thaliana*
SEQ ID NO: 41—BnTIP28, nucleic acid molecule, 819 bp. *Brassica napus*
SEQ ID NO: 42—BnTIP28, protein, 272 aa. *Brassica napus*
SEQ ID NO: 78—BnTIP16, nucleic acid molecule, 1473 bp, *Brassica napus*
SEQ ID NO: 79—BnTIP16, protein, 490 aa. *Brassica napus*

REFERENCES

The contents of the entirety of each of which are incorporated by this reference.

Alvarez J P, Pekker I, Goldshmidt A, Blum E. Amsellem Z, Eshed Y (2006) Endogenous and synthetic microRNAs stimulate simultaneous, efficient, and localized regulation of multiple targets in diverse species. *Plant Cell*. 8: 1134-51.

Andrade M A, Bork P (1995) HEAT repeats in the Huntington's disease protein. *Nat Genet*. October; 11(2):115-6.

Barbet N C, Schneider U, Helliwell S B, Stansfield I, Tuite M F, Hall M N (1996) TOR controls translation initiation and early G1 progression in yeast. *Mol Biol Cell*. January; 7(1):25-42.

Bechtold N, Ellis J, Pellefer G (1993) In planta *Agrobacterium*-mediated gene transfer by infiltration of adult *Arabidopsis thaliana* plants. *C.R. Acad. Sci. Ser. III Sci. Vie*. 316: 1194-1199.

Becker D, Brettschneider R, Lorz H. (1994) Fertile transgenic wheat from microprojectile bombardment of scutellar tissue. *Plant J*. 5: 299-307.

Bla'zquez M A, Soowal L, Lee I, Weigel D (1997) LEAFY expression and flower initiation in *Arabidopsis*. *Development* 124, 3835-3844.

Bosotti R, Isacchi A, Sonnhammer E L (2000) FAT: a novel domain in PIK-related kinases. *Trends Biochem Sci.* May; 25(5):225-7.

Clough S J., Bent A (1998) Floral dip: a simplified method for *Agrobacterium*-mediated transformation of *Arabidopsis thaliana. Plant J.* 16:735-743.

Datla R S, Hammerlindl J K, Panchuk B. Pelcher L E, Keller W (1992) Modified binary plant transformation vectors with the wild-type gene encoding NPTII. *Gene.* 122, 383-384.

Datla R, Anderson J W, Selvaraj G (1997) Plant promoters for transgene expression. *Biotechnology Annual Review.* 3: 269-296.

De Virgilio C, Loewith R (2006) Cell growth control: little eukaryotes make big contributions. *Oncogene.* 25: 6392-6415.

DeBlock M. DeBrouwer D, Tenning P (1989) Transformation of *Brassica napus* and *Brassica oleracea* using *Agrobacterium tumefaciens* and the expression of the bar and neo genes in the transgenic plants. *Plant Physiol.* 91: 694-701.

Dellaporta S J, Wood J, Hicks J B (1983) A plant DNA minipreparation: Version II. *Plant Mol. Biol. Reporter.* 1: 19-21.

Depicker A, Montagu M V (1997) Post-transcriptional gene silencing in plants. *Curr Opin Cell Biol.* 9: 373-82.

Deprost D, Yao L, Sormani R, Moreau M, Leterreux G, Nicolai M, Bedu M, Robaglia C, Meyer C (2007) The *Arabidopsis* TOR kinase links plant growth, yield, stress resistance and mRNA translation. *EMBO Reports* 8: 864-870

Gangloff Y G, Mueller M, Dann S G, Svoboda P, Sticker M, Spetz J F, Um S H, Brown E J, Cereghini S, Thomas G, Kozma S C (2004) Disruption of the mouse mTOR gene leads to early postimplantation lethality and prohibits embryonic stem cell development. *Mol Cell Biol.* N.

Helliwell C A, Waterhouse P M (2005) Constructs and methods for hairpin RNA-mediated gene silencing in plants. *Methods Enzymology* 392: 24-35.

Henikoff S, Till B J, Comai L (2004) TILLING. Traditional mutagenesis meets functional genomics. *Plant Physiol.* 135: 630-6.

Hirayama T, Ohto C, Mizoguchi T, Shinozaki K (1995) A gene encoding a phosphatidylinositol-specific phospholipase C is induced by dehydration and salt stress in *Arabidopsis thaliana. Proc. Natl. Acad. Sci. USA.* 92: 3903-3907.

Inoki K. Guan K L (2006). Complexity of the TOR signaling network. *Trends Cell Biol.* 2006 April; 16(4):206-12. Epub March 3.

Katavic Y, Haughn G W. Reed D. Martin M, Kunst L (1994) In planta transformation of *Arabidopsis thaliana. Mol. Gen. Genet.* 245: 363-370

Kim Y J, Kim J E, Lee J H, Lee M H. Jung H W. Bahk Y Y. Hwang B K. Hwang I, Kim W T (2004) The Vr-PLC3 gene encodes a putative plasma membrane-localized phosphoinositide-specific phospholipase C whose expression is induced by abiotic stress in mung bean (*Vigna radiata* L.). *FEBS Lett.* 556: 127-136

Kunz J, Schneider U, Howald I. Schmidt A, Hall M N (2000) HEAT repeats mediate plasma membrane localization of Tor2p in yeast. *J Biol Chem.* November 24; 275(47):37011-20.

Li X, Song Y. Century K. Straight S, Ronald P, Dong X, Lassner M, Zhang Y (2001) A fast neutron deletion mutagenesis-based reverse genetics system for plants. *Plant J.* 27: 235-242.

Loewith R, Jacinto E, Wullschleger S. Lorberg A, Crespo J L, Bonenfant D. Oppliger W. Jenoe P, Hall M N (2002) Two TOR complexes, only one of which is rapamycin sensitive, have distinct roles in cell growth control. *Mol Cell.* September:10(3):457-68.

Mahfouz M M. Kim S, Delauney A J, Verma DPS (2006) *Arabidopsis* TARGET of RAPAMYCIN interacts with RAPTOR which regulates the activity of S6 kinase in response to osmotic stress. *The Plant Cell.* 18: 477-490.

Martin D E, Hall M N (2005) *Current Opinion in Cell Biology.* 17:158-166.

Menand B, Desnos T, Nussaume L. Berger F. Bouchez D, Meyer C, Robaglia C (2002) Expression and disruption of the *Arabidopsis* TOR (target of rapamycin) gene. *PNAS.* 99: 6422-6427.

Meyer P (1995) Understanding and controlling transgene expression. *Trends in Biotechnology.* 13: 332-337.

Moloney M M, Walker J M, Sharma K K (1989;) High efficiency transformation of *Brassica napus* using *Agrobacterium* vectors. *Plant Cell Rep* 8: 238-242.

Munnik T. (1999) Phosphatidic acid: an emerging plant lipid second messenger. *Trends in Plant Sci.* 6: 227-233.

Murakami M, Ichisaka T, Maeda M, Oshiro N. Hara K, Edenhofer F, Kiyama H, Yonezawa K, Yamanaka S (2004) mTOR is essential for growth and proliferation in early mouse embryos and embryonic stem cells. *Mol Cell Biol.* August; 24(15):6710-8

Neddleman and Wunsch (1970) *J. Mol. Biol.* 48: 443.

Nehra N S, Chibbar R N. Leung N. Caswell K, Mallard C. Steinhauer L, Baga M. Kartha K K (1994) Self-fertile transgenic wheat plants regenerated from isolated scutellar tissues following microprojectile bombardment with two distinct gene constructs. *Plant J.* 5: 285

Pearson and Lipman (1988) *Proc. Natl. Acad. Sci. (U.S.A.).* 85: 2444.

Potrykus L (1991) Gene transfer to plants: Assessment of publish approaches and results. *Annu. Rev. Plant Physiol. Plant Mol. Biol.* 42: 205-225.

Pouwels et al (1986) *Cloning Vectors.* A laboratory manual, Elsevier, Amsterdam.

Powers T, Walter P (1999) Regulation of ribosome biogenesis by the rapamycin-sensitive TOR-signaling pathway in *Saccharomyces cerevisiae. Mol Biol Cell.* April:10(4):987-1000.

Rhodes C A, Pierce D A, Mettler I J, Mascarenhas D, Detmer J J (1988) Genetically transformed maize plants from protoplasts. *Science.* 240: 204-207.

Sambrook J, Fritsch E F, Maniatis T (1989) *Molecular Cloning: A Laboratory Manual $2^{nd}$ edn.* Cold Spring Harbor: Cold Spring Harbor Laboratory Press.

Sambrook J, Fritsch E F, Maniatis T (2001) *Molecular Cloning: A Laboratory Manual $3^{rd}$ edn.* Cold Spring Harbor: Cold Spring Harbor Laboratory Press.

Sanford J C, Klein T M. Wolf E D, Allen N (1987) Delivery of substances into cells and tissues using a particle bombardment process. *J. Part. Sci. Technol.* 5: 27-37.

Schwab R, Ossowski S, Riester M, Warthmann N, Weigel D (2006) Highly specific gene silencing by artificial microRNAs in *Arabidopsis. Plant Cell.* 18: 1121-33.

Shimamoto K, Terada R, Izawa T. Fujimoto H (1989) Fertile transgenic rice plants regenerated from transformed protoplasts. *Nature.* 335: 274-276.

Smith and Waterman. (1981) *Ad. App. Math.* 2: 482.

Songstad D D. Somers D A, Griesbach R J (1995) Advances in alternative DNA delivery techniques. *Plant Cell, Tissue and Organ Culture.* 40: 1-15

Stam M, de Bruin R, van Blokland R, van der Hoorn R A, Mol J N, Kooter J M (2000) Distinct features of post-transcriptional gene silencing by antisense transgenes in single copy and inverted T-DNA repeat loci. *Plant J.* 21: 27-42.

Vasil I K (1994) Molecular improvement of cereals. *Plant Mol. Biol.* 5: 925-937.

Vergnolle C. Vaultier M-N. Taconnat L. Renou J-P. Kader J-C. Zachowski A, Ruelland E (2005) The Cold-Induced Early Activation of Phospholipase C and D Pathways Determines the Response of Two Distinct Clusters of Genes in *Arabidopsis* Cell Suspensions. *Plant Physiol.* 139: 1217-1233.

Walden R, Wingender R (1995) Gene-transfer and plant regeneration techniques. *Trends in Biotechnology.* 13: 324-331

Warner J R, Vilardell J, Sohn J H (2001) Economics of ribosome biosynthesis. *Cold Spring Harb Symp Quant Biol.* 66:567-74.

Weisman R. Choder M (2001) The fission yeast TOR homolog, tor1+, is required for the response to starvation and other stresses via a conserved serine. *J Biol Chem.* March 9:276(10):7027-32. Epub 2000 Nov. 28.

Wullschleger S, Loewith R, Hall M N (2006) TOR signaling in growth and metabolism. *Cell.* February 10; 124(3):471-84.

Young K (1998) Yeast two-hybrid: so many interactions, (in) so little time. *Biol Reprod.* 58 (2): 302-11.

Zhang J. Xiao1 Q. Li K, Chen M. Chang J, Luo L. Li Y, Liu Y. Shewry P R, He G. (2006) An optimal pooling strategy applied to high-throughput screening for rare marker-free transformants. *Biotechnology Letters.* 28(19):1537-1544.

Zheng X F, Florentino D, Chen J. Crabtree G R, Schreiber S L (1995) TOR kinase domains are required for two distinct functions, only one of which is inhibited by rapamycin. *Cell.* July 14; 82(1):121-30.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A method of altering a phenotype in a plant, said method comprising: introducing into the plant a nucleic acid molecule comprising
the nucleotide sequence as set forth in SEQ ID NO: 7 or a codon degenerate nucleotide sequence thereof,
said nucleic acid molecule encoding a target of rapamycin (TOR) interacting protein which interacts with a TOR protein under conditions whereby the nucleic acid molecule is over-expressed thereby altering the phenotype, wherein the altered phenotype comprises increased nutrient-use-efficiency compared to a wild-type plant grown under the same conditions.

2. The method according to claim 1, wherein the increased nutrient-use-efficiency comprises at least one of increased nitrogen-use-efficiency or increased potassium-use-efficiency.

3. The method according to claim 1, wherein the TOR interacting protein comprises: (i) the amino acid sequence as set forth in SEQ ID NO: 8.

4. The method according to claim 1, wherein the plant is *Arabidopsis thaliana*, *Brassica* spp., *Borago* spp., *Ricinus* spp., *Theobroma* spp., *Zea* spp., *Gossypium* spp., *Crambe* spp., *Cuphea* spp., *Linum* spp., *Lesquerella* spp., *Limnanthes* spp., *Linola* spp., *Tropaeolum* spp., *Oenothera* spp., *Olea* spp., *Elaeis* spp., *Arachis* spp., *Carthamus* spp., *Glycine* spp., *Soja* spp., *Helianthus* spp., *Nicotiana* spp. *Vernonia* spp., *Triticum* spp., *Hordeum* spp., *Oryza* spp., *Avena* spp., *Sorghum* spp., *Secale* spp., *Medicago sativa*, *Lens culinaris* or *Cicer arietinum*.

5. The method according to claim 4, wherein the plant is *A. thaliana*, *B. napus*, *B. oleracea*, *B. rapa*, *B. carinata* or *B. juncea*.

6. An isolated or purified polypeptide comprising the amino acid sequence as set forth in SEQ ID NO: 8.

7. An isolated or purified nucleic acid molecule comprising the nucleotide sequence as set forth in SEQ ID NO: 7 or a codon degenerate nucleotide sequence thereof said nucleic acid molecule encoding a target of rapamycin (TOR) interacting protein.

8. A plant cell, plant seed or plant having introduced therein a nucleic acid molecule comprising the nucleotide sequence as set forth in SEQ ID NO: 7 or a codon degenerate nucleotide sequence thereof, said nucleotide molecule encoding a TOR interacting protein which interacts with a TOR protein, expression of the nucleic acid molecule altering growth and development of the cell, seed or plant in comparison to a cell, seed or plant in which the nucleic acid molecule is not introduced.

9. The plant cell, seed or plant according to claim 8 which is *Arabidopsis thaliana*, *Brassica* spp., *Borago* spp., *Ricinus* spp., *Theobroma* spp., *Zea* spp., *Gossypium* spp., *Crambe* spp., *Cuphea* spp., *Linum* spp., *Lesquerella* spp., *Limnanthes* spp., *Linola* spp., *Tropaeolum* spp., *Oenothera* spp., *Olea* spp., *Elaeis* spp., *Arachis* spp., *Carthamus* spp., *Glycine* spp., *Soja* spp., *Helianthus* spp., *Nicotiana* spp. *Vernonia* spp., *Triticum* spp., *Hordeum* spp., *Oryza* spp., *Avena* spp., *Sorghum* spp., *Secale* spp., *Medicago sativa*, *Lens culinaris* or *Cicer arietinum*.

10. The plant cell, seed or plant according to claim 9 which is *A. thaliana*, *B. napus*, *B. oleracea*, *B. rapa*, *B. carinata* or *B. juncea*.

* * * * *

SEQUENCE LISTING

```
<160> NUMBER OF SEQ ID NOS: 79

<210> SEQ ID NO 1
<211> LENGTH: 7446
<212> TYPE: DNA
<213> ORGANISM: Arabidopsis thaliana

<400> SEQUENCE: 1
atgtctacct cgtcgcaatc ttttgtggct ggacggcctg catccatggc ttcccctttcg      60 caatcgcacc gcttttgtgg tccctcagcc accgcttctg gtggcggaag ctttgacact     120
ttgaatcgtg tcatcgctga cctttgcagc cgtggtaatc ctaaggaggg agctcctttta    180 gcgtttagga aacacgtaga ggaagcagtt cgtgatctta gtggtgaagc ttcctctagg     240
ttcatggagc aattatatga caggattgct aatttaattg agagcactga tgtggcggaa     300
aacatgggtg cactcagagc cattgatgag ttgacggaga ttggatttgg tgagaatgct     360
actaaggttt ctagatttgc gggttacatg aggactgtgt tcgagttgaa gcgtgatcct     420
gaaatcttgg tgcttgctag tagagttttg gggcaccttg ctcgggcagg tggagcaatg     480
acttctgatg aagtggagtt tcagatgaaa acagcttttg attggcttcg cgtagacagg     540
gtggaatatc gtcgtttcgc cgccgtttta atattaaagg agatggccga aaatgcttct     600
actgtcttta acgttcatgt ccctgaattt gtggatgcta tctgggttgc acttagggac     660
ccccagttgc aagtgcgaga acgagctgtt gaagctttgc gtgcatgcct tcgtgttatt     720
gagaaagggg agactcgatg gcgagtgcag tggtactatc gaatgtttga agctacacag     780
gatgggttgg gcagaaatgc tccggttcac agtattcatg gttctttact tgccgtgggg     840
gagctgttga ggaatacagg tgagttcatg atgtctaggt atagagaagt tgccgaaatt     900
gtcctcagat accttgaaca tcgtgatcgc cttgttcgcc ttagcatcac ctcgttactg     960
cctcgcattg ctcactttct ccgtgaccgg tttgtgacaa actatttaac gatatgcatg    1020
aatcatattc ttactgtgtt aagaataccg gctgaaagag ccagtgggtt catcgccctt    1080
ggggaaatgg ctggtgcttt ggatggtgag cttatccatt atttgccgac aattatgtct    1140
catctgcggg atgcgattgc tccacgtaaa ggcagacctt tgcttgaagc tgtggcttgt    1200
gttggtaaca tcgcaaaggc aatgggatcc acagtggaaa ctcatgttcg agatctttta    1260
```

```
gatgttatgt tttcatctag tctctcttcc acacttgttg acgctcttga ccagataacc    1320
atcagcattc cttctttgct gccaacagta caagatcggc ttctagattg catttcgttg    1380
gttcttccaa aatcccatta ttctcaagca aagcctcctg ttaccattgt ccgaggtagt    1440
acagtgggca tggcaccaca gtcttctgac cctagttgtt cagctcaagt tcaactagcc    1500
ctgcagactc ttgctcgttt caatttcaag ggacatgatc ttcttgaatt tgctcgggag    1560
tcagttgttg tttatttgga tgatgaggat gcagccacaa gaaaagatgc tgctttgtgt    1620
tgttgcagac taattgcaaa ttctctttct ggcatcacac aatttggctc gagcaggtca    1680
acacgagcag gggggagacg caggcgcctt gtggaagaga ttgtggaaaa gcttctcagg    1740
acagccgttg cagatgctga tgtaactgtt cgcaaatcta tattcgttgc tttatttggc    1800
aaccaatgtt tcgatgatta tctagcacag gctgatagtt tgactgccat ttttgcttcc    1860
ttaaatgatg aggaccttga tgttcgagaa tatgccatct cagttgctgg aaggttatcg    1920
gaaaaaaatc cagcatacgt acttccagca cttcgtcgcc atcttataca gttgttgacc    1980
tatcttgagc tgagtgcaga taacaagtgc agggaagaga gtgcaaagct ccttggttgt    2040
ttagttcgaa attgtgaacg gctcattctt ccatacgtag cccctgtcca aaaggcactt    2100
gttgcgagac ttagtgaagg aactggagtg aatgctaaca ataatattgt cactggagtt    2160
ctcgtaactt ttggggatct tgcaagagtg ggtggcttgg caatgagaca atatattccg    2220
gagctgatgc ctttaattgt tgaagcttta atggatggag ctgctgtagc aaaacgtgag    2280
gtggctgttt ctactcttgg tcaagttgtt caaagtacag ggtatgttgt gactccatac    2340
aaggaatacc cattgttgct tgggttactc ttgaaattgc tgaagggtga cttagtgtgg    2400
tctaccagac gagaagtgct caaggttctt ggaattatgg gcgctttgga tcctcatgtg    2460
cataaacgta accaacaaag tttatcagga tcacatggtg aagttcctcg cggcactggt    2520
gattctggtc aacctattcc atcaattgat gagttacctg tcgaactccg gccgtcattt    2580
gctacatctg aggattatta ctcaacggtt gctatcaact cgcttatgcg aattcttaga    2640
gatgcatcac ttcttagtta ccacaaaagg gttgttagat ctctgatgat cattttcaag    2700
tcaatgggat tgggatgcgt gccttacttg ccgaaggttt tacctgagct tttttcacact    2760 gttcgaacat ctgatgagaa cctgaaggac ttcattacgt ggggtcttgg gactcttgtt    2820
tccattgttc gccagcacat acgcaagtat ctgccagagc tgctttcatt agtctctgaa    2880
ctatggtcat ccttcacctt gcccggtccc atacgcccat cacgtggtct tccggttctg    2940
catctactgg aacatctttg cttggcactt aatgatgaat tcagaactta tcttccagtc    3000
atccttccat gtttcatcca agtattaggt gacgccgagc ggtttaatga ttacaccctat    3060 gttcctgata ttctccacac actcgaagtg tttggcggaa ctcttgatga gcacatgcat    3120
ttactccttc cggcacttat tcgattgttt aaagtagatg ctcctgtagc tataagacgc    3180
gatgccatca aaactttgac aagagtaatc ccgtgtgttc aggttactgg tcatatctcc    3240
gctctcgtgc atcacttgaa gctagtatta gatgggaaga atgatgagtt gcggaaagat    3300
gctgtcgatg cactatgctg tttggctcat gcacttggag aggacttcac catattcatt    3360
gaatcaattc acaagctttt attgaagcat cgattgcggc ataaagaatt tgaggaaatt    3420
catgctcgct ggcggagacg tgaaccattg attgtagcta caactgcaac ccaacaatta    3480
agtaggcgac tgccagttga ggttatcagg atcctgtaa ttgagaatga atcgatcct    3540 ttcgaagaag gaactgacag aaaccatcag gttaatgatg gtagactacg acagctgga    3600 gaagcttctc aacgcagcac caaagaagat tgggaggaat ggatgagaca ttttagtatt    3660
```

```
gaattactta aggagtctcc ctctccagca ttaagaactt gtgcaaaact tgctcagttg    3720
cagccatttg tcgggagaga gttgtttgct gctggctttg tcagttgctg ggcacagcta    3780
aacgagtcta gccaaaagca gttagttagg agcttggaaa tggccttttc atctccaaat    3840
atccctccag aaattttagc tacactactc aatttggcag agtttatgga acatgatgag    3900
aagcctcttc ccattgatat tcgtcttctg ggggctcttg ctgaaaagtg ccgtgttttt    3960
gccaaagctc tgcattataa agagatggaa tttgaaggtc cacgatccaa gaggatggat    4020
gccaacccag ttgctgttgt cgaggctctt atacacataa ataatcagtt acaccagcat    4080
gaggctgctg tcggtatact aacctatgct caacaacatc ttgatgtgca attaaaagaa    4140
tcatggtatg agaagctgca cgctgggac gatgcactca aggcgtacac tttgaaagca     4200
tctcaaacaa caaatcctca tcttgtatta gaagccacat taggacaaat gagatgtctt    4260
gctgcacttg cacgatggga agagctcaac aatctctgca aagagtactg gagtcctgct    4320
gagccatctg cgcgtctgga aatggcacca atggctgcac aagctgcatg gaacatggga    4380
gagtgggatc aaatggccga atatgtgtct cggctagatg atggtgatga acaaagctt     4440 cggggtttag caagcccggt ttctagtggc gatgggagca gtaatggcac attcttcagg    4500
gctgttctgt tagttcgaag ggcaaagtac gacgaggcac gcgaatatgt ggaaagagct    4560
agaaaatgtc ttgccacaga acttgcagcg ctggttttgg agagctatga gcgtgcgtac    4620
agcaatatgg ttcgtgttca gcagctgtca gaactagagg aggtaattga atattatacg    4680
ctgcctgtgg gaaatactat tgccgaagaa cggagagctc taattcgtaa tatgtggact    4740
cagcggattc agggatctaa gcgtaatgtg gaggtgtggc aagcactttt ggctgtccgg    4800
gcacttgtgc tacctcctac agaagatgtg gaaacttggc tcaagtttgc ctcgcttgt     4860 cgaaagagtg ggaggatcag tcaggcgaaa tctactctac tcaagctctt accgtttgat    4920
ccagaagtat caccagaaaa catgcaatat cacggacctc cacaagtgat gcttggatac    4980
ttaaaatacc aatggtcact tggagaggaa cgtaagcgca agaggcatt taccaagctg     5040 cagattctaa cgagagagct ctcaagtgtg ccacattctc aatctgacat actggctagc    5100
atggtatcta gcaagggcgc aaatgttcca cttcttgcac gtgtaaatct caaactggga    5160
acgtggcagt gggcactttc ttccggtttg aatgatgggt ctattcaaga aattcgtgat    5220
gcgtttgaca atctacttg ctatgctcct aaatgggcta aagcatggca cacatgggca    5280
ttattcaata cagcagtgat gtcgcattac atttcaagag gtcaaattgc ttcccagtac    5340
gttgtttctg cagtcactgg atatttttat tctatagcat gtgcagcaaa tgccaaagga    5400
gttgatgata gtttacagga catactgcgt cttctgacat tgtggttcaa ccatggagct    5460
acagctgatg tccaaaccgc attgaagaca ggattcagtc atgtcaacat taacacatgg    5520
cttgttgtgc tacctcaaat cattgctagg atacattcta ataatcgtgc tgtcagggaa    5580
ctgattcagt ctcttctcat ccgcataggc gaaaaccacc cacaggctct gatgtatccc    5640
cttctcgttg catgtaaatc aataagcaat cttcggagag ctgcggctca gaggtggtt    5700 gataaagttc gccagcacag tggtgcactc gtggatcagg cgcaacttgt atcacatgaa    5760
cttatcaggg ttgccatact ttggcatgaa atgtggcatg aagcactaga agaagctagt    5820
cgcttgtatt ttggtgaaca taacattgaa ggcatgctga agtacttga accccttacat    5880 gacatgctcg acgaaggtgt aaaaaaggac agtacgacca tacaggaaag agcatttata    5940
gaggcatacc gtcacgaact aaaagaggca catgaatgct gttgcaatta caagataact    6000
gggaaagatg ctgaacttac acaggcttgg gatctttact atcacgtttt caaacggatt    6060
```

```
gacaaacagc tagccagtct cacgacattg gatttggaat ctgtttctcc tgagttgctg    6120
ctgtgccgtg acttggagct agcagttcct ggaacatatc gtgcagatgc ccccgtcgtg    6180
actatatcat cttttttcacg ccaacttgtt gttataacct ctaaacaaag accaaggaaa   6240
ttgactattc acggaaatga cggtgaggac tacgccttct tgttgaaggg acatgaagat    6300
ttaaggcaag atgagcgtgt tatgcagctt tttggtttgg tgaacacttt gcttgagaat    6360
tccagaaaaa cagccgaaaa agatctttcc attcaacgct attctgtaat accactatct    6420
cccaatagtg gactcatcgg atgggttccg aactgcgata cccttcacca tcttattcga    6480
gagcacagag atgcaagaaa gatcattctt aatcaagaaa ataagcatat gttgagtttt    6540
gctccagact atgacaatct accgcttata gcaaaggttg aagtatttga gtatgctcta    6600
gaaaacacag agggaaatga tctatccagg gttctctggt taaaaagtcg ctcgtcagaa    6660
gtttggctag aaagaagaac aaactatact agaagtttag cagttatgag tatggttggt    6720
tatattcttg ggttaggtga tcgacaccca agtaaccttaa tgcttcatag atacagtgga    6780
aagatcttgc atattgattt tggagattgt tttgaggctt ctatgaatag agagaagttt    6840
cctgaaaagg ttccattccg cctgacaaga atgcttgtca aagcaatgga agtcagtggc    6900
attgaaggaa acttccgctc aacctgcgaa acgttatgc aagttctcag aaccaataaa     6960
gatagtgtaa tggcaatgat ggaagcgttt gtacatgatc ctttaatcaa ttggcgtctt    7020
ttcaatttca atgaagtccc ccaattagca ctgctcggta acaacaaccc caatgctcct    7080
gctgatgttg agcctgacga agaagatgaa gatcccgctg atatagatct tcctcagcct    7140
caaaggagta ctcgagagaa ggagattctt caggctgtaa atatgcttgg agatgctaat    7200
gaagttttaa atgagcgtgc cgtagttgtt atggcacgta tgagtcataa gcttacaggg    7260 cgtgatttt cttcgtctgc aattccgagc aatcccattg ctgatcataa taacttgctc     7320
ggaggagatt ctcatgaagt cgaacatggt ttgtctgtga agttcaggt tcaaaaacta     7380 atcaatcaag ccacttccca tgagaatctc tgtcaaaact atgttgggtg gtgccctttc   7440
tggtga                                                              7446

<210> SEQ ID NO 2
<211> LENGTH: 2481
<212> TYPE: PRT
<213> ORGANISM: Arabidopsis thaliana

<400> SEQUENCE: 2

Met Ser Thr Ser Ser Gln Ser Phe Val Ala Gly Arg Pro Ala Ser Met
1               5                   10                  15

Ala Ser Pro Ser Gln Ser His Arg Phe Cys Gly Pro Ser Ala Thr Ala
            20                  25                  30

Ser Gly Gly Gly Ser Phe Asp Thr Leu Asn Arg Val Ile Ala Asp Leu
        35                  40                  45

Cys Ser Arg Gly Asn Pro Lys Glu Gly Ala Pro Leu Ala Phe Arg Lys
    50                  55                  60

His Val Glu Glu Ala Val Arg Asp Leu Ser Gly Glu Ala Ser Ser Arg
65                  70                  75                  80

Phe Met Glu Gln Leu Tyr Asp Arg Ile Ala Asn Leu Ile Glu Ser Thr
                85                  90                  95

Asp Val Ala Glu Asn Met Gly Ala Leu Arg Ala Ile Asp Glu Leu Thr
            100                 105                 110

Glu Ile Gly Phe Gly Glu Asn Ala Thr Lys Val Ser Arg Phe Ala Gly
        115                 120                 125
```

```
Tyr Met Arg Thr Val Phe Glu Leu Lys Arg Asp Pro Glu Ile Leu Val
    130                 135                 140

Leu Ala Ser Arg Val Leu Gly His Leu Ala Arg Ala Gly Gly Ala Met
145                 150                 155                 160

Thr Ser Asp Glu Val Glu Phe Gln Met Lys Thr Ala Phe Asp Trp Leu
                165                 170                 175

Arg Val Asp Arg Val Glu Tyr Arg Arg Phe Ala Ala Val Leu Ile Leu
                180                 185                 190

Lys Glu Met Ala Glu Asn Ala Ser Thr Val Phe Asn Val His Val Pro
            195                 200                 205

Glu Phe Val Asp Ala Ile Trp Val Ala Leu Arg Asp Pro Gln Leu Gln
210                 215                 220

Val Arg Glu Arg Ala Val Glu Ala Leu Arg Ala Cys Leu Arg Val Ile
225                 230                 235                 240

Glu Lys Arg Glu Thr Arg Trp Arg Val Gln Trp Tyr Tyr Arg Met Phe
                245                 250                 255

Glu Ala Thr Gln Asp Gly Leu Gly Arg Asn Ala Pro Val His Ser Ile
                260                 265                 270

His Gly Ser Leu Leu Ala Val Gly Glu Leu Leu Arg Asn Thr Gly Glu
            275                 280                 285

Phe Met Met Ser Arg Tyr Arg Glu Val Ala Glu Ile Val Leu Arg Tyr
290                 295                 300

Leu Glu His Arg Asp Arg Leu Val Arg Leu Ser Ile Thr Ser Leu Leu
305                 310                 315                 320

Pro Arg Ile Ala His Phe Leu Arg Asp Arg Phe Val Thr Asn Tyr Leu
                325                 330                 335

Thr Ile Cys Met Asn His Ile Leu Thr Val Leu Arg Ile Pro Ala Glu
                340                 345                 350

Arg Ala Ser Gly Phe Ile Ala Leu Gly Glu Met Ala Gly Ala Leu Asp
            355                 360                 365

Gly Glu Leu Ile His Tyr Leu Pro Thr Ile Met Ser His Leu Arg Asp
370                 375                 380

Ala Ile Ala Pro Arg Lys Gly Arg Pro Leu Leu Glu Ala Val Ala Cys
385                 390                 395                 400

Val Gly Asn Ile Ala Lys Ala Met Gly Ser Thr Val Glu Thr His Val
                405                 410                 415

Arg Asp Leu Leu Asp Val Met Phe Ser Ser Leu Ser Ser Thr Leu
                420                 425                 430

Val Asp Ala Leu Asp Gln Ile Thr Ile Ser Ile Pro Ser Leu Leu Pro
            435                 440                 445

Thr Val Gln Asp Arg Leu Leu Asp Cys Ile Ser Leu Val Leu Ser Lys
450                 455                 460

Ser His Tyr Ser Gln Ala Lys Pro Pro Val Thr Ile Val Arg Gly Ser
465                 470                 475                 480

Thr Val Gly Met Ala Pro Gln Ser Ser Asp Pro Ser Cys Ser Ala Gln
                485                 490                 495

Val Gln Leu Ala Leu Gln Thr Leu Ala Arg Phe Asn Phe Lys Gly His
            500                 505                 510

Asp Leu Leu Glu Phe Ala Arg Glu Ser Val Val Tyr Leu Asp Asp
515                 520                 525

Glu Asp Ala Ala Thr Arg Lys Asp Ala Ala Leu Cys Cys Cys Arg Leu
530                 535                 540

Ile Ala Asn Ser Leu Ser Gly Ile Thr Gln Phe Gly Ser Ser Arg Ser
```

```
                545                 550                 555                 560
Thr Arg Ala Gly Gly Arg Arg Arg Leu Val Glu Ile Val Glu
                565                 570                 575

Lys Leu Leu Arg Thr Ala Val Ala Asp Ala Asp Val Thr Val Arg Lys
                580                 585                 590

Ser Ile Phe Val Ala Leu Phe Gly Asn Gln Cys Phe Asp Asp Tyr Leu
                595                 600                 605

Ala Gln Ala Asp Ser Leu Thr Ala Ile Phe Ala Ser Leu Asn Asp Glu
        610                 615                 620

Asp Leu Asp Val Arg Glu Tyr Ala Ile Ser Val Ala Gly Arg Leu Ser
625                 630                 635                 640

Glu Lys Asn Pro Ala Tyr Val Leu Pro Ala Leu Arg Arg His Leu Ile
                645                 650                 655

Gln Leu Leu Thr Tyr Leu Glu Leu Ser Ala Asp Asn Lys Cys Arg Glu
                660                 665                 670

Glu Ser Ala Lys Leu Leu Gly Cys Leu Val Arg Asn Cys Glu Arg Leu
                675                 680                 685

Ile Leu Pro Tyr Val Ala Pro Val Gln Lys Ala Leu Val Ala Arg Leu
        690                 695                 700

Ser Glu Gly Thr Gly Val Asn Ala Asn Asn Ile Val Thr Gly Val
705                 710                 715                 720

Leu Val Thr Val Gly Asp Leu Ala Arg Val Gly Gly Leu Ala Met Arg
                725                 730                 735

Gln Tyr Ile Pro Glu Leu Met Pro Leu Ile Val Glu Ala Leu Met Asp
                740                 745                 750

Gly Ala Ala Val Ala Lys Arg Glu Val Ala Val Ser Thr Leu Gly Gln
                755                 760                 765

Val Val Gln Ser Thr Gly Tyr Val Val Thr Pro Tyr Lys Glu Tyr Pro
        770                 775                 780

Leu Leu Leu Gly Leu Leu Leu Lys Leu Leu Lys Gly Asp Leu Val Trp
785                 790                 795                 800

Ser Thr Arg Arg Glu Val Leu Lys Val Leu Gly Ile Met Gly Ala Leu
                805                 810                 815

Asp Pro His Val His Lys Arg Asn Gln Gln Ser Leu Ser Gly Ser His
                820                 825                 830

Gly Glu Val Pro Arg Gly Thr Gly Asp Ser Gly Gln Pro Ile Pro Ser
        835                 840                 845

Ile Asp Glu Leu Pro Val Glu Leu Arg Pro Ser Phe Ala Thr Ser Glu
850                 855                 860

Asp Tyr Tyr Ser Thr Val Ala Ile Asn Ser Leu Met Arg Ile Leu Arg
865                 870                 875                 880

Asp Ala Ser Leu Leu Ser Tyr His Lys Arg Val Val Arg Ser Leu Met
                885                 890                 895

Ile Ile Phe Lys Ser Met Gly Leu Gly Cys Val Pro Tyr Leu Pro Lys
                900                 905                 910

Val Leu Pro Glu Leu Phe His Thr Val Arg Thr Ser Asp Glu Asn Leu
                915                 920                 925

Lys Asp Phe Ile Thr Trp Gly Leu Gly Thr Leu Val Ser Ile Val Arg
        930                 935                 940

Gln His Ile Arg Lys Tyr Leu Pro Glu Leu Leu Ser Leu Val Ser Glu
945                 950                 955                 960

Leu Trp Ser Ser Phe Thr Leu Pro Gly Pro Ile Arg Pro Ser Arg Gly
                965                 970                 975
```

```
Leu Pro Val Leu His Leu Leu Glu His Leu Cys Leu Ala Leu Asn Asp
            980                 985                 990

Glu Phe Arg Thr Tyr Leu Pro Val Ile Leu Pro Cys Phe Ile Gln Val
            995                1000                1005

Leu Gly Asp Ala Glu Arg Phe Asn Asp Tyr Thr Tyr Val Pro Asp
       1010                1015                1020

Ile Leu His Thr Leu Glu Val Phe Gly Gly Thr Leu Asp Glu His
       1025                1030                1035

Met His Leu Leu Leu Pro Ala Leu Ile Arg Leu Phe Lys Val Asp
       1040                1045                1050

Ala Pro Val Ala Ile Arg Arg Asp Ala Ile Lys Thr Leu Thr Arg
       1055                1060                1065

Val Ile Pro Cys Val Gln Val Thr Gly His Ile Ser Ala Leu Val
       1070                1075                1080

His His Leu Lys Leu Val Leu Asp Gly Lys Asn Asp Glu Leu Arg
       1085                1090                1095

Lys Asp Ala Val Asp Ala Leu Cys Cys Leu Ala His Ala Leu Gly
       1100                1105                1110

Glu Asp Phe Thr Ile Phe Ile Glu Ser Ile His Lys Leu Leu Leu
       1115                1120                1125

Lys His Arg Leu Arg His Lys Glu Phe Glu Glu Ile His Ala Arg
       1130                1135                1140

Trp Arg Arg Arg Glu Pro Leu Ile Val Ala Thr Thr Ala Thr Gln
       1145                1150                1155

Gln Leu Ser Arg Arg Leu Pro Val Glu Val Ile Arg Asp Pro Val
       1160                1165                1170

Ile Glu Asn Glu Ile Asp Pro Phe Glu Glu Gly Thr Asp Arg Asn
       1175                1180                1185

His Gln Val Asn Asp Gly Arg Leu Arg Thr Ala Gly Glu Ala Ser
       1190                1195                1200

Gln Arg Ser Thr Lys Glu Asp Trp Glu Trp Met Arg His Phe
       1205                1210                1215

Ser Ile Glu Leu Leu Lys Glu Ser Pro Ser Pro Ala Leu Arg Thr
       1220                1225                1230

Cys Ala Lys Leu Ala Gln Leu Gln Pro Phe Val Gly Arg Glu Leu
       1235                1240                1245

Phe Ala Ala Gly Phe Val Ser Cys Trp Ala Gln Leu Asn Glu Ser
       1250                1255                1260

Ser Gln Lys Gln Leu Val Arg Ser Leu Glu Met Ala Phe Ser Ser
       1265                1270                1275

Pro Asn Ile Pro Pro Glu Ile Leu Ala Thr Leu Leu Asn Leu Ala
       1280                1285                1290

Glu Phe Met Glu His Asp Glu Lys Pro Leu Pro Ile Asp Ile Arg
       1295                1300                1305

Leu Leu Gly Ala Leu Ala Glu Lys Cys Arg Val Phe Ala Lys Ala
       1310                1315                1320

Leu His Tyr Lys Glu Met Glu Phe Glu Gly Pro Arg Ser Lys Arg
       1325                1330                1335

Met Asp Ala Asn Pro Val Ala Val Val Glu Ala Leu Ile His Ile
       1340                1345                1350

Asn Asn Gln Leu His Gln His Glu Ala Ala Val Gly Ile Leu Thr
       1355                1360                1365

Tyr Ala Gln Gln His Leu Asp Val Gln Leu Lys Glu Ser Trp Tyr
       1370                1375                1380
```

```
Glu Lys Leu Gln Arg Trp Asp Asp Ala Leu Lys Ala Tyr Thr Leu
    1385                1390                1395

Lys Ala Ser Gln Thr Thr Asn Pro His Leu Val Leu Glu Ala Thr
    1400                1405                1410

Leu Gly Gln Met Arg Cys Leu Ala Ala Leu Ala Arg Trp Glu Glu
    1415                1420                1425

Leu Asn Asn Leu Cys Lys Glu Tyr Trp Ser Pro Ala Glu Pro Ser
    1430                1435                1440

Ala Arg Leu Glu Met Ala Pro Met Ala Ala Gln Ala Ala Trp Asn
    1445                1450                1455

Met Gly Glu Trp Asp Gln Met Ala Glu Tyr Val Ser Arg Leu Asp
    1460                1465                1470

Asp Gly Asp Glu Thr Lys Leu Arg Gly Leu Ala Ser Pro Val Ser
    1475                1480                1485

Ser Gly Asp Gly Ser Ser Asn Gly Thr Phe Phe Arg Ala Val Leu
    1490                1495                1500

Leu Val Arg Arg Ala Lys Tyr Asp Glu Ala Arg Glu Tyr Val Glu
    1505                1510                1515

Arg Ala Arg Lys Cys Leu Ala Thr Glu Leu Ala Ala Leu Val Leu
    1520                1525                1530

Glu Ser Tyr Glu Arg Ala Tyr Ser Asn Met Val Arg Val Gln Gln
    1535                1540                1545

Leu Ser Glu Leu Glu Glu Val Ile Glu Tyr Tyr Thr Leu Pro Val
    1550                1555                1560

Gly Asn Thr Ile Ala Glu Glu Arg Arg Ala Leu Ile Arg Asn Met
    1565                1570                1575

Trp Thr Gln Arg Ile Gln Gly Ser Lys Arg Asn Val Glu Val Trp
    1580                1585                1590

Gln Ala Leu Leu Ala Val Arg Ala Leu Val Leu Pro Pro Thr Glu
    1595                1600                1605

Asp Val Glu Thr Trp Leu Lys Phe Ala Ser Leu Cys Arg Lys Ser
    1610                1615                1620

Gly Arg Ile Ser Gln Ala Lys Ser Thr Leu Leu Lys Leu Leu Pro
    1625                1630                1635

Phe Asp Pro Glu Val Ser Pro Glu Asn Met Gln Tyr His Gly Pro
    1640                1645                1650

Pro Gln Val Met Leu Gly Tyr Leu Lys Tyr Gln Trp Ser Leu Gly
    1655                1660                1665

Glu Glu Arg Lys Arg Lys Glu Ala Phe Thr Lys Leu Gln Ile Leu
    1670                1675                1680

Thr Arg Glu Leu Ser Ser Val Pro His Ser Gln Ser Asp Ile Leu
    1685                1690                1695

Ala Ser Met Val Ser Ser Lys Gly Ala Asn Val Pro Leu Leu Ala
    1700                1705                1710

Arg Val Asn Leu Lys Leu Gly Thr Trp Gln Trp Ala Leu Ser Ser
    1715                1720                1725

Gly Leu Asn Asp Gly Ser Ile Gln Glu Ile Arg Asp Ala Phe Asp
    1730                1735                1740

Lys Ser Thr Cys Tyr Ala Pro Lys Trp Ala Lys Ala Trp His Thr
    1745                1750                1755

Trp Ala Leu Phe Asn Thr Ala Val Met Ser His Tyr Ile Ser Arg
    1760                1765                1770

Gly Gln Ile Ala Ser Gln Tyr Val Val Ser Ala Val Thr Gly Tyr
```

-continued

```
                1775                1780                1785

Phe Tyr Ser Ile Ala Cys Ala Asn Ala Lys Gly Val Asp Asp
    1790                1795                1800

Ser Leu Gln Asp Ile Leu Arg Leu Leu Thr Leu Trp Phe Asn His
    1805                1810                1815

Gly Ala Thr Ala Asp Val Gln Thr Ala Leu Lys Thr Gly Phe Ser
    1820                1825                1830

His Val Asn Ile Asn Thr Trp Leu Val Val Leu Pro Gln Ile Ile
    1835                1840                1845

Ala Arg Ile His Ser Asn Asn Arg Ala Val Arg Glu Leu Ile Gln
    1850                1855                1860

Ser Leu Leu Ile Arg Ile Gly Glu Asn His Pro Gln Ala Leu Met
    1865                1870                1875

Tyr Pro Leu Leu Val Ala Cys Lys Ser Ile Ser Asn Leu Arg Arg
    1880                1885                1890

Ala Ala Ala Gln Glu Val Val Asp Lys Val Arg Gln His Ser Gly
    1895                1900                1905

Ala Leu Val Asp Gln Ala Gln Leu Val Ser His Glu Leu Ile Arg
    1910                1915                1920

Val Ala Ile Leu Trp His Glu Met Trp His Glu Ala Leu Glu Glu
    1925                1930                1935

Ala Ser Arg Leu Tyr Phe Gly Glu His Asn Ile Glu Gly Met Leu
    1940                1945                1950

Lys Val Leu Glu Pro Leu His Asp Met Leu Asp Glu Gly Val Lys
    1955                1960                1965

Lys Asp Ser Thr Thr Ile Gln Glu Arg Ala Phe Ile Glu Ala Tyr
    1970                1975                1980

Arg His Glu Leu Lys Glu Ala His Glu Cys Cys Cys Asn Tyr Lys
    1985                1990                1995

Ile Thr Gly Lys Asp Ala Glu Leu Thr Gln Ala Trp Asp Leu Tyr
    2000                2005                2010

Tyr His Val Phe Lys Arg Ile Asp Lys Gln Leu Ala Ser Leu Thr
    2015                2020                2025

Thr Leu Asp Leu Glu Ser Val Ser Pro Glu Leu Leu Leu Cys Arg
    2030                2035                2040

Asp Leu Glu Leu Ala Val Pro Gly Thr Tyr Arg Ala Asp Ala Pro
    2045                2050                2055

Val Val Thr Ile Ser Ser Phe Ser Arg Gln Leu Val Val Ile Thr
    2060                2065                2070

Ser Lys Gln Arg Pro Arg Lys Leu Thr Ile His Gly Asn Asp Gly
    2075                2080                2085

Glu Asp Tyr Ala Phe Leu Leu Lys Gly His Glu Asp Leu Arg Gln
    2090                2095                2100

Asp Glu Arg Val Met Gln Leu Phe Gly Leu Val Asn Thr Leu Leu
    2105                2110                2115

Glu Asn Ser Arg Lys Thr Ala Glu Lys Asp Leu Ser Ile Gln Arg
    2120                2125                2130

Tyr Ser Val Ile Pro Leu Ser Pro Asn Ser Gly Leu Ile Gly Trp
    2135                2140                2145

Val Pro Asn Cys Asp Thr Leu His His Leu Ile Arg Glu His Arg
    2150                2155                2160

Asp Ala Arg Lys Ile Ile Leu Asn Gln Glu Asn Lys His Met Leu
    2165                2170                2175
```

-continued

| Ser | Phe | Ala | Pro | Asp | Tyr | Asp | Asn | Leu | Pro | Leu | Ile | Ala | Lys | Val |
| | | | | 2180 | | | | | 2185 | | | | | 2190 |

| Glu | Val | Phe | Glu | Tyr | Ala | Leu | Glu | Asn | Thr | Glu | Gly | Asn | Asp | Leu |
| | 2195 | | | | | 2200 | | | | | 2205 | | | |

| Ser | Arg | Val | Leu | Trp | Leu | Lys | Ser | Arg | Ser | Ser | Glu | Val | Trp | Leu |
| 2210 | | | | | 2215 | | | | | 2220 | | | | |

| Glu | Arg | Arg | Thr | Asn | Tyr | Thr | Arg | Ser | Leu | Ala | Val | Met | Ser | Met |
| 2225 | | | | | 2230 | | | | | 2235 | | | | |

| Val | Gly | Tyr | Ile | Leu | Gly | Leu | Gly | Asp | Arg | His | Pro | Ser | Asn | Leu |
| 2240 | | | | | 2245 | | | | | 2250 | | | | |

| Met | Leu | His | Arg | Tyr | Ser | Gly | Lys | Ile | Leu | His | Ile | Asp | Phe | Gly |
| 2255 | | | | | 2260 | | | | | 2265 | | | | |

| Asp | Cys | Phe | Glu | Ala | Ser | Met | Asn | Arg | Glu | Lys | Phe | Pro | Glu | Lys |
| 2270 | | | | | 2275 | | | | | 2280 | | | | |

| Val | Pro | Phe | Arg | Leu | Thr | Arg | Met | Leu | Val | Lys | Ala | Met | Glu | Val |
| 2285 | | | | | 2290 | | | | | 2295 | | | | |

| Ser | Gly | Ile | Glu | Gly | Asn | Phe | Arg | Ser | Thr | Cys | Glu | Asn | Val | Met |
| 2300 | | | | | 2305 | | | | | 2310 | | | | |

| Gln | Val | Leu | Arg | Thr | Asn | Lys | Asp | Ser | Val | Met | Ala | Met | Met | Glu |
| 2315 | | | | | 2320 | | | | | 2325 | | | | |

| Ala | Phe | Val | His | Asp | Pro | Leu | Ile | Asn | Trp | Arg | Leu | Phe | Asn | Phe |
| 2330 | | | | | 2335 | | | | | 2340 | | | | |

| Asn | Glu | Val | Pro | Gln | Leu | Ala | Leu | Leu | Gly | Asn | Asn | Asn | Pro | Asn |
| 2345 | | | | | 2350 | | | | | 2355 | | | | |

| Ala | Pro | Ala | Asp | Val | Glu | Pro | Asp | Glu | Glu | Asp | Glu | Asp | Pro | Ala |
| 2360 | | | | | 2365 | | | | | 2370 | | | | |

| Asp | Ile | Asp | Leu | Pro | Gln | Pro | Gln | Arg | Ser | Thr | Arg | Glu | Lys | Glu |
| 2375 | | | | | 2380 | | | | | 2385 | | | | |

| Ile | Leu | Gln | Ala | Val | Asn | Met | Leu | Gly | Asp | Ala | Asn | Glu | Val | Leu |
| 2390 | | | | | 2395 | | | | | 2400 | | | | |

| Asn | Glu | Arg | Ala | Val | Val | Met | Ala | Arg | Met | Ser | His | Lys | Leu |
| 2405 | | | | | 2410 | | | | | 2415 | | | | |

| Thr | Gly | Arg | Asp | Phe | Ser | Ser | Ala | Ile | Pro | Ser | Asn | Pro | Ile |
| 2420 | | | | | 2425 | | | | | 2430 | | | | |

| Ala | Asp | His | Asn | Asn | Leu | Leu | Gly | Gly | Asp | Ser | His | Glu | Val | Glu |
| 2435 | | | | | 2440 | | | | | 2445 | | | | |

| His | Gly | Leu | Ser | Val | Lys | Val | Gln | Val | Gln | Lys | Leu | Ile | Asn | Gln |
| 2450 | | | | | 2455 | | | | | 2460 | | | | |

| Ala | Thr | Ser | His | Glu | Asn | Leu | Cys | Gln | Asn | Tyr | Val | Gly | Trp | Cys |
| 2465 | | | | | 2470 | | | | | 2475 | | | | |

| Pro | Phe | Trp |
| 2480 | | |

<210> SEQ ID NO 3
<211> LENGTH: 7443
<212> TYPE: DNA
<213> ORGANISM: Brassica napus

<400> SEQUENCE: 3

```
atgtctacct cgtcgcaatc gttttcggct ggacggcctt cacccctggc ttctccgtcg      60
caatctcacc gcttttgtgg gccttcagct acatcttctg gcggcggaag cttcgacact     120
ttgaaccgtg tcatcactga cctttgcagc catggtaatc ctaaggaggg agcttcttta     180
gcgtttagga aacacgtgga ggaagcagtt cgtgatctta gcggtgaagc ttcctctagg     240
ttcatggagc agttatatga caggattgct actttaattg agagctcgag tgaggctgaa     300
```

```
aacatgggtg gccttagagc catcgatgag ttgacagaga ttggatttgg tgagaatgct    360
acaaatgttt ctcgctttgc gggttttatg aggactgtgt tgtccaagcg tgaccctgaa    420
atcttggtgc ttgctagtag agttttgggc caccttgctc gagctggtgg agtcatgact    480
tctgatgaag tcgagtttca gatgaaaact gcttttgatt ggcttcacgg agacagggtg    540
gaatatcgtc gtttcgccgc tgttctaatt ttgaaggaga tggcagaaaa cgcatccact    600
gtctttaatg ttcacgtccc tcaatttgtg gatgcgatct gggttgcatt aagggatccc    660
cagttgcaag tacgggagcg agctgttgaa gctttacgtg cttgccttcg cgttatcgag    720
agaagggaga ctcgatggcg tgtacaatgg tactatcgaa tgtttgaagc tacacaggat    780
gggttgggca gaaatgctcc ggtccatagt attcatggtt ccttacttgc tgtggggag    840 ctattgagga atactggtga gttcatgatg tctaggtacc gagaagttgc tgacattgtc    900
cttagatacc ttgaacatcg tgatcgcctt gttcgcctta gcatcacctc gttgctgcct    960
cgaattgctc atttcctccg tgaccgcttt gttacaaact atttaacgat atgtatgaat   1020
catattctta ctgtgttaaa ataccggct gaacgtgcta gtggattcat cgcccttggg    1080
gaaatggctg gtgctttgga tggtgagctt atccactatt tgccgactat tatgtctcat   1140
ctgcgggagg cgattgctcc acgtaaaggt agacctttgc ttgaagctgt ggcttgtgtt   1200
ggtaacatcg cgaaggcaat gggatccacg gtggaaaatt atgttcgaga tcttctagat   1260
gctatgtttt cttctggtct ctcttctacg cttgttgacg ctcttgatca gataaccatt   1320
agcattcctt cattgctgcc gacggtacaa gatcggcttc tagattgcat tcattggtt    1380 ctttcaagat ctcattattc tcaaaccaag cctcctgtta ccctggttcg aagtagtaca   1440
gttagcatgg caccacagtc tactgatctt agtagttcag cccaagttca actagccctg   1500
cagactctgg ctcgtttcaa tttcaagggg catgatcttc ttgaattcgc tagggagtcg   1560
gttgttattt atttggatga tgggatgca accacaagaa aagatgctgc tttgtgctgt   1620
tgtagactaa ttgcagattc cttatcgggg atcacgcagt ttggctcaag caggtcaact   1680
cgagctggag gaagacgaat gcgccttgtg gaagagattg tggaaaagct tctcaggaca   1740
gctgttgcag atgctgatgt aaatgttcgc aagtctatat tcgttgcttt gtatggcaac   1800
caatgtttcg atgattatct agcacaggct gatagtttga ctgccatttt tgcttcatta   1860
aatgatgagg accttgatgt acgagaatat gccatctcag ttgctgggag ttatccgaa    1920 aaaaacccag catacgttct cccagcactt cgtcgccatc ttatacaact gttaacctat   1980
cttgagcaga gtgcggataa caagtgcaga gaagagagtg cgaagctcct cggttgttta   2040
gttcgaaatt gtgaacggct cattcttcca tatgtagctc ctgtgcaaaa ggcacttgtt   2100
gcgagactta gtgaaggaac tggagtgaat gctaacaata atattgtcac tggagttctc   2160
gtaactgttg gggatcttgc aagagtgggg ggcttggcaa tgagacaata tattccggag   2220
ctaatgcctt tgattgttga agctttaatg gatggagctg ctgtagcaaa acgtgaggtg   2280 gctgttttcca cccttggtca agtcgttcaa agtacagggt atgttgtgac tccatacaag   2340
gaatacccgt tgttgcttgg cttactcttg aaattgctta agggtgactt agtgtggtct   2400
accagacgag aagtgctcaa ggttcttgga attatgggcg cttttggatcc tcatgtgcat   2460 aaacgtaacc agcaaagttt atcaggatca catggtgaag ttcctcgggg tactggtgat   2520
tcaggtcaac ctattccatc gattgatgag ttacctgtgg aactccggcc atcatttgct   2580
acatctgagg attattactc tacggttgct atcaactcgc ttatgcgaat tcttagagat   2640
ccatcacttc ttagttacca caaaagggtt gttagatctc tgatgatcat ttttaagtca   2700
```

```
atgggattgg gatgcgtgcc ttatttgcca aaggttttac ctgagctttt tcacactgtc   2760
cgcacttctg atgaaaactt aaaggacttc attacatggg gtcttgggac tcttgtttcc   2820
atcgtgcgcc agcacatacg aaagtatctg ccagagttgc tctcactagt ctttgaacta   2880
tggtcatcct tcaccttgcc aggtcccgta cgcccctctc gtggtcttcc ggttctgcat   2940
ctactggaac atctttgttt ggcacttaat gatgaattca gaacttatct tccagtcatc   3000
cttccatgtt tcatccaagt attaggtgat gcggagcggt gtaatgatta tatctatgtt   3060
cctgatattc tccacacact cgaagtgttt ggcggtacac ttgatgagca catgcattta   3120
ctccttcctg cccttatccg attgtttaaa gtagatgctc ctgtagctat aagacgcgat   3180
gccatcaaaa cttttgacaag agttatcccg tgtgttcagg ttactggtca catctccgct   3240
cttgtgcatc acttgaagct agtattagat gggaagaatg atgagttgcg gaaagaggct   3300
gtcgatgcac tatgctgttt ggctcatgct cttggagagg acttcaccat attcattgaa   3360
tcaattcaca agcttttgtt gaagcatcgc ttgcggcata aagagtttga ggaaatttat   3420
gctcgatccc ggagacgtga accattgatt gtagctacaa cagccactca acagttaagt   3480
aggcgactgc cagtcgaggt tatcagggat cctgtaattg agaatgagat cgatcctttt   3540
gaagaaggaa acgacaaaaa ccatcaggtt aatgatggta gactacggac agctggagaa   3600
gcttctcaac gcagtaccaa ggaagactgg gaagaatgga tgagacattt tagtattgaa   3660
ttacttaaag agtctccctc tccagcattg agaacttgtg caaaacttgc tcagttgcag   3720
ccttttgtcg ggagagaatt gtttgccgct ggctttgtca gttgctgggc acagctgaat   3780
gaagctagcc aaacgcagtt agttaggagc ttggagatgg cttttttcatc tccaaatatc   3840 cctcctgaga ttttggcgac actacttaat ttggcagagt ttatggaaca tgatgaaaag   3900
cctcttccca ttgatattcg tctcctgggg gctcttgctg aaaagtgccg tgttttttgcc   3960 aaagctttgc actataaaga gatggaattt gagggtccac ggtccaggag gatggatgcc   4020
aacccagttg ctattgttga ggcacttata cacataaata atcaattaca ccagcatgag   4080
gctgctgtcg gcatactgac ctatgctcaa caacatcttg atgtgcaatt aaaagaatca   4140
tggtacgaga agctgcagcg atgggacgat gcactcaagg cgtacacttt gaaagcatct   4200
caaacatcta atccccatct tgtattagaa gccacattag gaaaaatgag atgtctcgct   4260
gcacttgccc gatgggaaga gctaaataat cttttgcaagg agtactggag tccagctgag   4320
ccatctgcac gtctggaaat ggcaccaatg gctgccaatg ctgcgtggaa tatgggagag   4380
tgggatcaaa tggcggaata tgtgtctcgg ttagatgatg gcgatgaaac aaagcttagg   4440
ggtttagcaa gccctgcttc aagtggcgat ggaagcagca atggcacatt cttcagggct   4500
gttttgttag ttcggagggc gaagtatgat gaggcgcggg aatatgttga agagctagaa   4560
aaatgtcttg cgacagaact tgcagcgctg gttttggaga gttacgagcg tgcttacagc   4620
aatatggttc gagtccagca gctgtcagaa ctagaagagg taattgaata ttatacgctg   4680
cctgtgggaa ataatattgc tgaagaacgg agagccctaa ttcgtagtat gtggactcag   4740
cggattcagg gatctaagcg taatgtagag gtgtggcaat cacttttggc tgttcgggca   4800
cttgtgctac ctcctacaga agatgttgaa acttggctca gtttgcctc gctttgtcga   4860 aaaagtggga ggatcagtca ggcaaagtct actctactca agctcttgcc gtttgatcca   4920
gaagtatcac cagaagacat gcaatatcac ggacctccac aagtgatgct tggatatta   4980 aaataccaat ggtcacttgg agaggaacgc aagcgcaaag aggcgtttgc caagctgcaa   5040
attctgacga gggaactctc aagtgtgcca cattctcagt ctgacatgat ggctagtatg   5100
```

```
gtatctagca agggagcaaa tgttccactt cttgcacgtg taaatctcaa attgggaaca   5160
tggcagtggg cactttctcc cggattgaat gatgggtcta ttcaagaaat tcttgatgcc   5220
tttagcaaat ctaccatcta tgctcctaaa tgggctaagg catggcacac atgggcgtta   5280
ttcaatacgg cagtgatgtc tcattacata tcaaaaggtc aaattgcttc tcagtttgtt   5340
gctgctgcag tcactggata cttccattct atagcatgtg cagcgaatgc gaaaggagtt   5400
gatgatagtt tacaggatat actgcgtctt ctcacgttat ggttcaacca tggagctacg   5460
gctgatgtcc aaacagcatt gaagagagga ttcagtcatg tcagcattga cacatggctt   5520
gttgtgttgc ctcaaataat tgctaggata cattcaaata accgtgctgt cagggaattg   5580
atacagtctc ttctcatccg cataggagaa aaccacccac aggctcttat gtatcccctt   5640
ctcgttgcat gtaaatcaat aagcaatttg cggagagctg cagctcaaga ggtggttgat   5700
caagttcgcc agcacagtgg cgcccttgtg gatcaggcac aacttgtatc acatgaactt   5760
atcagggttg ctatactttg gcatgaaatg tggcatgaag cactagaaga agctagtcgc   5820
ttgtattttg gagaacataa cattgaagga atgctgaaag tacttgagcc attacatgag   5880
atgcttgaag aaggtgcaag aaaggacaat gtgaccatac aagagagagc atttatagag   5940
gcataccgtc acgaactact agaggcatat gaatgttgta tcaattacaa gagaactgga   6000
aaagatgctg aacttacaca ggcttgggat ctttactatc acgtattcaa acggattgac   6060
aaacagcttg ccagtctcac aacattggat ttggaatctg tatctcctga attgctgctg   6120
tgtcgtgact tggagctagc tgttcctgga acataccgtg cggatgcccc cgttgtgacg   6180
atagcatcgt tttctcgtca acttcttgtc ataacatcca acaacgacc acggaaattg   6240
actattcacg gaaatgacgg tgaggactat gcattttgt taaagggaca tgaagattta   6300
aggcaagatg agcgtgttat gcagcttttt ggtttggtga acactttgct cgagaattcc   6360
agaaaaacag cagaaaaaga tttgtccatc caacggtatt ctgtaatacc attatctccc   6420
aatagtggac tcattggatg ggttcccaac tgcgataccc ttcaccatct tattcgagaa   6480
tacagagatg cacgaaagat cattcttaat caagaacaca acatatgtt gagttttgct   6540
ccaaactacg acaatctacc gctcatagca aagattgaag tatttgagta cgctcttgaa   6600
aacacagagg gaaatgatct gtccagggtt ctctggttaa aaagtcgctc gtcagaggta   6660
tggctggaga gaagaaccaa ctatactaga agtttagccg ttatgagtat ggttggttat   6720
attcttgggt taggtgatcg acacccaagt aaccttatgc tagatagata cagtgggaaa   6780
atcttgcata ttgatttcgg agattgtttt gaggcgtcta tgaatagaga aagtttcct   6840
gaaaaggttc cgttccgtct gacaagaatg cttgtcaaag caatggaagt aagtggcatc   6900
gaaggaaact tccggtcgac atgcgaaaat gttatgcaag ttctcagaac caacaaagac   6960
agtgtaatgg caatgatgga ggcgtttgtg catgatcctt taatcaattg gcgtcttttt   7020
aatttcaatg aagtccctca actagcccta ctcggtaaca acaatcccaa cggtcctgct   7080
aatgttgaac ctgaggaagt agatgaagat cccgctgatg tagaccttcc tcagcctcaa   7140
aggagtactc gagagaagga aattcttcag gctgtgaata tgcttggaga tgcaaatgag   7200
gtattgaacg agcgtgcagt agttgtcatg gctcgtatga gtcataagct tacaggccgt   7260
gatttctcta cgtctgcggt tccaagcaat cccattgctg atcacaataa cttgctcgga   7320
ggagattctc atgaagtcga acatggtttg tctgtgaaag ttcaggttca aaagctaatt   7380
gatcaagcca cttcccatga aaatctatgt caaaattatg ttgggtggtg ccctttctgg   7440
tga                                                                7443
```

```
<210> SEQ ID NO 4
<211> LENGTH: 2480
<212> TYPE: PRT
<213> ORGANISM: Brassica napus

<400> SEQUENCE: 4

Met Ser Thr Ser Ser Gln Ser Phe Ser Ala Gly Arg Pro Ser Pro Leu
1               5                   10                  15

Ala Ser Pro Ser Gln Ser His Arg Phe Cys Gly Pro Ser Ala Thr Ser
            20                  25                  30

Ser Gly Gly Gly Ser Phe Asp Thr Leu Asn Arg Val Ile Thr Asp Leu
        35                  40                  45

Cys Ser His Gly Asn Pro Lys Glu Gly Ala Ser Leu Ala Phe Arg Lys
    50                  55                  60

His Val Glu Glu Ala Val Arg Asp Leu Ser Gly Glu Ala Ser Ser Arg
65                  70                  75                  80

Phe Met Glu Gln Leu Tyr Asp Arg Ile Ala Thr Leu Ile Glu Ser Ser
                85                  90                  95

Ser Glu Ala Glu Asn Met Gly Gly Leu Arg Ala Ile Asp Glu Leu Thr
            100                 105                 110

Glu Ile Gly Phe Gly Glu Asn Ala Thr Asn Val Ser Arg Phe Ala Gly
        115                 120                 125

Phe Met Arg Thr Val Leu Ser Lys Arg Asp Pro Glu Ile Leu Val Leu
    130                 135                 140

Ala Ser Arg Val Leu Gly His Leu Ala Arg Ala Gly Gly Val Met Thr
145                 150                 155                 160

Ser Asp Glu Val Glu Phe Gln Met Lys Thr Ala Phe Asp Trp Leu His
                165                 170                 175

Gly Asp Arg Val Glu Tyr Arg Arg Phe Ala Ala Val Leu Ile Leu Lys
            180                 185                 190

Glu Met Ala Glu Asn Ala Ser Thr Val Phe Asn Val His Val Pro Gln
        195                 200                 205

Phe Val Asp Ala Ile Trp Val Ala Leu Arg Asp Pro Gln Leu Gln Val
    210                 215                 220

Arg Glu Arg Ala Val Glu Ala Leu Arg Ala Cys Leu Arg Val Ile Glu
225                 230                 235                 240

Arg Arg Glu Thr Arg Trp Arg Val Gln Trp Tyr Arg Met Phe Glu
                245                 250                 255

Ala Thr Gln Asp Gly Leu Gly Arg Asn Ala Pro Val His Ser Ile His
            260                 265                 270

Gly Ser Leu Leu Ala Val Gly Glu Leu Leu Arg Asn Thr Gly Glu Phe
        275                 280                 285

Met Met Ser Arg Tyr Arg Glu Val Ala Asp Ile Val Leu Arg Tyr Leu
    290                 295                 300

Glu His Arg Asp Arg Leu Val Arg Leu Ser Ile Thr Ser Leu Leu Pro
305                 310                 315                 320

Arg Ile Ala His Phe Leu Arg Asp Arg Phe Val Thr Asn Tyr Leu Thr
                325                 330                 335

Ile Cys Met Asn His Ile Leu Thr Val Leu Lys Ile Pro Ala Glu Arg
            340                 345                 350

Ala Ser Gly Phe Ile Ala Leu Gly Glu Met Ala Gly Ala Leu Asp Gly
        355                 360                 365

Glu Leu Ile His Tyr Leu Pro Thr Ile Met Ser His Leu Arg Glu Ala
    370                 375                 380
```

```
Ile Ala Pro Arg Lys Gly Arg Pro Leu Leu Glu Ala Val Ala Cys Val
385                 390                 395                 400

Gly Asn Ile Ala Lys Ala Met Gly Ser Thr Val Glu Asn Tyr Val Arg
                405                 410                 415

Asp Leu Leu Asp Ala Met Phe Ser Ser Gly Leu Ser Ser Thr Leu Val
                420                 425                 430

Asp Ala Leu Asp Gln Ile Thr Ile Ser Ile Pro Ser Leu Leu Pro Thr
            435                 440                 445

Val Gln Asp Arg Leu Leu Asp Cys Ile Ser Leu Val Leu Ser Arg Ser
        450                 455                 460

His Tyr Ser Gln Thr Lys Pro Pro Val Thr Leu Val Arg Ser Ser Thr
465                 470                 475                 480

Val Ser Met Ala Pro Gln Ser Thr Asp Leu Ser Ser Ser Ala Gln Val
                485                 490                 495

Gln Leu Ala Leu Gln Thr Leu Ala Arg Phe Asn Phe Lys Gly His Asp
                500                 505                 510

Leu Leu Glu Phe Ala Arg Glu Ser Val Val Ile Tyr Leu Asp Asp Gly
            515                 520                 525

Asp Ala Thr Thr Arg Lys Asp Ala Ala Leu Cys Cys Cys Arg Leu Ile
530                 535                 540

Ala Asp Ser Leu Ser Gly Ile Thr Gln Phe Gly Ser Ser Arg Ser Thr
545                 550                 555                 560

Arg Ala Gly Gly Arg Arg Met Arg Leu Val Glu Glu Ile Val Glu Lys
                565                 570                 575

Leu Leu Arg Thr Ala Val Ala Asp Ala Asp Val Asn Val Arg Lys Ser
            580                 585                 590

Ile Phe Val Ala Leu Tyr Gly Asn Gln Cys Phe Asp Asp Tyr Leu Ala
        595                 600                 605

Gln Ala Asp Ser Leu Thr Ala Ile Phe Ala Ser Leu Asn Asp Glu Asp
610                 615                 620

Leu Asp Val Arg Glu Tyr Ala Ile Ser Val Ala Gly Arg Leu Ser Glu
625                 630                 635                 640

Lys Asn Pro Ala Tyr Val Leu Pro Ala Leu Arg Arg His Leu Ile Gln
                645                 650                 655

Leu Leu Thr Tyr Leu Glu Gln Ser Ala Asp Asn Lys Cys Arg Glu Glu
            660                 665                 670

Ser Ala Lys Leu Leu Gly Cys Leu Val Arg Asn Cys Glu Arg Leu Ile
        675                 680                 685

Leu Pro Tyr Val Ala Pro Val Gln Lys Ala Leu Val Ala Arg Leu Ser
690                 695                 700

Glu Gly Thr Gly Val Asn Ala Asn Asn Ile Val Thr Gly Val Leu
705                 710                 715                 720

Val Thr Val Gly Asp Leu Ala Arg Val Gly Gly Leu Ala Met Arg Gln
                725                 730                 735

Tyr Ile Pro Glu Leu Met Pro Leu Ile Val Glu Ala Leu Met Asp Gly
            740                 745                 750

Ala Ala Val Ala Lys Arg Glu Val Ala Val Ser Thr Leu Gly Gln Val
        755                 760                 765

Val Gln Ser Thr Gly Tyr Val Val Thr Pro Tyr Lys Glu Tyr Pro Leu
        770                 775                 780

Leu Leu Gly Leu Leu Leu Lys Leu Leu Lys Gly Asp Leu Val Trp Ser
785                 790                 795                 800

Thr Arg Arg Glu Val Leu Lys Val Leu Gly Ile Met Gly Ala Leu Asp
```

-continued

```
                805                 810                 815
Pro His Val His Lys Arg Asn Gln Gln Ser Leu Ser Gly Ser His Gly
                820                 825                 830

Glu Val Pro Arg Gly Thr Gly Asp Ser Gly Gln Pro Ile Pro Ser Ile
                835                 840                 845

Asp Glu Leu Pro Val Glu Leu Arg Pro Ser Phe Ala Thr Ser Glu Asp
                850                 855                 860

Tyr Tyr Ser Thr Val Ala Ile Asn Ser Leu Met Arg Ile Leu Arg Asp
865                 870                 875                 880

Pro Ser Leu Leu Ser Tyr His Lys Arg Val Val Arg Ser Leu Met Ile
                885                 890                 895

Ile Phe Lys Ser Met Gly Leu Gly Cys Val Pro Tyr Leu Pro Lys Val
                900                 905                 910

Leu Pro Glu Leu Phe His Thr Val Arg Thr Ser Asp Glu Asn Leu Lys
                915                 920                 925

Asp Phe Ile Thr Trp Gly Leu Gly Thr Leu Val Ser Ile Val Arg Gln
                930                 935                 940

His Ile Arg Lys Tyr Leu Pro Glu Leu Leu Ser Leu Val Phe Glu Leu
945                 950                 955                 960

Trp Ser Ser Phe Thr Leu Pro Gly Pro Val Arg Pro Ser Arg Gly Leu
                965                 970                 975

Pro Val Leu His Leu Leu Glu His Cys Leu Ala Leu Asn Asp Glu
                980                 985                 990

Phe Arg Thr Tyr Leu Pro Val Ile  Leu Pro Cys Phe Ile  Gln Val Leu
                995                 1000                1005

Gly Asp Ala Glu Arg Cys Asn  Asp Tyr Ile Tyr Val  Pro Asp Ile
                1010                1015                1020

Leu His  Thr Leu Glu Val Phe  Gly Gly Thr Leu Asp  Glu His Met
                1025                1030                1035

His Leu  Leu Leu Pro Ala Leu  Ile Arg Leu Phe Lys  Val Asp Ala
                1040                1045                1050

Pro Val  Ala Ile Arg Arg Asp  Ala Ile Lys Thr Leu  Thr Arg Val
                1055                1060                1065

Ile Pro  Cys Val Gln Val Thr  Gly His Ile Ser Ala  Leu Val His
                1070                1075                1080

His Leu  Lys Leu Val Leu Asp  Gly Lys Asn Asp Glu  Leu Arg Lys
                1085                1090                1095

Glu Ala  Val Asp Ala Leu Cys  Cys Leu Ala His Ala  Leu Gly Glu
                1100                1105                1110

Asp Phe  Thr Ile Phe Ile Glu  Ser Ile His Lys Leu  Leu Leu Lys
                1115                1120                1125

His Arg  Leu Arg His Lys Glu  Phe Glu Glu Ile Tyr  Ala Arg Ser
                1130                1135                1140

Arg Arg  Arg Glu Pro Leu Ile  Val Ala Thr Thr Ala  Thr Gln Gln
                1145                1150                1155

Leu Ser  Arg Arg Leu Pro Val  Glu Val Ile Arg Asp  Pro Val Ile
                1160                1165                1170

Glu Asn  Glu Ile Asp Pro Phe  Glu Glu Gly Asn Asp  Lys Asn His
                1175                1180                1185

Gln Val  Asn Asp Gly Arg Leu  Arg Thr Ala Gly Glu  Ala Ser Gln
                1190                1195                1200

Arg Ser  Thr Lys Glu Asp Trp  Glu Glu Trp Met Arg  His Phe Ser
                1205                1210                1215
```

-continued

```
Ile Glu Leu Leu Lys Glu Ser Pro Ser Pro Ala Leu Arg Thr Cys
1220                1225                1230

Ala Lys Leu Ala Gln Leu Gln Pro Phe Val Gly Arg Glu Leu Phe
1235                1240                1245

Ala Ala Gly Phe Val Ser Cys Trp Ala Gln Leu Asn Glu Ala Ser
1250                1255                1260

Gln Thr Gln Leu Val Arg Ser Leu Glu Met Ala Phe Ser Ser Pro
1265                1270                1275

Asn Ile Pro Pro Glu Ile Leu Ala Thr Leu Leu Asn Leu Ala Glu
1280                1285                1290

Phe Met Glu His Asp Glu Lys Pro Leu Pro Ile Asp Ile Arg Leu
1295                1300                1305

Leu Gly Ala Leu Ala Glu Lys Cys Arg Val Phe Ala Lys Ala Leu
1310                1315                1320

His Tyr Lys Glu Met Glu Phe Glu Gly Pro Arg Ser Arg Arg Met
1325                1330                1335

Asp Ala Asn Pro Val Ala Ile Val Glu Ala Leu Ile His Ile Asn
1340                1345                1350

Asn Gln Leu His Gln His Glu Ala Ala Val Gly Ile Leu Thr Tyr
1355                1360                1365

Ala Gln Gln His Leu Asp Val Gln Leu Lys Glu Ser Trp Tyr Glu
1370                1375                1380

Lys Leu Gln Arg Trp Asp Asp Ala Leu Lys Ala Tyr Thr Leu Lys
1385                1390                1395

Ala Ser Gln Thr Ser Asn Pro His Leu Val Leu Glu Ala Thr Leu
1400                1405                1410

Gly Lys Met Arg Cys Leu Ala Ala Leu Ala Arg Trp Glu Glu Leu
1415                1420                1425

Asn Asn Leu Cys Lys Glu Tyr Trp Ser Pro Ala Glu Pro Ser Ala
1430                1435                1440

Arg Leu Glu Met Ala Pro Met Ala Ala Asn Ala Ala Trp Asn Met
1445                1450                1455

Gly Glu Trp Asp Gln Met Ala Glu Tyr Val Ser Arg Leu Asp Asp
1460                1465                1470

Gly Asp Glu Thr Lys Leu Arg Gly Leu Ala Ser Pro Ala Ser Ser
1475                1480                1485

Gly Asp Gly Ser Ser Asn Gly Thr Phe Phe Arg Ala Val Leu Leu
1490                1495                1500

Val Arg Arg Ala Lys Tyr Asp Glu Ala Arg Glu Tyr Val Glu Arg
1505                1510                1515

Ala Arg Lys Cys Leu Ala Thr Glu Leu Ala Ala Leu Val Leu Glu
1520                1525                1530

Ser Tyr Glu Arg Ala Tyr Ser Asn Met Val Arg Val Gln Gln Leu
1535                1540                1545

Ser Glu Leu Glu Glu Val Ile Glu Tyr Tyr Thr Leu Pro Val Gly
1550                1555                1560

Asn Asn Ile Ala Glu Glu Arg Arg Ala Leu Ile Arg Ser Met Trp
1565                1570                1575

Thr Gln Arg Ile Gln Gly Ser Lys Arg Asn Val Glu Val Trp Gln
1580                1585                1590

Ser Leu Leu Ala Val Arg Ala Leu Val Leu Pro Pro Thr Glu Asp
1595                1600                1605

Val Glu Thr Trp Leu Lys Phe Ala Ser Leu Cys Arg Lys Ser Gly
1610                1615                1620
```

```
Arg Ile Ser Gln Ala Lys Ser  Thr Leu Leu Lys Leu  Leu Pro Phe
    1625             1630              1635

Asp Pro Glu Val Ser Pro Glu  Asp Met Gln Tyr His  Gly Pro Pro
    1640             1645              1650

Gln Val Met Leu Gly Tyr Leu  Lys Tyr Gln Trp Ser  Leu Gly Glu
    1655             1660              1665

Glu Arg Lys Arg Lys Glu Ala  Phe Ala Lys Leu Gln  Ile Leu Thr
    1670             1675              1680

Arg Glu Leu Ser Ser Val Pro  His Ser Gln Ser Asp  Met Met Ala
    1685             1690              1695

Ser Met Val Ser Ser Lys Gly  Ala Asn Val Pro Leu  Leu Ala Arg
    1700             1705              1710

Val Asn Leu Lys Leu Gly Thr  Trp Gln Trp Ala Leu  Ser Pro Gly
    1715             1720              1725

Leu Asn Asp Gly Ser Ile Gln  Glu Ile Leu Asp Ala  Phe Ser Lys
    1730             1735              1740

Ser Thr Ile Tyr Ala Pro Lys  Trp Ala Lys Ala Trp  His Thr Trp
    1745             1750              1755

Ala Leu Phe Asn Thr Ala Val  Met Ser His Tyr Ile  Ser Lys Gly
    1760             1765              1770

Gln Ile Ala Ser Gln Phe Val  Ala Ala Ala Val Thr  Gly Tyr Phe
    1775             1780              1785

His Ser Ile Ala Cys Ala Ala  Asn Ala Lys Gly Val  Asp Asp Ser
    1790             1795              1800

Leu Gln Asp Ile Leu Arg Leu  Leu Thr Leu Trp Phe  Asn His Gly
    1805             1810              1815

Ala Thr Ala Asp Val Gln Thr  Ala Leu Lys Arg Gly  Phe Ser His
    1820             1825              1830

Val Ser Ile Asp Thr Trp Leu  Val Val Leu Pro Gln  Ile Ile Ala
    1835             1840              1845

Arg Ile His Ser Asn Asn Arg  Ala Val Arg Glu Leu  Ile Gln Ser
    1850             1855              1860

Leu Leu Ile Arg Ile Gly Glu  Asn His Pro Gln Ala  Leu Met Tyr
    1865             1870              1875

Pro Leu Leu Val Ala Cys Lys  Ser Ile Ser Asn Leu  Arg Arg Ala
    1880             1885              1890

Ala Ala Gln Glu Val Val Asp  Gln Val Arg Gln His  Ser Gly Ala
    1895             1900              1905

Leu Val Asp Gln Ala Gln Leu  Val Ser His Glu Leu  Ile Arg Val
    1910             1915              1920

Ala Ile Leu Trp His Glu Met  Trp His Glu Ala Leu  Glu Glu Ala
    1925             1930              1935

Ser Arg Leu Tyr Phe Gly Glu  His Asn Ile Glu Gly  Met Leu Lys
    1940             1945              1950

Val Leu Glu Pro Leu His Glu  Met Leu Glu Glu Gly  Ala Arg Lys
    1955             1960              1965

Asp Asn Val Thr Ile Gln Glu  Arg Ala Phe Ile Glu  Ala Tyr Arg
    1970             1975              1980

His Glu Leu Leu Glu Ala Tyr  Glu Cys Cys Ile Asn  Tyr Lys Arg
    1985             1990              1995

Thr Gly Lys Asp Ala Glu Leu  Thr Gln Ala Trp Asp  Leu Tyr Tyr
    2000             2005              2010

His Val Phe Lys Arg Ile Asp  Lys Gln Leu Ala Ser  Leu Thr Thr
```

```
                        2015                2020                2025

Leu Asp  Leu Glu Ser Val Ser  Pro Glu Leu Leu Leu  Cys Arg Asp
    2030                2035                2040

Leu Glu  Leu Ala Val Pro Gly  Thr Tyr Arg Ala Asp  Ala Pro Val
    2045                2050                2055

Val Thr  Ile Ala Ser Phe Ser  Arg Gln Leu Leu Val  Ile Thr Ser
    2060                2065                2070

Lys Gln  Arg Pro Arg Lys Leu  Thr Ile His Gly Asn  Asp Gly Glu
    2075                2080                2085

Asp Tyr  Ala Phe Leu Leu Lys  Gly His Glu Asp Leu  Arg Gln Asp
    2090                2095                2100

Glu Arg  Val Met Gln Leu Phe  Gly Leu Val Asn Thr  Leu Leu Glu
    2105                2110                2115

Asn Ser  Arg Lys Thr Ala Glu  Lys Asp Leu Ser Ile  Gln Arg Tyr
    2120                2125                2130

Ser Val  Ile Pro Leu Ser Pro  Asn Ser Gly Leu Ile  Gly Trp Val
    2135                2140                2145

Pro Asn  Cys Asp Thr Leu His  His Leu Ile Arg Glu  Tyr Arg Asp
    2150                2155                2160

Ala Arg  Lys Ile Ile Leu Asn  Gln Glu His Lys His  Met Leu Ser
    2165                2170                2175

Phe Ala  Pro Asn Tyr Asp Asn  Leu Pro Leu Ile Ala  Lys Ile Glu
    2180                2185                2190

Val Phe  Glu Tyr Ala Leu Glu  Asn Thr Glu Gly Asn  Asp Leu Ser
    2195                2200                2205

Arg Val  Leu Trp Leu Lys Ser  Arg Ser Ser Glu Val  Trp Leu Glu
    2210                2215                2220

Arg Arg  Thr Asn Tyr Thr Arg  Ser Leu Ala Val Met  Ser Met Val
    2225                2230                2235

Gly Tyr  Ile Leu Gly Leu Gly  Asp Arg His Pro Ser  Asn Leu Met
    2240                2245                2250

Leu Asp  Arg Tyr Ser Gly Lys  Ile Leu His Ile Asp  Phe Gly Asp
    2255                2260                2265

Cys Phe  Glu Ala Ser Met Asn  Arg Glu Lys Phe Pro  Glu Lys Val
    2270                2275                2280

Pro Phe  Arg Leu Thr Arg Met  Leu Val Lys Ala Met  Glu Val Ser
    2285                2290                2295

Gly Ile  Glu Gly Asn Phe Arg  Ser Thr Cys Glu Asn  Val Met Gln
    2300                2305                2310

Val Leu  Arg Thr Asn Lys Asp  Ser Val Met Ala Met  Met Glu Ala
    2315                2320                2325

Phe Val  His Asp Pro Leu Ile  Asn Trp Arg Leu Phe  Asn Phe Asn
    2330                2335                2340

Glu Val  Pro Gln Leu Ala Leu  Leu Gly Asn Asn Asn  Pro Asn Gly
    2345                2350                2355

Pro Ala  Asn Val Glu Pro Glu  Glu Val Asp Glu Asp  Pro Ala Asp
    2360                2365                2370

Val Asp  Leu Pro Gln Pro Gln  Arg Ser Thr Arg Glu  Lys Glu Ile
    2375                2380                2385

Leu Gln  Ala Val Asn Met Leu  Gly Asp Ala Asn Glu  Val Leu Asn
    2390                2395                2400

Glu Arg  Ala Val Val Val Met  Ala Arg Met Ser His  Lys Leu Thr
    2405                2410                2415
```

```
Gly Arg Asp Phe Ser Thr Ser Ala Val Pro Ser Asn Pro Ile Ala
    2420            2425                2430

Asp His Asn Asn Leu Leu Gly Gly Asp Ser His Glu Val Glu His
2435            2440                2445

Gly Leu Ser Val Lys Val Gln Val Gln Lys Leu Ile Asp Gln Ala
    2450            2455                2460

Thr Ser His Glu Asn Leu Cys Gln Asn Tyr Val Gly Trp Cys Pro
2465            2470                2475

Phe Trp
    2480

<210> SEQ ID NO 5
<211> LENGTH: 1416
<212> TYPE: DNA
<213> ORGANISM: Arabidopsis thaliana

<400> SEQUENCE: 5
atggtttctt ctcagtgttc tgttgcaaac aaaaaccaga ctgggaagcc gtttcagaaa      60
catctatctt tatccatcag ccctccaaaa tctgtcttgg gtgataaccct tgagcttcaa    120 ttctctgatg tctttggacc aatgcctgaa gctaactctg aagaggcctg tgatgttgct    180
tacgacgagc ctgctgttgt ctacagtcga tcccactcat ggttggccc gtctttggtt    240 gttagccatt ctttgaagat gaacaagctc actttacgag aaactgagga ctcagttgac    300
ttggtggagt gtgttgaagg tgaatcgata aagagaacg atgaattctc tggtaatgat    360
gacactgaca gtgagaaatc tccagaggag gtctcaggtg tagtaggcat tgaggacttt    420
gaggtattga aggttgtggg acaaggtgca tttggaaaag tgtaccaggt gaggaaaaaa    480
gacacgtctg agatatacgc gatgaaggtc atgagaaaag ataaaattgt tgagaagaat    540
catgctgaat acatgaaagc cgagcgcgat attctaacca aaatcgatca tcctttcatt    600
gtgcaactta aatactcttt tcagaccaaa tacagattgt atcttgttct tgacttttata   660 aacggaggtc atcttttctt ccagctctat caccaagggc ttttcaggga ggacttggct    720
cgtgtgtaca ctgcagaaat cgtctctgca gtttcccatc tccatgagaa aggcataatg    780
catagagatc ttaaacctga aacatactc atggacgtag atggccatgt gatgttaact    840
gattttggtt tagcaaaaga attttgaagaa aacacaagat caaactccat gtgtgggact    900
acggagtata tggcccctga gattgttcgt ggaaaaggac atgataaggc tgccgactgg    960
tggagtgtag gaatccttct gtatgagatg ctcactggaa agccgccgtt tctcgggagc   1020
aaaggaaaga tacagcagaa aatcgttaag gacaagatca agcttccaca gtttctgtct   1080
aatgaagctc atgccttgct gaagggctg ctgcaaaaag agccagaaag gagactggga    1140
agtggaccga gcggagcaga ggagataaaa aaacacaaat ggttcaaggc gataaactgg    1200
aagaagctgg aggctagaga agtacaacca agtttcaagc cggcggtttc gggaagacaa    1260
tgcatagcta attttgacaa gtgttggact gacatgtctg ttttggattc tccagcaagt    1320
agtcccaact ctgatgctaa ggcgaaccct tttacaaact tcacatacgt caggcctcct   1380
cattcattcc ttcatcggac cacatccaac ttgtag                              1416

<210> SEQ ID NO 6
<211> LENGTH: 471
<212> TYPE: PRT
<213> ORGANISM: Arabidopsis thaliana

<400> SEQUENCE: 6

Met Val Ser Ser Gln Cys Ser Val Ala Asn Lys Asn Gln Thr Gly Lys
```

-continued

```
1               5               10              15

Pro Phe Gln Lys His Leu Ser Leu Ser Ile Ser Pro Pro Lys Ser Val
                20              25              30

Leu Gly Asp Asn Leu Glu Leu Gln Phe Ser Asp Val Phe Gly Pro Met
            35              40              45

Pro Glu Ala Asn Ser Glu Glu Ala Cys Asp Val Ala Tyr Asp Glu Pro
        50              55              60

Ala Val Val Tyr Ser Arg Ser His Ser Leu Val Gly Pro Ser Leu Val
65              70              75              80

Val Ser His Ser Leu Lys Met Asn Lys Leu Thr Leu Arg Glu Thr Glu
                85              90              95

Asp Ser Val Asp Leu Val Glu Cys Val Glu Gly Glu Ser Ile Lys Glu
            100             105             110

Asn Asp Glu Phe Ser Gly Asn Asp Thr Asp Ser Glu Lys Ser Pro
        115             120             125

Glu Glu Val Ser Gly Val Gly Ile Glu Asp Phe Glu Val Leu Lys
    130             135             140

Val Val Gly Gln Gly Ala Phe Gly Lys Val Tyr Gln Val Arg Lys Lys
145             150             155             160

Asp Thr Ser Glu Ile Tyr Ala Met Lys Val Met Arg Lys Asp Lys Ile
                165             170             175

Val Glu Lys Asn His Ala Glu Tyr Met Lys Ala Glu Arg Asp Ile Leu
            180             185             190

Thr Lys Ile Asp His Pro Phe Ile Val Gln Leu Lys Tyr Ser Phe Gln
        195             200             205

Thr Lys Tyr Arg Leu Tyr Leu Val Leu Asp Phe Ile Asn Gly Gly His
    210             215             220

Leu Phe Phe Gln Leu Tyr His Gln Gly Leu Phe Arg Glu Asp Leu Ala
225             230             235             240

Arg Val Tyr Thr Ala Glu Ile Val Ser Ala Val Ser His Leu His Glu
                245             250             255

Lys Gly Ile Met His Arg Asp Leu Lys Pro Glu Asn Ile Leu Met Asp
            260             265             270

Val Asp Gly His Val Met Leu Thr Asp Phe Gly Leu Ala Lys Glu Phe
        275             280             285

Glu Glu Asn Thr Arg Ser Asn Ser Met Cys Gly Thr Thr Glu Tyr Met
    290             295             300

Ala Pro Glu Ile Val Arg Gly Lys Gly His Asp Lys Ala Ala Asp Trp
305             310             315             320

Trp Ser Val Gly Ile Leu Leu Tyr Glu Met Leu Thr Gly Lys Pro Pro
                325             330             335

Phe Leu Gly Ser Lys Gly Lys Ile Gln Gln Lys Ile Val Lys Asp Lys
            340             345             350

Ile Lys Leu Pro Gln Phe Leu Ser Asn Glu Ala His Ala Leu Leu Lys
        355             360             365

Gly Leu Leu Gln Lys Glu Pro Glu Arg Arg Leu Gly Ser Gly Pro Ser
    370             375             380

Gly Ala Glu Glu Ile Lys Lys His Lys Trp Phe Lys Ala Ile Asn Trp
385             390             395             400

Lys Lys Leu Glu Ala Arg Glu Val Gln Pro Ser Phe Lys Pro Ala Val
                405             410             415

Ser Gly Arg Gln Cys Ile Ala Asn Phe Asp Lys Cys Trp Thr Asp Met
            420             425             430
```

Ser Val Leu Asp Ser Pro Ala Ser Ser Pro Asn Ser Asp Ala Lys Ala
        435                 440                 445

Asn Pro Phe Thr Asn Phe Thr Tyr Val Arg Pro Pro His Ser Phe Leu
    450                 455                 460

His Arg Thr Thr Ser Asn Leu
465                 470

<210> SEQ ID NO 7
<211> LENGTH: 1389
<212> TYPE: DNA
<213> ORGANISM: Brassica napus

<400> SEQUENCE: 7

```
atggtctcct ctaaccttac tgtccccaac aaaacccaca agcagcaata tttgtctctc      60
agcccacaag tgtctttatt gaaagatgat gttgagcttg atttctctga tgtgtttggc     120
ccactccctg aagaggccgg agacgttgcc ttcgacgagc ctgctgttat ccacactcgt     180
tcccactctt tggttggacc gtcttcgatc gggagtcatt ctttcaagct cagcaagctt     240
accttactag agactgagga ctctgttgac ttggtggagt gtgttgaacg tgaatcgtca     300
cctttctctg gtactgacga cactgacagc gatggatctc cggagaaaga gtggtggtg      360
aaggtccctg gtgtggttgg acttgatgat ttcgaggtta tgaaggttgt agggaaaggt     420
gcgtttggga agtgtaccag gttaggaaga aggagacgt ctgagatatt cgccatgaag      480
gtcatgagga agataagat catggagaag aaccatgctg agtacatgaa agctgagcgc      540
gatattttaa ccaagattga tcatcccttc attgttcaac ttaaatactc ttttcagact     600
aagtacaggc tgtaccttgt gctagacttt ataaacggag ccatcttttt cttccagctc     660
tatcatcaag gcttttcag ggaggaattg gctcgtgtgt acactgcaga gatcatctct      720
gcagtttctc atctccacga aaaggcata atgcatagag atctcaaacc tgagaacatt      780
ctcatggacg tagacggcca cgtgatgcta actgattttg gtttagcaaa ggagtttgaa     840
gagaacacaa gatcaaactc catgtgtgga actactgagt atatggcacc tgaaattgtt     900
agaggaaaag gtcatgataa ggctgctgat tggtggagcg ttgggattct tctctatgag     960
atgctcactg gaaagccacc gtttcttggg agcaaaggga agattcagca gaaaatagtc    1020
aaggacaaga tcaaacttcc acagtttctg tcaaatgaag ctcatgcgtt gctgaaaggg    1080
ttgttgcaaa aagagccaga gagacgactt ggaagtggtc cgagcggagc agaggagata    1140
aaagggcaca atggttcaa gggaatgaac tggaagaagc tggaggctag agaagtgaag     1200
ccaagtttca gccggaggt gtctggaagg caatgcatag cgaattttga caagtgttgg     1260
actgatatgt ctgtgttgga ttcgccagca agcagtccca gctcggaatc tacggccaac    1320
cctttacca acttcacgta tgtgaggcct cctcattcat tcctcaacca aaccacatcg     1380
acttcgtag                                                            1389
```

<210> SEQ ID NO 8
<211> LENGTH: 462
<212> TYPE: PRT
<213> ORGANISM: Brassica napus

<400> SEQUENCE: 8

Met Val Ser Ser Asn Leu Thr Val Pro Asn Lys Thr His Lys Gln Gln
1               5                   10                  15

Tyr Leu Ser Leu Ser Pro Gln Val Ser Leu Leu Lys Asp Asp Val Glu
            20                  25                  30

Leu Asp Phe Ser Asp Val Phe Gly Pro Leu Pro Glu Glu Ala Gly Asp

-continued

```
                35                  40                  45
Val Ala Phe Asp Glu Pro Ala Val Ile His Thr Arg Ser His Ser Leu
 50                  55                  60
Val Gly Pro Ser Ser Ile Gly Ser His Ser Phe Lys Leu Ser Lys Leu
 65                  70                  75                  80
Thr Leu Leu Glu Thr Glu Asp Ser Val Asp Leu Val Glu Cys Val Glu
                 85                  90                  95
Arg Glu Ser Ser Pro Phe Ser Gly Thr Asp Thr Asp Ser Asp Gly
                100                 105                 110
Ser Pro Glu Lys Asp Val Val Lys Val Pro Gly Val Val Gly Leu
                115                 120                 125
Asp Asp Phe Glu Val Met Lys Val Val Gly Lys Gly Ala Phe Gly Lys
130                 135                 140
Val Tyr Gln Val Arg Lys Lys Glu Thr Ser Glu Ile Phe Ala Met Lys
145                 150                 155                 160
Val Met Arg Lys Asp Lys Ile Met Glu Lys Asn His Ala Glu Tyr Met
                165                 170                 175
Lys Ala Glu Arg Asp Ile Leu Thr Lys Ile Asp His Pro Phe Ile Val
                180                 185                 190
Gln Leu Lys Tyr Ser Phe Gln Thr Lys Tyr Arg Leu Tyr Leu Val Leu
                195                 200                 205
Asp Phe Ile Asn Gly Gly His Leu Phe Phe Gln Leu Tyr His Gln Gly
                210                 215                 220
Leu Phe Arg Glu Glu Leu Ala Arg Val Tyr Thr Ala Glu Ile Ile Ser
225                 230                 235                 240
Ala Val Ser His Leu His Glu Lys Gly Ile Met His Arg Asp Leu Lys
                245                 250                 255
Pro Glu Asn Ile Leu Met Asp Val Asp Gly His Val Met Leu Thr Asp
                260                 265                 270
Phe Gly Leu Ala Lys Glu Phe Glu Glu Asn Thr Arg Ser Asn Ser Met
                275                 280                 285
Cys Gly Thr Thr Glu Tyr Met Ala Pro Glu Ile Val Arg Gly Lys Gly
                290                 295                 300
His Asp Lys Ala Ala Asp Trp Trp Ser Val Gly Ile Leu Leu Tyr Glu
305                 310                 315                 320
Met Leu Thr Gly Lys Pro Pro Phe Leu Gly Ser Lys Gly Lys Ile Gln
                325                 330                 335
Gln Lys Ile Val Lys Asp Lys Ile Lys Leu Pro Gln Phe Leu Ser Asn
                340                 345                 350
Glu Ala His Ala Leu Leu Lys Gly Leu Leu Gln Lys Glu Pro Glu Arg
                355                 360                 365
Arg Leu Gly Ser Gly Pro Ser Gly Ala Glu Glu Ile Lys Gly His Lys
                370                 375                 380
Trp Phe Lys Gly Met Asn Trp Lys Lys Leu Glu Ala Arg Glu Val Lys
385                 390                 395                 400
Pro Ser Phe Lys Pro Glu Val Ser Gly Arg Gln Cys Ile Ala Asn Phe
                405                 410                 415
Asp Lys Cys Trp Thr Asp Met Ser Val Leu Asp Ser Pro Ala Ser Ser
                420                 425                 430
Pro Ser Ser Glu Ser Thr Ala Asn Pro Phe Thr Asn Phe Thr Tyr Val
                435                 440                 445
Arg Pro Pro His Ser Phe Leu Asn Gln Thr Thr Ser Thr Ser
450                 455                 460
```

<210> SEQ ID NO 9
<211> LENGTH: 873
<212> TYPE: DNA
<213> ORGANISM: Arabidopsis thaliana

<400> SEQUENCE: 9

```
atggagacgg tggtcgataa agatgttctg aagtcttccg gggctgagct tcttcccgac    60
ggacgtcgag gtttacgcat ccatgactgg gagatcgaaa ccctccgcgg cacgattctc   120
acttctctcg ctgtcgaaga gtgggaaaaa aagcttaaga catctcactt acctgaaatg   180
gtttttggcg agaatgcatt agtccttaaa cacttaggta gcaacactaa gattcatttt   240
aatgcgtttg acgcactagc tggttggaag caggaagggc ttccacctgt tgaagttcct   300
gctgcagcac aatggaaatt caggagcaag ccgtctcagc aggtgatact agattatgat   360
tacacgttta caacgccata ctgtggaagt gaagtagttg agaaagacaa agaaacggtt   420
gaggcaaaag ctaatccaaa gggggaagct actcttcagt gggagaactg tgaagatcag   480
attgatttgg ctgctctctc acttaaagaa cctattctct tctatgatga ggtagttttg   540
tatgaagata aactggctga caatggagtg tcacttctga ctgtgaaagt gagagtcatg   600
ccaagctcat ggttcctcct cttgcgattt tggctgagag ttgatggtgt gcttatgaga   660
ttgagagaga cgagaatgca ttataggttt ggcgaagatg aggcaccaac tgttcttcgt   720
gaaaactgtt ggagagaagc aacatttcag tctctatctg cgaaagggta tccagttgac   780
ttagcagtct ggagcgaccc gagctccatc agtcagaggc ttccagtgat taagcatacg   840
acacagaaac tgaagatccc tagtaaagtt taa                                873
```

<210> SEQ ID NO 10
<211> LENGTH: 290
<212> TYPE: PRT
<213> ORGANISM: Arabidopsis thaliana

<400> SEQUENCE: 10

```
Met Glu Thr Val Val Asp Lys Asp Val Leu Lys Ser Ser Gly Ala Glu
1               5                   10                  15

Leu Leu Pro Asp Gly Arg Arg Gly Leu Arg Ile His Asp Trp Glu Ile
            20                  25                  30

Glu Thr Leu Arg Gly Thr Ile Leu Thr Ser Leu Ala Val Glu Glu Trp
        35                  40                  45

Glu Lys Lys Leu Lys Thr Ser His Leu Pro Glu Met Val Phe Gly Glu
    50                  55                  60

Asn Ala Leu Val Leu Lys His Leu Gly Ser Asn Thr Lys Ile His Phe
65                  70                  75                  80

Asn Ala Phe Asp Ala Leu Ala Gly Trp Lys Gln Glu Gly Leu Pro Pro
                85                  90                  95

Val Glu Val Pro Ala Ala Ala Gln Trp Lys Phe Arg Ser Lys Pro Ser
            100                 105                 110

Gln Gln Val Ile Leu Asp Tyr Asp Tyr Thr Phe Thr Thr Pro Tyr Cys
        115                 120                 125

Gly Ser Glu Val Val Glu Lys Asp Lys Glu Thr Val Glu Ala Lys Ala
    130                 135                 140

Asn Pro Lys Gly Glu Ala Thr Leu Gln Trp Glu Asn Cys Glu Asp Gln
145                 150                 155                 160

Ile Asp Leu Ala Ala Leu Ser Leu Lys Glu Pro Ile Leu Phe Tyr Asp
                165                 170                 175

Glu Val Val Leu Tyr Glu Asp Glu Leu Ala Asp Asn Gly Val Ser Leu
```

```
                    180              185                190
Leu Thr Val Lys Val Arg Val Met Pro Ser Ser Trp Phe Leu Leu Leu
                195                  200                205

Arg Phe Trp Leu Arg Val Asp Gly Val Leu Met Arg Leu Arg Glu Thr
        210                  215                  220

Arg Met His Tyr Arg Phe Gly Glu Asp Glu Ala Pro Thr Val Leu Arg
225                 230                  235                 240

Glu Asn Cys Trp Arg Glu Ala Thr Phe Gln Ser Leu Ser Ala Lys Gly
                245                  250                  255

Tyr Pro Val Asp Leu Ala Val Trp Ser Asp Pro Ser Ser Ile Ser Gln
            260                  265                  270

Arg Leu Pro Val Ile Lys His Thr Thr Gln Lys Leu Lys Ile Pro Ser
        275                  280                  285

Lys Val
    290

<210> SEQ ID NO 11
<211> LENGTH: 873
<212> TYPE: DNA
<213> ORGANISM: Brassica napus

<400> SEQUENCE: 11
atggagacgg aggtcgataa ggagattcta aaatctgccg gagctgagct tcttcccgac      60
ggacgtaaag gcttacgaat ccatgactgg gagatcgaaa ccatccgcgg cacgattctc     120
acttctctcg ctcacgaaca gtgggaagag aagcttaaga cctctcactt acctgaaatg     180
gtctttggcg agaatgcgtt agtgcttaaa cacttgagca gcaacacgaa gattcatttt     240
aacgcctttg atgcacttgc gggttggagg caagaagggc ttccacctgt tgaggttcct     300
gctgctgcaa atggaagttt caggagcaag ccgtctcagc aggtgatact ggattatgat     360
tacactttta ctacgccgta ctctggtagc ggagttgttg agaaagacca agaaacggtt     420
gaggccaaag caaatactga gggggaagat agtcttaagt gggagaactg tgaagagcag     480
attgatttgg ctgctctttc acttaaagaa cctattctct ctatgacgga ggtagttttg     540
tatgaagatg aactggctga caatggagtg tcacttctga ctgtgaaagt gagagtcatg     600
ccaagttcat ggttcctccc cttacgattt tggcttagag ttgatggtgt gcttatgagg     660
ttgagagaga cgagaatgca ttatgtcttt ggcaaagggg agacacccac agttcttcgt     720
gaaagctgtt ggagagaaac aacatttaag tctctatctg cgaaagggta tccagttgat     780
ttagcagtct atagcgaccc aggccccatc agtcagaggc ttccggtgat taagcagata     840
acacagaaac tgatgattcc tcataaagta taa                                  873

<210> SEQ ID NO 12
<211> LENGTH: 290
<212> TYPE: PRT
<213> ORGANISM: Brassica napus

<400> SEQUENCE: 12

Met Glu Thr Glu Val Asp Lys Glu Ile Leu Lys Ser Ala Gly Ala Glu
1               5                   10                  15

Leu Leu Pro Asp Gly Arg Lys Gly Leu Arg Ile His Asp Trp Glu Ile
            20                  25                  30

Glu Thr Ile Arg Gly Thr Ile Leu Thr Ser Leu Ala His Glu Gln Trp
        35                  40                  45

Glu Glu Lys Leu Lys Thr Ser His Leu Pro Glu Met Val Phe Gly Glu
    50                  55                  60
```

Asn Ala Leu Val Leu Lys His Leu Ser Ser Asn Thr Lys Ile His Phe
65                  70                  75                  80

Asn Ala Phe Asp Ala Leu Ala Gly Trp Arg Gln Glu Gly Leu Pro Pro
                85                  90                  95

Val Glu Val Pro Ala Ala Ala Lys Trp Lys Phe Arg Ser Lys Pro Ser
            100                 105                 110

Gln Gln Val Ile Leu Asp Tyr Asp Tyr Thr Phe Thr Thr Pro Tyr Ser
        115                 120                 125

Gly Ser Gly Val Val Glu Lys Asp Gln Glu Thr Val Glu Ala Lys Ala
    130                 135                 140

Asn Thr Glu Gly Glu Asp Ser Leu Lys Trp Glu Asn Cys Glu Glu Gln
145                 150                 155                 160

Ile Asp Leu Ala Ala Leu Ser Leu Lys Glu Pro Ile Leu Phe Tyr Asp
                165                 170                 175

Glu Val Val Leu Tyr Glu Asp Glu Leu Ala Asp Asn Gly Val Ser Leu
            180                 185                 190

Leu Thr Val Lys Val Arg Val Met Pro Ser Ser Trp Phe Leu Pro Leu
        195                 200                 205

Arg Phe Trp Leu Arg Val Asp Gly Val Leu Met Arg Leu Arg Glu Thr
210                 215                 220

Arg Met His Tyr Val Phe Gly Lys Gly Glu Thr Pro Thr Val Leu Arg
225                 230                 235                 240

Glu Ser Cys Trp Arg Glu Thr Thr Phe Lys Ser Leu Ser Ala Lys Gly
                245                 250                 255

Tyr Pro Val Asp Leu Ala Val Tyr Ser Asp Pro Gly Pro Ile Ser Gln
            260                 265                 270

Arg Leu Pro Val Ile Lys Gln Ile Thr Gln Lys Leu Met Ile Pro His
        275                 280                 285

Lys Val
    290

<210> SEQ ID NO 13
<211> LENGTH: 1035
<212> TYPE: DNA
<213> ORGANISM: Arabidopsis thaliana

<400> SEQUENCE: 13
atggcgagtc aaacaccgaa tctcgagtgt cggatgtacg aggcgaaata cccagaggtg    60
gatatgcggt gatgatcca ggtgaagaac attgccgata tgggagctta tgtttctctc   120
ctcgagtaca caacatcga aggcatgatc cttttctccg agctctctcg tcgtcggatc   180
cgaagtgtta gcagtttgat taaggtcgga agaattgagc ctgtcatggt tctccgtgtt   240
gacaaagaga aggttacat tgatctgagc aaacgtagag tcagcgagga agatattcag   300
acttgtgaag agaggtataa caagagcaaa cttgttcatt ctatcatgcg ccatgttgct   360
gagactcttt caattgattt ggaggacttg tatgtgaaca ttggttggcc tttgtatcga   420
cgacatggtc atgcttttga ggctttcaag atcttagtga cggatcctga ttcagtgttg   480
ggtcctctca cccgtgagat caaagaagtt gggcctgatg gcaagaggt gactaaggtt   540 gtacctgctg ttacggaaga agtgaaagat gcacttgtga agaacattag gaggagaatg   600
acaccacaac caatgaaaat ccgggctgat atcgaattga agtgttttca gtttgatgga   660
gttgttcaca ttaaggaggc tatgaaaaat gctgaagccg ctggaaatga agactgtcct   720
gttaagatta aattggttgc tccacctctg tatgtcctta ctactcagac acttgacaag   780

```
gaacaaggga ttgaaattct aaacaaagcc atagcagcat gcactgagac aattgagaca    840
cacaaaggca agcttgtcgt taaggagggg gctagagctg tgagtgaacg tgatgaaaag    900
atgctgacag aacacatggc taagctacgt cttgacaatg aagaaatgag cggcgatgaa    960
gatagcggag acgaagaaga ggacactggt atgggcgaag tggatctcga tgcaggtgcc   1020
ggaatcatcg agtaa                                                    1035
```

<210> SEQ ID NO 14
<211> LENGTH: 344
<212> TYPE: PRT
<213> ORGANISM: Arabidopsis thaliana

<400> SEQUENCE: 14

```
Met Ala Ser Gln Thr Pro Asn Leu Glu Cys Arg Met Tyr Glu Ala Lys
1               5                   10                  15

Tyr Pro Glu Val Asp Met Ala Val Met Ile Gln Val Lys Asn Ile Ala
                20                  25                  30

Asp Met Gly Ala Tyr Val Ser Leu Leu Glu Tyr Asn Asn Ile Glu Gly
            35                  40                  45

Met Ile Leu Phe Ser Glu Leu Ser Arg Arg Ile Arg Ser Val Ser
    50                  55                  60

Ser Leu Ile Lys Val Gly Arg Ile Glu Pro Val Met Val Leu Arg Val
65                  70                  75                  80

Asp Lys Glu Lys Gly Tyr Ile Asp Leu Ser Lys Arg Val Ser Glu
                85                  90                  95

Glu Asp Ile Gln Thr Cys Glu Glu Arg Tyr Asn Lys Ser Lys Leu Val
            100                 105                 110

His Ser Ile Met Arg His Val Ala Glu Thr Leu Ser Ile Asp Leu Glu
        115                 120                 125

Asp Leu Tyr Val Asn Ile Gly Trp Pro Leu Tyr Arg Arg His Gly His
    130                 135                 140

Ala Phe Glu Ala Phe Lys Ile Leu Val Thr Asp Pro Asp Ser Val Leu
145                 150                 155                 160

Gly Pro Leu Thr Arg Glu Ile Lys Glu Val Gly Pro Asp Gly Gln Glu
                165                 170                 175

Val Thr Lys Val Val Pro Ala Val Thr Glu Glu Val Lys Asp Ala Leu
            180                 185                 190

Val Lys Asn Ile Arg Arg Arg Met Thr Pro Gln Pro Met Lys Ile Arg
        195                 200                 205

Ala Asp Ile Glu Leu Lys Cys Phe Gln Phe Asp Gly Val Val His Ile
    210                 215                 220

Lys Glu Ala Met Lys Asn Ala Glu Ala Ala Gly Asn Glu Asp Cys Pro
225                 230                 235                 240

Val Lys Ile Lys Leu Val Ala Pro Pro Leu Tyr Val Leu Thr Thr Gln
                245                 250                 255

Thr Leu Asp Lys Glu Gln Gly Ile Glu Ile Leu Asn Lys Ala Ile Ala
            260                 265                 270

Ala Cys Thr Glu Thr Ile Glu Thr His Lys Gly Lys Leu Val Val Lys
        275                 280                 285

Glu Gly Ala Arg Ala Val Ser Glu Arg Asp Glu Lys Met Leu Thr Glu
    290                 295                 300

His Met Ala Lys Leu Arg Leu Asp Asn Glu Glu Met Ser Gly Asp Glu
305                 310                 315                 320

Asp Ser Gly Asp Glu Glu Glu Asp Thr Gly Met Gly Glu Val Asp Leu
                325                 330                 335
```

Asp Ala Gly Ala Gly Ile Ile Glu
            340

<210> SEQ ID NO 15
<211> LENGTH: 1035
<212> TYPE: DNA
<213> ORGANISM: Brassica napus

<400> SEQUENCE: 15
atggcgagtc aaaccccgaa tctagagtgc cggatgtacg aagccaagta cccagaagtc      60
gacatggctg tgatgatcca agtcaagaac atcgccgaca tgggagccta cgtgtccctc     120
ctcgagtaca caacatcga aggcatgatc ctcttctccg agctctcccg ccgtcggatc     180
cggagtgtga gcagcttgat caaggtcggg agaatcgagc ccgtcatggt cctgcgtgtg     240
gataaagaga aaggttacat tgatctgagc aaacgtagag ttagtgagga agatattcag     300
acttgtgaag agaggtataa caagagcaag ctcgttcatt ctatcatgcg tcatgtcgct     360
gagactcttt ctatcgattt ggaggagttg tatgtgaaca ttgggtggcc tttgtaccgg     420
aaacatggtc atgcttttga ggctttcaag atcttagtga ctgatcctga ttcagtgttg     480
ggttcactca cacgtgaggt caaagaagtt gggcctgatg ggcaggaggt gactaaagtt     540
gtacctgctg ttacggaaga agtgaaggat gctcttgtga agaacattag gaggaggatg     600
acaccacaac cgatgaaaat ccgtgctgat atcgagttga atgttttca gtttgacgga     660
gttgtccaca tcaaggaggc catgagaaag gctgaagctg ctggaaacga tgactgtcct     720
gtgaagatta gttggttgc tccgcctctt tatgtcctta ctactcagac tcttgacaag     780
gaccaaggga ttaaaattct agacgaggcc atagtagctt gcactgagac aattgagaaa     840
cacaaaggca agcttgtcgt taaggaggca cctagagccg tgagtgaaag agatgataag     900
atgctgacag aacacatggc taagctaaga atggacaatg aagaaattag cggcgatgaa     960
gagagtggag aggaagaaga ggacacaggg atgggcgacg ttgatatcga cggtggcgcc    1020
ggaatcattg agtag                                                    1035

<210> SEQ ID NO 16
<211> LENGTH: 344
<212> TYPE: PRT
<213> ORGANISM: Brassica napus

<400> SEQUENCE: 16

Met Ala Ser Gln Thr Pro Asn Leu Glu Cys Arg Met Tyr Glu Ala Lys
1               5                  10                  15

Tyr Pro Glu Val Asp Met Ala Val Met Ile Gln Val Lys Asn Ile Ala
            20                  25                  30

Asp Met Gly Ala Tyr Val Ser Leu Leu Glu Tyr Asn Asn Ile Glu Gly
        35                  40                  45

Met Ile Leu Phe Ser Glu Leu Ser Arg Arg Ile Arg Ser Val Ser
    50                  55                  60

Ser Leu Ile Lys Val Gly Arg Ile Glu Pro Val Met Val Leu Arg Val
65                  70                  75                  80

Asp Lys Glu Lys Gly Tyr Ile Asp Leu Ser Lys Arg Val Ser Glu
            85                  90                  95

Glu Asp Ile Gln Thr Cys Glu Glu Arg Tyr Asn Lys Ser Lys Leu Val
            100                 105                 110

His Ser Ile Met Arg His Val Ala Glu Thr Leu Ser Ile Asp Leu Glu
        115                 120                 125

| Glu | Leu | Tyr | Val | Asn | Ile | Gly | Trp | Pro | Leu | Tyr | Arg | Lys | His | Gly | His |
| | 130 | | | | 135 | | | | 140 | | | | | | |

| Ala | Phe | Glu | Ala | Phe | Lys | Ile | Leu | Val | Thr | Asp | Pro | Asp | Ser | Val | Leu |
| 145 | | | | 150 | | | | | 155 | | | | | | 160 |

| Gly | Ser | Leu | Thr | Arg | Glu | Val | Lys | Glu | Val | Gly | Pro | Asp | Gly | Gln | Glu |
| | | | 165 | | | | | 170 | | | | | 175 | | |

| Val | Thr | Lys | Val | Val | Pro | Ala | Val | Thr | Glu | Glu | Val | Lys | Asp | Ala | Leu |
| | | | 180 | | | | | 185 | | | | | 190 | | |

| Val | Lys | Asn | Ile | Arg | Arg | Arg | Met | Thr | Pro | Gln | Pro | Met | Lys | Ile | Arg |
| | | 195 | | | | | 200 | | | | | 205 | | | |

| Ala | Asp | Ile | Glu | Leu | Lys | Cys | Phe | Gln | Phe | Asp | Gly | Val | Val | His | Ile |
| | 210 | | | | | 215 | | | | | 220 | | | | |

| Lys | Glu | Ala | Met | Arg | Lys | Ala | Glu | Ala | Ala | Gly | Asn | Asp | Asp | Cys | Pro |
| 225 | | | | | 230 | | | | | 235 | | | | | 240 |

| Val | Lys | Ile | Lys | Leu | Val | Ala | Pro | Pro | Leu | Tyr | Val | Leu | Thr | Thr | Gln |
| | | | | 245 | | | | | 250 | | | | | 255 | |

| Thr | Leu | Asp | Lys | Asp | Gln | Gly | Ile | Lys | Ile | Leu | Asp | Glu | Ala | Ile | Val |
| | | | 260 | | | | | 265 | | | | | 270 | | |

| Ala | Cys | Thr | Glu | Thr | Ile | Glu | Lys | His | Lys | Gly | Lys | Leu | Val | Val | Lys |
| | | 275 | | | | | 280 | | | | | 285 | | | |

| Glu | Ala | Pro | Arg | Ala | Val | Ser | Glu | Arg | Asp | Asp | Lys | Met | Leu | Thr | Glu |
| | 290 | | | | | 295 | | | | | 300 | | | | |

| His | Met | Ala | Lys | Leu | Arg | Met | Asp | Asn | Glu | Glu | Ile | Ser | Gly | Asp | Glu |
| 305 | | | | | 310 | | | | | 315 | | | | | 320 |

| Glu | Ser | Gly | Glu | Glu | Glu | Glu | Asp | Thr | Gly | Met | Gly | Asp | Val | Asp | Ile |
| | | | | 325 | | | | | 330 | | | | | 335 | |

| Asp | Gly | Gly | Ala | Gly | Ile | Ile | Glu |
| | | | | 340 | | | |

<210> SEQ ID NO 17
<211> LENGTH: 1476
<212> TYPE: DNA
<213> ORGANISM: Arabidopsis thaliana

<400> SEQUENCE: 17

```
atgttggcaa tggagaaaga atttgattca aagcttgttc ttcaagggaa ctcatccaac    60
ggtgctaatg tttctagaag caaaagcttc tcctttaaag ctcctcaaga aaatttcacc   120
agccatgatt tcgaatttgg caagatctat ggtgttggtt cttactctaa ggttgttagg   180
gcaaagaaga aggaaactgg aactgtgtat gctttaaaga ttatggacaa aaagtttatc   240
accaaggaga ataaaactgc ttatgtgaaa ttggaaagga ttgttcttga tcaacttgaa   300
catcctggga tcattaaact ttacttcacg tttcaagaca catcctcact atatatggca   360
cttgaatctt gtgagggtgg cgagcttttc gaccaaataa ccagaaaagg tcggctatcg   420
gaggatgaag ctcggttcta cactgcagaa gttgtggatg ctcttgagta tacacatagt   480
atgggactga ttcatcgaga tattaagccg gagaatctgt tgctgacttc agatggacac   540
attaagattg cggattttgg aagtgtaaag ccgatgcagg atagccagat cacagttcta   600
cctaatgcag cttctgacga taaggcgtgc acttttgtcg ggactgctgc atatgttcct   660
ccagaagttc tcaactcctc tcccgcaact ttcgggaatg atctttgggc tctcggctgc   720
actctctatc agatgctttc ggggacttcc ccatttaaag atgcaagtga atggctgatt   780
ttccaaagaa tttagccag agatataaag ttcccaaatc atttttcaga agcagcaaga   840
gacctcatcg accggttgct ggataccgag ccaagcagaa ggccaggtgc tggctcagaa   900
```

-continued

```
ggttatgttg ctcttaagag acatcctttc tttaatggag ttgactggaa gaatctaagg    960
tcccagactc ctccaaaact agctccagat cctgcgtctc agacagcatc tcccgagagg   1020
gatgacacac atggttctcc atggaacctg acacatattg agattctttt agccacacag   1080
aacgaggggc acagtgctcc tcctacatct tctgaatcat cgggttccat aactcgactt   1140
gcttcaatag actcttttga ttcaagatgg caacagtttt tagagccagg agaatcggtt   1200
ctgatgatat cagcggtgaa gaagcttcag aaaataacga gcaagaaggt gcagctaata   1260
ctcaccaaca aacccaagct gatctatgtc gacccgtcaa aactagttgt gaaaggaaac   1320
attatatggt ctgataactc gaatgacctc aacgttgtag tcactagccc ttcacatttc   1380
aagatttgca cgccaaagaa ggttttatca tttgaagacg caaacagag agcttcagtg    1440
tggaaaaagg caatcgagac tcttcagaac cgctga                             1476
```

<210> SEQ ID NO 18
<211> LENGTH: 491
<212> TYPE: PRT
<213> ORGANISM: Arabidopsis thaliana

<400> SEQUENCE: 18

```
Met Leu Ala Met Glu Lys Glu Phe Asp Ser Lys Leu Val Leu Gln Gly
 1               5                  10                  15

Asn Ser Ser Asn Gly Ala Asn Val Ser Arg Ser Lys Ser Phe Ser Phe
             20                  25                  30

Lys Ala Pro Gln Glu Asn Phe Thr Ser His Asp Phe Glu Phe Gly Lys
         35                  40                  45

Ile Tyr Gly Val Gly Ser Tyr Ser Lys Val Val Arg Ala Lys Lys Lys
     50                  55                  60

Glu Thr Gly Thr Val Tyr Ala Leu Lys Ile Met Asp Lys Lys Phe Ile
 65                  70                  75                  80

Thr Lys Glu Asn Lys Thr Ala Tyr Val Lys Leu Glu Arg Ile Val Leu
                 85                  90                  95

Asp Gln Leu Glu His Pro Gly Ile Ile Lys Leu Tyr Phe Thr Phe Gln
            100                 105                 110

Asp Thr Ser Ser Leu Tyr Met Ala Leu Glu Ser Cys Glu Gly Gly Glu
        115                 120                 125

Leu Phe Asp Gln Ile Thr Arg Lys Gly Arg Leu Ser Glu Asp Glu Ala
    130                 135                 140

Arg Phe Tyr Thr Ala Glu Val Val Asp Ala Leu Glu Tyr Ile His Ser
145                 150                 155                 160

Met Gly Leu Ile His Arg Asp Ile Lys Pro Glu Asn Leu Leu Leu Thr
                165                 170                 175

Ser Asp Gly His Ile Lys Ile Ala Asp Phe Gly Ser Val Lys Pro Met
            180                 185                 190

Gln Asp Ser Gln Ile Thr Val Leu Pro Asn Ala Ala Ser Asp Asp Lys
        195                 200                 205

Ala Cys Thr Phe Val Gly Thr Ala Ala Tyr Val Pro Pro Glu Val Leu
    210                 215                 220

Asn Ser Ser Pro Ala Thr Phe Gly Asn Asp Leu Trp Ala Leu Gly Cys
225                 230                 235                 240

Thr Leu Tyr Gln Met Leu Ser Gly Thr Ser Pro Phe Lys Asp Ala Ser
                245                 250                 255

Glu Trp Leu Ile Phe Gln Arg Ile Ile Ala Arg Asp Ile Lys Phe Pro
            260                 265                 270

Asn His Phe Ser Glu Ala Ala Arg Asp Leu Ile Asp Arg Leu Leu Asp
```

275                 280                 285
Thr Glu Pro Ser Arg Arg Pro Gly Ala Gly Ser Glu Gly Tyr Val Ala
            290                 295                 300
Leu Lys Arg His Pro Phe Phe Asn Gly Val Asp Trp Lys Asn Leu Arg
305                 310                 315                 320
Ser Gln Thr Pro Pro Lys Leu Ala Pro Asp Pro Ala Ser Gln Thr Ala
            325                 330                 335
Ser Pro Glu Arg Asp Asp Thr His Gly Ser Pro Trp Asn Leu Thr His
            340                 345                 350
Ile Gly Asp Ser Leu Ala Thr Gln Asn Glu Gly His Ser Ala Pro Pro
            355                 360                 365
Thr Ser Ser Glu Ser Ser Gly Ser Ile Thr Arg Leu Ala Ser Ile Asp
            370                 375                 380
Ser Phe Asp Ser Arg Trp Gln Gln Phe Leu Glu Pro Gly Glu Ser Val
385                 390                 395                 400
Leu Met Ile Ser Ala Val Lys Lys Leu Gln Lys Ile Thr Ser Lys Lys
                405                 410                 415
Val Gln Leu Ile Leu Thr Asn Lys Pro Lys Leu Ile Tyr Val Asp Pro
            420                 425                 430
Ser Lys Leu Val Val Lys Gly Asn Ile Ile Trp Ser Asp Asn Ser Asn
            435                 440                 445
Asp Leu Asn Val Val Val Thr Ser Pro Ser His Phe Lys Ile Cys Thr
            450                 455                 460
Pro Lys Lys Val Leu Ser Phe Glu Asp Ala Lys Gln Arg Ala Ser Val
465                 470                 475                 480
Trp Lys Lys Ala Ile Glu Thr Leu Gln Asn Arg
                485                 490

<210> SEQ ID NO 19
<211> LENGTH: 1471
<212> TYPE: DNA
<213> ORGANISM: Brassica napus

<400> SEQUENCE: 19
atgttggcaa tggagaaaga atttgattca aagcttgtcc ttcaaggcaa tggcggaagt      60
gtctcgagaa gcaagagctt ctccttcaaa gctccccaag agaatttcac catccaggac     120
ttccagctcg gcaagatcta cggcgttggc tcttactcta aggttgttag ggcaaagaag     180
aaggaaagtg gaactgtgta tgcgttaaag attatggaca aaaagtttat caccaaggag     240
aacaaaacag cttatgtgaa gctcgagagg attgttcttg atcagcttga tcatccggga     300
atcatcaaac ccttcttcac tttttcaagac tccttctctc tatatatggc acttgaatct     360
tgcgagggtg gcgagctttt cgaccaaatt actagaaaag gtaggctatc tgaggaagaa     420
gctaggttct acagtgcaca agttgtggat gctcttgagt atatacatag tatgggactc     480
atacatcgtg atatcaagcc ggagaatctg ttgctgactt cagatgggca catcaagatt     540
gcggattttg aagtgtgaa gccgatgcaa gatagcagga tcaaagtgct tcctaatgct     600
gcttctgacg ataaggcgtg cactttttgtc ggaactgctg cttatgttcc tcctgaggtt     660
ctcaactcat ctccagcaac ttttggaaat gatctctggg ctctgggctg cactatctac     720
caaatgcttt cagggacttc cccattcaaa gacgcaagtg aatggctgat ttttcaagaa    780
attatagcct gggatataaa gttcccaagt catttctcag aagcagcaag agacctcatt     840
gaccggttgc tggatacaga tccaagcaga agaccaggtg ctgggtcaga aggttatgct     900
gctcttaaga gacatccttt ctttatggga gttgactgga agaatctaag gtctcagact     960

```
cctccaaaac tagccccaga tcctgcgtct cagacagcat ctccggagag ggaagacgct    1020
catggttctt ctccatggaa cccgactcat attggagatt cttcagctgc acataacgat    1080
gggcacagtg ctccttctac accttctgaa tcatcatcga gttccataac acggcttgct    1140
tcaatagact cttttgattc gagatggcaa cagtttctgg agccgggaga atcggtcctg    1200
atgatatcag cagtgaagaa gcttcagaaa ataacgagca agaaggtgca gctaatacta    1260
accaacaaac ccaagctaat ctatgttgac ccgtcgaagc tagttgtgaa agggaacatc    1320
atctggtctg ataactcgaa tgacctcaac gttgtagtca ctagcccttc tcatttcaag    1380
atttgcacgc caagaaggt tttgtcattt gaagacgtga acagagagc tttggtgtgg     1440 aaaaaggcaa tcgagactct tcagaacctg a                                  1471
```

<210> SEQ ID NO 20
<211> LENGTH: 490
<212> TYPE: PRT
<213> ORGANISM: Brassica napus

<400> SEQUENCE: 20

```
Met Leu Ala Met Glu Lys Glu Phe Asp Ser Lys Leu Val Leu Gln Gly
1               5                   10                  15

Asn Gly Gly Ser Val Ser Arg Ser Lys Ser Phe Ser Phe Lys Ala Pro
            20                  25                  30

Gln Glu Asn Phe Thr Ile Gln Asp Phe Gln Leu Gly Lys Ile Tyr Gly
        35                  40                  45

Val Gly Ser Tyr Ser Lys Val Val Arg Ala Lys Lys Glu Ser Gly
    50                  55                  60

Thr Val Tyr Ala Leu Lys Ile Met Asp Lys Lys Phe Ile Thr Lys Glu
65                  70                  75                  80

Asn Lys Thr Ala Tyr Val Lys Leu Glu Arg Ile Val Leu Asp Gln Leu
                85                  90                  95

Asp His Pro Gly Ile Ile Lys Pro Phe Phe Thr Phe Gln Asp Ser Phe
            100                 105                 110

Ser Leu Tyr Met Ala Leu Glu Ser Cys Glu Gly Gly Glu Leu Phe Asp
        115                 120                 125

Gln Ile Thr Arg Lys Gly Arg Leu Ser Glu Glu Glu Ala Arg Phe Tyr
    130                 135                 140

Ser Ala Gln Val Val Asp Ala Leu Glu Tyr Ile His Ser Met Gly Leu
145                 150                 155                 160

Ile His Arg Asp Ile Lys Pro Glu Asn Leu Leu Thr Ser Asp Gly
                165                 170                 175

His Ile Lys Ile Ala Asp Phe Gly Ser Val Lys Pro Met Gln Asp Ser
            180                 185                 190

Arg Ile Lys Val Leu Pro Asn Ala Ala Ser Asp Lys Ala Cys Thr
    195                 200                 205

Phe Val Gly Thr Ala Ala Tyr Val Pro Pro Glu Val Leu Asn Ser Ser
210                 215                 220

Pro Ala Thr Phe Gly Asn Asp Leu Trp Ala Leu Gly Cys Thr Ile Tyr
225                 230                 235                 240

Gln Met Leu Ser Gly Thr Ser Pro Phe Lys Asp Ala Ser Glu Trp Leu
                245                 250                 255

Ile Phe Gln Arg Ile Ile Ala Trp Asp Ile Lys Phe Pro Ser His Phe
            260                 265                 270

Ser Glu Ala Ala Arg Asp Leu Ile Asp Arg Leu Leu Asp Thr Asp Pro
        275                 280                 285
```

```
Ser Arg Arg Pro Gly Ala Gly Ser Glu Gly Tyr Ala Ala Leu Lys Arg
    290                 295                 300

His Pro Phe Phe Met Gly Val Asp Trp Lys Asn Leu Arg Ser Gln Thr
305                 310                 315                 320

Pro Pro Lys Leu Ala Pro Asp Pro Ala Ser Gln Thr Ala Ser Pro Glu
                325                 330                 335

Arg Glu Asp Ala His Gly Ser Ser Pro Trp Asn Pro Thr His Ile Gly
            340                 345                 350

Asp Ser Ser Ala Ala His Asn Asp Gly His Ser Ala Pro Ser Thr Pro
        355                 360                 365

Ser Glu Ser Ser Ser Ser Ser Ile Thr Arg Leu Ala Ser Ile Asp Ser
    370                 375                 380

Phe Asp Ser Arg Trp Gln Gln Phe Leu Glu Pro Gly Glu Ser Val Leu
385                 390                 395                 400

Met Ile Ser Ala Val Lys Lys Leu Gln Lys Ile Thr Ser Lys Lys Val
                405                 410                 415

Gln Leu Ile Leu Thr Asn Lys Pro Lys Leu Ile Tyr Val Asp Pro Ser
            420                 425                 430

Lys Leu Val Val Lys Gly Asn Ile Ile Trp Ser Asp Asn Ser Asn Asp
        435                 440                 445

Leu Asn Val Val Thr Ser Pro Ser His Phe Lys Ile Cys Thr Pro
    450                 455                 460

Lys Lys Val Leu Ser Phe Glu Asp Val Lys Gln Arg Ala Leu Val Trp
465                 470                 475                 480

Lys Lys Ala Ile Glu Thr Leu Gln Asn Leu
                485                 490

<210> SEQ ID NO 21
<211> LENGTH: 954
<212> TYPE: DNA
<213> ORGANISM: Arabidopsis thaliana

<400> SEQUENCE: 21
atggcagagg aaattccagc aacagcatca ttcactccat acgtccattc acaaactcta      60
acatctcaca atcgcgccgt ctcctccgtg aaattctcct ccgatggacg tctcctcgca     120
tccgcctccg ccgacaaaac aatccgcact acacaatca acaccattaa cgatccaatc      180
gccgagcccg tacaagaatt caccggccat gaaaacggta tctccgatgt tgcattctct     240
tcagacgcga ggtttatagt ctcagcttcc gatgacaaaa ccttaaagct atgggacgtt     300
gaaactggtt cattgatcaa gacgcttatt ggacacacta ttacgccctt ctgtgtcaat     360
ttcaatcctc aatcaaatat gattgtatct ggttcgtttg atgaaactgt tcggatctgg     420
gatgtcacta ctggaaagtg tttgaaagtt cttcccgcgc attctgatcc tgttactgct     480
gttgatttta atagagatgg gtctctcatt gtttcgagta gctatgatgg ttgtgtcgt      540 atatgggatt ctgggactgg tcattgtgtg aaaactctga ttgatgatga aatcctcct      600 gtttcgtttg ttagattctc tcctaatggc aagtttatcc tcgttggtac acttgataac     660
acgctgaggt tgtggaacat ttcgtctgct aagttcctca aacatacac tggccacgtg      720 aacgcacagt attgcatttc ctctgcgttc tccgtcacaa atggaaagcg aatagtcagt     780
ggatccgagg acaactgtgt acacatgtgg gagctaaact ccaagaaact gctacagaaa     840
cttgagggtc atactgagac cgtcatgaac gtagcatgcc acccgacaga gaacttgatc     900
gcatcaggct cgctcgacaa gacagtaagg atttggacac agaagaaaga ataa           954
```

<210> SEQ ID NO 22
<211> LENGTH: 317
<212> TYPE: PRT
<213> ORGANISM: Arabidopsis thaliana

<400> SEQUENCE: 22

Met Ala Glu Glu Ile Pro Ala Thr Ala Ser Phe Thr Pro Tyr Val His
1               5                   10                  15

Ser Gln Thr Leu Thr Ser His Asn Arg Ala Val Ser Val Lys Phe
            20                  25                  30

Ser Ser Asp Gly Arg Leu Leu Ala Ser Ala Ser Ala Asp Lys Thr Ile
        35                  40                  45

Arg Thr Tyr Thr Ile Asn Thr Ile Asn Asp Pro Ile Ala Glu Pro Val
    50                  55                  60

Gln Glu Phe Thr Gly His Glu Asn Gly Ile Ser Asp Val Ala Phe Ser
65              70                  75                  80

Ser Asp Ala Arg Phe Ile Val Ser Ala Ser Asp Lys Thr Leu Lys
                85                  90                  95

Leu Trp Asp Val Glu Thr Gly Ser Leu Ile Lys Thr Leu Ile Gly His
            100                 105                 110

Thr Asn Tyr Ala Phe Cys Val Asn Phe Asn Pro Gln Ser Asn Met Ile
        115                 120                 125

Val Ser Gly Ser Phe Asp Glu Thr Val Arg Ile Trp Asp Val Thr Thr
    130                 135                 140

Gly Lys Cys Leu Lys Val Leu Pro Ala His Ser Asp Pro Val Thr Ala
145             150                 155                 160

Val Asp Phe Asn Arg Asp Gly Ser Leu Ile Val Ser Ser Ser Tyr Asp
                165                 170                 175

Gly Leu Cys Arg Ile Trp Asp Ser Gly Thr Gly His Cys Val Lys Thr
            180                 185                 190

Leu Ile Asp Asp Glu Asn Pro Pro Val Ser Phe Val Arg Phe Ser Pro
        195                 200                 205

Asn Gly Lys Phe Ile Leu Val Gly Thr Leu Asp Asn Thr Leu Arg Leu
    210                 215                 220

Trp Asn Ile Ser Ser Ala Lys Phe Leu Lys Thr Tyr Thr Gly His Val
225             230                 235                 240

Asn Ala Gln Tyr Cys Ile Ser Ser Ala Phe Ser Val Thr Asn Gly Lys
                245                 250                 255

Arg Ile Val Ser Gly Ser Glu Asp Asn Cys Val His Met Trp Glu Leu
            260                 265                 270

Asn Ser Lys Lys Leu Leu Gln Lys Leu Glu Gly His Thr Glu Thr Val
        275                 280                 285

Met Asn Val Ala Cys His Pro Thr Glu Asn Leu Ile Ala Ser Gly Ser
    290                 295                 300

Leu Asp Lys Thr Val Arg Ile Trp Thr Gln Lys Lys Glu
305             310                 315

<210> SEQ ID NO 23
<211> LENGTH: 768
<212> TYPE: DNA
<213> ORGANISM: Arabidopsis thaliana

<400> SEQUENCE: 23
atgtcgacaa gggaagagaa tgtttacatg gcgaaattag ccgaacaagc tgaacgttac      60
gaagaaatgg ttgaattcat ggagaaagtt gcgaaaactg ttgatgttga ggaactttca     120

-continued

```
gttgaagaga ggaatcttct ctctgttgct tacaagaacg tgattggagc gagaagagct    180
tcgtggagaa tcatttcttc gattgagcag aaagaagaga gcaaagggaa cgaagatcat    240
gttgctatta tcaaggatta cagaggaaag attgaatccg agcttagcaa atctgtgat    300
gggattttga atgttcttga agctcatctt attccttctg cttcaccagc tgaatctaaa    360
gtgttttatc ttaagatgaa gggtgattat cataggtatc ttgctgagtt taaggctggt    420
gctgaaagga aagaagctgc tgaaagcact ttggttgctt acaagtctgc ttccgacatt    480
gccactgctg agttagctcc tactcacccg ataaggcttg gtcttgcact caacttctct    540
gtgttttact atgaaatcct caactcgcct gatcgtgctt gcagcctcgc aaagcaggcg    600
tttgatgatg caatcgctga gttagataca ttgggtgagg aatcatacaa ggacagtaca    660
ctgattatgc agcttcttag agacaatctc actctctgga cttcagatat gactgacgaa    720
gcaggagatg agattaagga ggcatcaaag cccgatggtg ccgagtaa                 768
```

<210> SEQ ID NO 24
<211> LENGTH: 255
<212> TYPE: PRT
<213> ORGANISM: Arabidopsis thaliana

<400> SEQUENCE: 24

```
Met Ser Thr Arg Glu Glu Asn Val Tyr Met Ala Lys Leu Ala Glu Gln
1               5                   10                  15

Ala Glu Arg Tyr Glu Glu Met Val Glu Phe Met Glu Lys Val Ala Lys
            20                  25                  30

Thr Val Asp Val Glu Glu Leu Ser Val Glu Glu Arg Asn Leu Leu Ser
        35                  40                  45

Val Ala Tyr Lys Asn Val Ile Gly Ala Arg Arg Ala Ser Trp Arg Ile
    50                  55                  60

Ile Ser Ser Ile Glu Gln Lys Glu Glu Ser Lys Gly Asn Glu Asp His
65                  70                  75                  80

Val Ala Ile Ile Lys Asp Tyr Arg Gly Lys Ile Glu Ser Glu Leu Ser
                85                  90                  95

Lys Ile Cys Asp Gly Ile Leu Asn Val Leu Glu Ala His Leu Ile Pro
            100                 105                 110

Ser Ala Ser Pro Ala Glu Ser Lys Val Phe Tyr Leu Lys Met Lys Gly
        115                 120                 125

Asp Tyr His Arg Tyr Leu Ala Glu Phe Lys Ala Gly Ala Glu Arg Lys
    130                 135                 140

Glu Ala Ala Glu Ser Thr Leu Val Ala Tyr Lys Ser Ala Ser Asp Ile
145                 150                 155                 160

Ala Thr Ala Glu Leu Ala Pro Thr His Pro Ile Arg Leu Gly Leu Ala
                165                 170                 175

Leu Asn Phe Ser Val Phe Tyr Tyr Glu Ile Leu Asn Ser Pro Asp Arg
            180                 185                 190

Ala Cys Ser Leu Ala Lys Gln Ala Phe Asp Asp Ala Ile Ala Glu Leu
        195                 200                 205

Asp Thr Leu Gly Glu Glu Ser Tyr Lys Asp Ser Thr Leu Ile Met Gln
    210                 215                 220

Leu Leu Arg Asp Asn Leu Thr Leu Trp Thr Ser Asp Met Thr Asp Glu
225                 230                 235                 240

Ala Gly Asp Glu Ile Lys Glu Ala Ser Lys Pro Asp Gly Ala Glu
                245                 250                 255
```

<210> SEQ ID NO 25

```
<211> LENGTH: 774
<212> TYPE: DNA
<213> ORGANISM: Brassica napus

<400> SEQUENCE: 25
atgtcgtcac gtgaggtgaa tgtgtacatg gcgaaactag ccgaacaagc cgagcgttac      60
gaagagatgg ttgagttcat ggagaaagtt gctaaaaccg tcgactctga agaactcact     120
gtcgaggaga ggaaccttct ctccgttgct tacaagaacg tgatcggagc gaggagggct     180
tcgtggagga tcatctcttc cattgagcag aaggaagaga gcaagggaa cgaagaacac     240 gttgctatca tcaaggagta caggggaag attgaaaccg agcttagcaa aatctgcgac     300
gggatcttga atgttcttga agctcatctc atcccctctg cttcgcctgc tgagtctaag     360
gtgttttatc tgaagatgaa gggagattat cacaggtatc ttgctgagtt taaggctggt     420
gatgagagga aagatgctgc tgagagcact ttggttgctt acaagtctgc tcaggacatt     480
gcgactgctg agttagctcc aactcacccg atcaggcttg gtcttgcact caacttctct     540
gtgttttact atgagatcct taactcgcct gaccgtgcct gcaccctcgc taagcaggca     600
tttgatgaag ctatcgctga gctggataca ttgggagagg aatcatacaa agacagtacg     660
ctgattatgc agcttctcag agacaacctc actctctgga cttctgacat gactgacgaa     720
gcaggagatg agataaagga ggcatcgaag ccagaaggcg gtgcagcaga gtaa          774
```

<210> SEQ ID NO 26
<211> LENGTH: 257
<212> TYPE: PRT
<213> ORGANISM: Brassica napus

<400> SEQUENCE: 26

```
Met Ser Ser Arg Glu Val Asn Val Tyr Met Ala Lys Leu Ala Glu Gln
1               5                   10                  15

Ala Glu Arg Tyr Glu Glu Met Val Glu Phe Met Glu Lys Val Ala Lys
            20                  25                  30

Thr Val Asp Ser Glu Glu Leu Thr Val Glu Glu Arg Asn Leu Leu Ser
        35                  40                  45

Val Ala Tyr Lys Asn Val Ile Gly Ala Arg Arg Ala Ser Trp Arg Ile
    50                  55                  60

Ile Ser Ser Ile Glu Gln Lys Glu Glu Ser Lys Gly Asn Glu Glu His
65                  70                  75                  80

Val Ala Ile Ile Lys Glu Tyr Arg Gly Lys Ile Glu Thr Glu Leu Ser
                85                  90                  95

Lys Ile Cys Asp Gly Ile Leu Asn Val Leu Glu Ala His Leu Ile Pro
            100                 105                 110

Ser Ala Ser Pro Ala Glu Ser Lys Val Phe Tyr Leu Lys Met Lys Gly
        115                 120                 125

Asp Tyr His Arg Tyr Leu Ala Glu Phe Lys Ala Gly Asp Glu Arg Lys
    130                 135                 140

Asp Ala Ala Glu Ser Thr Leu Val Ala Tyr Lys Ser Ala Gln Asp Ile
145                 150                 155                 160

Ala Thr Ala Glu Leu Ala Pro Thr His Pro Ile Arg Leu Gly Leu Ala
                165                 170                 175

Leu Asn Phe Ser Val Phe Tyr Glu Ile Leu Asn Ser Pro Asp Arg
            180                 185                 190

Ala Cys Thr Leu Ala Lys Gln Ala Phe Asp Glu Ala Ile Ala Glu Leu
        195                 200                 205

Asp Thr Leu Gly Glu Glu Ser Tyr Lys Asp Ser Thr Leu Ile Met Gln
```

```
                210                 215                  220
Leu Leu Arg Asp Asn Leu Thr Leu Trp Thr Ser Asp Met Thr Asp Glu
225                 230                  235                 240

Ala Gly Asp Glu Ile Lys Glu Ala Ser Lys Pro Glu Gly Gly Ala Ala
                245                  250                 255

Glu

<210> SEQ ID NO 27
<211> LENGTH: 1218
<212> TYPE: DNA
<213> ORGANISM: Arabidopsis thaliana

<400> SEQUENCE: 27
atgggtggtt tggctatgga ggaaatgcct ttatcggtgc tattcgagca agctaggaaa      60
attcatcttg ctgcttcaga gtctggtgtt gatcaggatg ttgtgaagaa aggatgtgag     120
atgtttcaga agtgcgaaga tatgatcggg aagctggcgc tgttttcgtc taacgagact     180
aaagaagata ttagcaccaa caatctcaaa tatcttttgg tgccttatta tcttgcggag     240
ttgacagaga aaatcataca ggaggaccgg attcagattg tcaaagcctc gtatgctaag     300
ttgaaggagt tcttttcgtt ctgtgaggca atggagcttg ttccggatga ggagttggag     360
gcttcttcac gaggaggttc tggtgcacct gctgatcgaa gggctctcaa gatagctcgg     420
ttcaaacgtc aaaaggctgc agaggcaaag cttcttgaaa ttaaagagag gaaggagcga     480
cgtggacgtt ccactaaagc atcagctttg tcgactccgg ttgaatctgg agaagatgat     540
attccagatg atgacagcga agaagagaga gaggcctggc tctcctcaat taacttggct     600
atttgtaagg ctattgatct gttggaaatg ctaaagagag aagaggaaat gctctctgca     660
ataaaggaaa gacagttgaa ggatggagag ggtggatttt ctcgggatgc tcttgatgat     720
cgtacaaaga agctgaaaac ctggcacaga gacgctgctg caaggataca gtactctaaa     780
ccggcacaac caatcacttg tgccacattt gcacaagatg tgttagaagg aagagcttcg     840
gtatcacaag gtcacgaaca caagaaccaa cctcttatat tcggtccagc aagcatcgtg     900
ggtggaccgc tctctaccga gagagaaaga atgatagctc aggtcttcca accaagtcac     960
aggatgccaa caatgtgcat agaggatgct gggttaacag atgaacat aatgaatgat    1020 tggcaagagc agacgaaaaa agccattgaa gaagcaacca cctcatggta caatgataaa    1080
cctctaagaa gaaaagaaga gacgaggaa gatgatgatg aagacgaaga agctgtgatg    1140
aaagctagag ctttcgatga ttggaaggat gataatcctc gcggtgcagg taacaagaaa    1200
ctcacacctt gtggctga                                                  1218

<210> SEQ ID NO 28
<211> LENGTH: 405
<212> TYPE: PRT
<213> ORGANISM: Arabidopsis thaliana

<400> SEQUENCE: 28

Met Gly Gly Leu Ala Met Glu Glu Met Pro Leu Ser Val Leu Phe Glu
1               5                  10                  15

Gln Ala Arg Lys Ile His Leu Ala Ala Ser Glu Ser Gly Val Asp Gln
                20                  25                  30

Asp Val Val Lys Lys Gly Cys Glu Met Phe Gln Lys Cys Glu Asp Met
            35                  40                  45

Ile Gly Lys Leu Ala Leu Phe Ser Ser Asn Glu Thr Lys Glu Asp Ile
    50                  55                  60
```

Ser Thr Asn Asn Leu Lys Tyr Leu Leu Val Pro Tyr Leu Ala Glu
 65                  70                  75                  80

Leu Thr Glu Lys Ile Gln Glu Asp Arg Ile Gln Ile Val Lys Ala
             85                  90                  95

Ser Tyr Ala Lys Leu Lys Glu Phe Phe Ser Phe Cys Glu Ala Met Glu
            100                 105                 110

Leu Val Pro Asp Glu Glu Leu Glu Ala Ser Ser Arg Gly Gly Ser Gly
            115                 120                 125

Ala Pro Ala Asp Arg Arg Ala Leu Lys Ile Ala Arg Phe Lys Arg Gln
            130                 135                 140

Lys Ala Ala Glu Ala Lys Leu Leu Glu Ile Lys Glu Arg Lys Glu Arg
145                 150                 155                 160

Arg Gly Arg Ser Thr Lys Ala Ser Ala Leu Ser Thr Pro Val Glu Ser
                165                 170                 175

Gly Glu Asp Asp Ile Pro Asp Asp Ser Glu Glu Glu Arg Glu Ala
                180                 185                 190

Trp Leu Ser Ser Ile Asn Leu Ala Ile Cys Lys Ala Ile Asp Leu Leu
                195                 200                 205

Glu Met Leu Lys Arg Glu Glu Met Leu Ser Ala Ile Lys Glu Arg
    210                 215                 220

Gln Leu Lys Asp Gly Glu Gly Gly Phe Ser Arg Asp Ala Leu Asp Asp
225                 230                 235                 240

Arg Thr Lys Lys Ala Glu Thr Trp His Arg Asp Ala Ala Arg Ile
                245                 250                 255

Gln Tyr Ser Lys Pro Ala Gln Pro Ile Thr Cys Ala Thr Phe Ala Gln
                260                 265                 270

Asp Val Leu Glu Gly Arg Ala Ser Val Ser Gln Gly His Glu His Lys
                275                 280                 285

Asn Gln Pro Leu Ile Phe Gly Pro Ala Ser Ile Val Gly Gly Pro Leu
                290                 295                 300

Ser Thr Glu Arg Glu Arg Met Ile Ala Gln Val Phe Gln Pro Ser His
305                 310                 315                 320

Arg Met Pro Thr Met Cys Ile Glu Asp Ala Gly Leu Thr Glu Met Asn
                325                 330                 335

Ile Met Asn Asp Trp Gln Glu Gln Thr Lys Lys Ala Ile Glu Glu Ala
                340                 345                 350

Thr Thr Ser Trp Tyr Asn Asp Lys Pro Leu Arg Arg Lys Glu Glu Asp
                355                 360                 365

Glu Glu Asp Asp Asp Glu Asp Glu Glu Ala Val Met Lys Ala Arg Ala
                370                 375                 380

Phe Asp Asp Trp Lys Asp Asp Asn Pro Arg Gly Ala Gly Asn Lys Lys
385                 390                 395                 400

Leu Thr Pro Cys Gly
            405

<210> SEQ ID NO 29
<211> LENGTH: 1218
<212> TYPE: DNA
<213> ORGANISM: Brassica napus

<400> SEQUENCE: 29
atgggtggtg tagctatgga ggagatgcca ttatcggcgt tgttcgagga agcaaggaag    60
attcatctcg cggcttcaga atcccgcgcc gatcaggatg ttgtgaggaa aggatgtgag   120
atgttacaga aatgcgaaga catggttggg aagctggggc tcttctcttc taacgagact   180

```
aaagaagata tcagcaccaa caatctcaag tatcttttgg tacctttcta tcttgcggag    240
ttgacagaga aaatcaaaca ggaggatcgg attccgattg tcaaggcttc gtatgctaag    300
ttgaaggagt tcttttcgtt ctgtgaggca atggaacttg ttccggaaga ggagttggag    360
gcttcttcac gaggaggttc tgctccacct gctgatcgga gagctctcaa gatagctcgg    420
ttcaaacgtc agaaggctgc agaggcgaag ctccttgaga ttaaagagag gaaggagcga    480
cggggacgtt caaaagggc tgctgccttg tcaactccgg ttgaatctgg agaagaagac    540
atcccagatg atgacagcga agaagaaaga gatgcgtggc tcgccacaat taacttggct    600
atttgcaagg ctattgatct gttggaaatg ctaaagagag aagaggaaat gctctctgca    660
atcaaggaaa aacagttgaa ggatggagag gatgtgtttt ctcgggatgc acttgatgat    720
cgcacaaaga aggctgaaac ttggcacaga gatgctgctg cgagggtaca gtactctaga    780
ccggcacaac caatcacttg tgctacattt gcacaagatg tgttggaagg agagcttca    840 gtatcacagg tcacgagca aagcaccaa cctcttatat tcggtccagc aagcattgtg    900
aatggatctc tttctacgga gagagagagg atgatagctc aagttttcca accaagtcac    960
aggatgccga cgatgagcat agaggatgct gggttaacag atgaatat aatgaatgat   1020 tggcaagaac agaccaaaaa agccattgaa gaagcaacca cctcatggca caatgatagg   1080
cctctgagaa gaaaggaaga ggatgaagaa gatgaggacg aagatgaaga agctgtgatg   1140
aaagctagag ctttcgatga ttggaaggac gataatcctc gtggtgcagg taacaagaaa   1200
ctcactcctt gtggctga                                                1218
```

<210> SEQ ID NO 30
<211> LENGTH: 405
<212> TYPE: PRT
<213> ORGANISM: Brassica napus

<400> SEQUENCE: 30

```
Met Gly Gly Val Ala Met Glu Glu Met Pro Leu Ser Ala Leu Phe Glu
1               5                  10                  15

Glu Ala Arg Lys Ile His Leu Ala Ala Ser Glu Ser Arg Ala Asp Gln
            20                  25                  30

Asp Val Val Arg Lys Gly Cys Glu Met Leu Gln Lys Cys Glu Asp Met
        35                  40                  45

Val Gly Lys Leu Gly Leu Phe Ser Ser Asn Glu Thr Lys Glu Asp Ile
    50                  55                  60

Ser Thr Asn Asn Leu Lys Tyr Leu Leu Val Pro Phe Tyr Leu Ala Glu
65                  70                  75                  80

Leu Thr Glu Lys Ile Lys Gln Glu Asp Arg Ile Pro Ile Val Lys Ala
                85                  90                  95

Ser Tyr Ala Lys Leu Lys Glu Phe Phe Ser Phe Cys Glu Ala Met Glu
            100                 105                 110

Leu Val Pro Glu Glu Leu Glu Ala Ser Ser Arg Gly Gly Ser Ala
        115                 120                 125

Pro Pro Ala Asp Arg Arg Ala Leu Lys Ile Ala Arg Phe Lys Arg Gln
    130                 135                 140

Lys Ala Ala Glu Ala Lys Leu Leu Glu Ile Lys Glu Arg Lys Glu Arg
145                 150                 155                 160

Arg Gly Arg Ser Lys Arg Ala Ala Ala Leu Ser Thr Pro Val Glu Ser
                165                 170                 175

Gly Glu Glu Asp Ile Pro Asp Asp Asp Ser Glu Glu Arg Asp Ala
            180                 185                 190
```

```
Trp Leu Ala Thr Ile Asn Leu Ala Ile Cys Lys Ala Ile Asp Leu Leu
        195                 200                 205
Glu Met Leu Lys Arg Glu Glu Met Leu Ser Ala Ile Lys Glu Lys
210                 215                 220
Gln Leu Lys Asp Gly Glu Asp Val Phe Ser Arg Asp Ala Leu Asp Asp
225                 230                 235                 240
Arg Thr Lys Lys Ala Glu Thr Trp His Arg Asp Ala Ala Arg Val
            245                 250                 255
Gln Tyr Ser Arg Pro Ala Gln Pro Ile Thr Cys Ala Thr Phe Ala Gln
            260                 265                 270
Asp Val Leu Glu Gly Arg Ala Ser Val Ser Gln Gly His Glu His Lys
        275                 280                 285
His Gln Pro Leu Ile Phe Gly Pro Ala Ser Ile Val Asn Gly Ser Leu
    290                 295                 300
Ser Thr Glu Arg Glu Arg Met Ile Ala Gln Val Phe Gln Pro Ser His
305                 310                 315                 320
Arg Met Pro Thr Met Ser Ile Glu Asp Ala Gly Leu Thr Glu Met Asn
                325                 330                 335
Ile Met Asn Asp Trp Gln Glu Gln Thr Lys Lys Ala Ile Glu Glu Ala
            340                 345                 350
Thr Thr Ser Trp His Asn Asp Arg Pro Leu Arg Arg Lys Glu Glu Asp
        355                 360                 365
Glu Glu Asp Glu Asp Glu Asp Glu Glu Ala Val Met Lys Ala Arg Ala
    370                 375                 380
Phe Asp Asp Trp Lys Asp Asp Asn Pro Arg Gly Ala Gly Asn Lys Lys
385                 390                 395                 400
Leu Thr Pro Cys Gly
            405

<210> SEQ ID NO 31
<211> LENGTH: 4035
<212> TYPE: DNA
<213> ORGANISM: Arabidopsis thaliana

<400> SEQUENCE: 31
atggcattag agacttaat ggtgtctcgg ttctcgcaat cttctgtttc tttggtctcc      60
aatcaccgtt acgacgaaga ctgtgtctct agtcacgatg acggtgattc ccggaggaag    120
gattctgagg ctaagagcag tagtagctac gggaatggta caacggaggg agccgccacc    180
gccaccagca tggcttactt gcctcagact attgtgctct gcgagcttag acacgacgca    240
tccgaggctt ctgctccctt ggggacttct gagatcgtat tggtccccaa atggcggctt    300
aaagaacgaa tgaaaacagg atgtgtagct ttagttctgt gtttaaacat tactgttgat    360
ccgccggatg ttataaagat atctccttgt gctagaatcg aggcatggat agatccattt    420
tctatggcac cgcctaaagc tctcgagaca attggaaaaa atttgagcac tcagtatgag    480
agatggcaac ccagggcccg ctataaggtt cagcttgatc cgacagtaga tgaggtgagg    540
aagctgtgct tgacttgtcg gaaatatgca aagaccgaga gagttctatt ccattataat    600
gggcatggtg tgccaaaacc tacagctaat ggtgaaattt gggtatttaa caagagttat    660
acacagtaca ttcccttgcc aatcagtgaa cttgattcct ggttgaagac accctccatc    720
tatgttttcg actgctctgc tgctaggatg attctgaatg cctttgctga gcttcatgat    780
tggggttctt ctggttcctc tggatcctca agggactgca ttctacttgc tgcttgtgat    840
gtacatgaga cacttcctca gagcgttgag tttccagctg atgtttttac gtcttgcctg    900
```

-continued

```
acaacgccca ttaaaatggc gttgaaatgg ttctgcaggc gttcgcttct gaaagaaatt    960
atcgatgaat cacttatcga caggattcca ggccggcaaa acgatcgtaa gacattgtta   1020
ggggagttga actggatttt cacagcagtg acggatacaa ttgcttggaa tgtgcttcct   1080
catgaacttt tccagagatt attcagacag gacttgttgg tcgctagcct tttccggaat   1140
ttcttacttg ctgagagaat aatgcggtcc gcaaactgta atccaatatc tcaccctatg   1200
ctgcctccta cgcatcaaca tcatatgtgg gatgcatggg acatggctgc tgaaatctgt   1260
ctttctcagc ttccccaact tgttctggac ccaagcacag agttccagcc aagtccgttt   1320
tttactgagc aactgacagc ttttgaggtg tggcttgatc atggatctga gcataagaag   1380
ccaccggagc agttacctat tgttcttcag gtgttactta gccagtgcca tcggtttcgt   1440
gctcttgtac ttcttggaag atttcttgat atgggttcat gggctgtgga tctggccttg   1500
tctgttggaa tattcccata tgtgctgaag cttctgcaaa caacaacgaa tgagctaaga   1560
cagatcctgg ttttcatatg gacaaaaatt cttgcacttg acaagtcatg tcaaattgat   1620
cttgtgaagg atggggggca tacatacttc atacgatttc tagatagctc gggtgcattt   1680
ccagaacaac gagctatggc tgcttttgtt ctggctgtca ttgtggatgg acatcgacga   1740
ggccaggaag catgtcttga agctaattta attggtgttt gtctcgggca ccttgaagca   1800
tccagaccaa gtgatccaca accagaacca ttgtttctac aatggctttg tctttgtctt   1860
ggaaagttat gggaagattt tatggaggcc caaataatgg gcagggaggc aaatgctttt   1920
gaaaagttgg cacctctgct ttccgagccc caacctgagg taagggctgc tgcagttttt   1980
gccctgggta ccttgcttga tattgggttt gactctaata aaagtgtggt ggaggatgaa   2040
tttgatgatg atgaaaagat tagagccgaa gacgctatca ttaaaagtct cttagatgta   2100
gtttcagatg ggagtccact tgtccgagca gaggttgccg tagctcttgc acgttttgcc   2160
tttggccaca acagcacct taagttagcc gcagcttcat attggaagcc tcagtcaagt   2220
tctttgctta cttctctacc ttcaatagct aaattccatg atcctgggag tgcaacaatt   2280
gtttctttac acatgagtcc tctgactaga gctagcacgg atagccaacc agtggctcgt   2340
gagtctagga tctcaagcag ccctcttggc tcctctgggc tgatgcaagg atctccatta   2400
tctgatgatt cttcgttaca ttctgattct ggaatgatgc atgacagtgt cagcaatgga   2460
gcggtccatc agccaagact gttggataat gctgtttatt cgcagtgcgt ccgagctatg   2520
tttgcattag ctaaagatcc atctccacgt attgcaagtc tcggacggcg tgtgctttct   2580
attattggaa tcgaacaggt tgttgcgaaa ccctcgaagc ccactggccg accaggggaa   2640
gctgcaacga catctcacac tccacttgct ggcctagctc gttcatcctc atggtttgat   2700
atgcatgcag gtaatctgcc tttaagtttt aggactcccc cggtcagccc ccctagaaca   2760
aactacctga gtggattgag gagagtttgt tcattagagt tcaggcctca tctattgggt   2820
tcacccgact caggattggc tgatccgctt ttaggcgcca gtggatctga acggagtttg   2880
cttccactat caactatcta cggctggagt tgtgggcact tttctaagcc acttcttggt   2940
ggtgcggatg ctagtcaaga gattgcagcc aaaagagaag agaaagaaaa attcgcactt   3000
gagcatattg caaaatgcca gcactcttct attagcaagc tcaacaataa tcctattgcc   3060
aactgggata caaggtttga aacgggaaca aagacagccc tccttcaccc attctctcct   3120
attgtagttg ctgcagacga gaatgaacgg atcagagtgt ggaactatga ggaagcaact   3180
cttctcaatg gctttgacaa tcatgatttt cctgacaaag gaatttcaaa gctctgcctc   3240
atcaatgaac ttgacgactc tctgctactt gttgcatcat gcgatgggtc ggtccggata   3300
```

-continued

```
tggaaaaact atgcaactaa gggtaaacaa aagcttgtta ctgggttttc ttcaatccag    3360
ggtcacaagc ccggtgcccg tgacttgaac gctgtcgtgg actggcaaca acagtccggt    3420
tacctgtatg cttctgggga gacgtcaaca gtcacacttt gggacctgga gaagaacag     3480
cttgtcagat ctgttccctc tgaatcagaa tgtggagtta cagcactttc tgcttctcaa    3540
gtgcacggag ccaactcgc tgctggtttt gctgatggat ctttgagact ctatgatgtt    3600
cggtcacctg aaccgcttgt ctgcgcgact cggcctcatc agaaagttga aagggtggtt    3660
ggcctcagtt ttcaacctgg acttgacccc gcaaaggtgg tgagtgcatc acaggcgggt    3720
gacatacagt ttcttgacct agaacaaca agggacacat acctgacgat tgatgcacac    3780
agggggttcac tcacggcctt agctgttcac agacacgctc aataatcgc gagtggatct    3840
gcaaaacagc tcattaaagt attcagtctt caagggaac aactagggat aatccgctac    3900
tacccatcct tcatggctca aaagattgga tcagtgagtt gcctcacatt tcatccgtac    3960
caggttctgc tagcagctgg agctgctgac tcatttgtct ccatatacac ccacgacaac    4020
tcgcaagcaa gatga                                                     4035
```

<210> SEQ ID NO 32
<211> LENGTH: 1344
<212> TYPE: PRT
<213> ORGANISM: Arabidopsis thaliana

<400> SEQUENCE: 32

```
Met Ala Leu Gly Asp Leu Met Val Ser Arg Phe Ser Gln Ser Ser Val
1               5                   10                  15

Ser Leu Val Ser Asn His Arg Tyr Asp Glu Asp Cys Val Ser Ser His
            20                  25                  30

Asp Asp Gly Asp Ser Arg Arg Lys Asp Ser Glu Ala Lys Ser Ser Ser
        35                  40                  45

Ser Tyr Gly Asn Gly Thr Thr Glu Gly Ala Ala Thr Ala Thr Ser Met
    50                  55                  60

Ala Tyr Leu Pro Gln Thr Ile Val Leu Cys Glu Leu Arg His Asp Ala
65                  70                  75                  80

Ser Glu Ala Ser Ala Pro Leu Gly Thr Ser Glu Ile Val Leu Val Pro
                85                  90                  95

Lys Trp Arg Leu Lys Glu Arg Met Lys Thr Gly Cys Val Ala Leu Val
            100                 105                 110

Leu Cys Leu Asn Ile Thr Val Asp Pro Pro Asp Val Ile Lys Ile Ser
        115                 120                 125

Pro Cys Ala Arg Ile Glu Ala Trp Ile Asp Pro Phe Ser Met Ala Pro
    130                 135                 140

Pro Lys Ala Leu Glu Thr Ile Gly Lys Asn Leu Ser Thr Gln Tyr Glu
145                 150                 155                 160

Arg Trp Gln Pro Arg Ala Arg Tyr Lys Val Gln Leu Asp Pro Thr Val
                165                 170                 175

Asp Glu Val Arg Lys Leu Cys Leu Thr Cys Arg Lys Tyr Ala Lys Thr
            180                 185                 190

Glu Arg Val Leu Phe His Tyr Asn Gly His Gly Val Pro Lys Pro Thr
        195                 200                 205

Ala Asn Gly Glu Ile Trp Val Phe Asn Lys Ser Tyr Thr Gln Tyr Ile
    210                 215                 220

Pro Leu Pro Ile Ser Glu Leu Asp Ser Trp Leu Lys Thr Pro Ser Ile
225                 230                 235                 240

Tyr Val Phe Asp Cys Ser Ala Ala Arg Met Ile Leu Asn Ala Phe Ala
```

```
                        245                 250                 255
Glu Leu His Asp Trp Gly Ser Ser Gly Ser Ser Gly Ser Arg Asp
            260                 265                 270

Cys Ile Leu Leu Ala Ala Cys Asp Val His Glu Thr Leu Pro Gln Ser
            275                 280                 285

Val Glu Phe Pro Ala Asp Val Phe Thr Ser Cys Leu Thr Thr Pro Ile
        290                 295                 300

Lys Met Ala Leu Lys Trp Phe Cys Arg Arg Ser Leu Leu Lys Glu Ile
305                 310                 315                 320

Ile Asp Glu Ser Leu Ile Asp Arg Ile Pro Gly Arg Gln Asn Asp Arg
                325                 330                 335

Lys Thr Leu Leu Gly Glu Leu Asn Trp Ile Phe Thr Ala Val Thr Asp
            340                 345                 350

Thr Ile Ala Trp Asn Val Leu Pro His Glu Leu Phe Gln Arg Leu Phe
            355                 360                 365

Arg Gln Asp Leu Leu Val Ala Ser Leu Phe Arg Asn Phe Leu Leu Ala
        370                 375                 380

Glu Arg Ile Met Arg Ser Ala Asn Cys Asn Pro Ile Ser His Pro Met
385                 390                 395                 400

Leu Pro Pro Thr His Gln His Met Trp Asp Ala Trp Asp Met Ala
                405                 410                 415

Ala Glu Ile Cys Leu Ser Gln Leu Pro Gln Leu Val Leu Asp Pro Ser
            420                 425                 430

Thr Glu Phe Gln Pro Ser Pro Phe Phe Thr Glu Gln Leu Thr Ala Phe
            435                 440                 445

Glu Val Trp Leu Asp His Gly Ser Glu His Lys Lys Pro Pro Glu Gln
        450                 455                 460

Leu Pro Ile Val Leu Gln Val Leu Leu Ser Gln Cys His Arg Phe Arg
465                 470                 475                 480

Ala Leu Val Leu Leu Gly Arg Phe Leu Asp Met Gly Ser Trp Ala Val
                485                 490                 495

Asp Leu Ala Leu Ser Val Gly Ile Phe Pro Tyr Val Leu Lys Leu Leu
            500                 505                 510

Gln Thr Thr Thr Asn Glu Leu Arg Gln Ile Leu Val Phe Ile Trp Thr
            515                 520                 525

Lys Ile Leu Ala Leu Asp Lys Ser Cys Gln Ile Asp Leu Val Lys Asp
        530                 535                 540

Gly Gly His Thr Tyr Phe Ile Arg Phe Leu Asp Ser Ser Gly Ala Phe
545                 550                 555                 560

Pro Glu Gln Arg Ala Met Ala Ala Phe Val Leu Ala Val Ile Val Asp
                565                 570                 575

Gly His Arg Arg Gly Gln Glu Ala Cys Leu Glu Ala Asn Leu Ile Gly
            580                 585                 590

Val Cys Leu Gly His Leu Glu Ala Ser Arg Pro Ser Asp Pro Gln Pro
        595                 600                 605

Glu Pro Leu Phe Leu Gln Trp Leu Cys Leu Cys Leu Gly Lys Leu Trp
        610                 615                 620

Glu Asp Phe Met Glu Ala Gln Ile Met Gly Arg Glu Ala Asn Ala Phe
625                 630                 635                 640

Glu Lys Leu Ala Pro Leu Leu Ser Glu Pro Gln Pro Glu Val Arg Ala
                645                 650                 655

Ala Ala Val Phe Ala Leu Gly Thr Leu Leu Asp Ile Gly Phe Asp Ser
            660                 665                 670
```

```
Asn Lys Ser Val Val Glu Asp Glu Phe Asp Asp Glu Lys Ile Arg
        675                 680                 685
Ala Glu Asp Ala Ile Ile Lys Ser Leu Leu Asp Val Val Ser Asp Gly
    690                 695                 700
Ser Pro Leu Val Arg Ala Glu Val Ala Val Ala Leu Ala Arg Phe Ala
705                 710                 715                 720
Phe Gly His Lys Gln His Leu Lys Leu Ala Ala Ala Ser Tyr Trp Lys
                725                 730                 735
Pro Gln Ser Ser Ser Leu Leu Thr Ser Leu Pro Ser Ile Ala Lys Phe
            740                 745                 750
His Asp Pro Gly Ser Ala Thr Ile Val Ser Leu His Met Ser Pro Leu
        755                 760                 765
Thr Arg Ala Ser Thr Asp Ser Gln Pro Val Ala Arg Glu Ser Arg Ile
    770                 775                 780
Ser Ser Ser Pro Leu Gly Ser Ser Gly Leu Met Gln Gly Ser Pro Leu
785                 790                 795                 800
Ser Asp Asp Ser Ser Leu His Ser Asp Ser Gly Met Met His Asp Ser
                805                 810                 815
Val Ser Asn Gly Ala Val His Gln Pro Arg Leu Leu Asp Asn Ala Val
            820                 825                 830
Tyr Ser Gln Cys Val Arg Ala Met Phe Ala Leu Ala Lys Asp Pro Ser
        835                 840                 845
Pro Arg Ile Ala Ser Leu Gly Arg Arg Val Leu Ser Ile Gly Ile
    850                 855                 860
Glu Gln Val Val Ala Lys Pro Ser Lys Pro Thr Gly Arg Pro Gly Glu
865                 870                 875                 880
Ala Ala Thr Thr Ser His Thr Pro Leu Ala Gly Leu Ala Arg Ser Ser
                885                 890                 895
Ser Trp Phe Asp Met His Ala Gly Asn Leu Pro Leu Ser Phe Arg Thr
        900                 905                 910
Pro Pro Val Ser Pro Pro Arg Thr Asn Tyr Leu Ser Gly Leu Arg Arg
    915                 920                 925
Val Cys Ser Leu Glu Phe Arg Pro His Leu Leu Gly Ser Pro Asp Ser
930                 935                 940
Gly Leu Ala Asp Pro Leu Leu Gly Ala Ser Gly Ser Glu Arg Ser Leu
945                 950                 955                 960
Leu Pro Leu Ser Thr Ile Tyr Gly Trp Ser Cys Gly His Phe Ser Lys
                965                 970                 975
Pro Leu Leu Gly Gly Ala Asp Ala Ser Gln Ile Ala Ala Lys Arg
            980                 985                 990
Glu Glu Lys Glu Lys Phe Ala Leu Glu His Ile Ala Lys Cys Gln His
        995                 1000                1005
Ser Ser Ile Ser Lys Leu Asn Asn Asn Pro Ile Ala Asn Trp Asp
    1010                1015                1020
Thr Arg Phe Glu Thr Gly Thr Lys Thr Ala Leu Leu His Pro Phe
    1025                1030                1035
Ser Pro Ile Val Val Ala Ala Asp Glu Asn Glu Arg Ile Arg Val
    1040                1045                1050
Trp Asn Tyr Glu Glu Ala Thr Leu Leu Asn Gly Phe Asp Asn His
    1055                1060                1065
Asp Phe Pro Asp Lys Gly Ile Ser Lys Leu Cys Leu Ile Asn Glu
    1070                1075                1080
Leu Asp Asp Ser Leu Leu Leu Val Ala Ser Cys Asp Gly Ser Val
    1085                1090                1095
```

| Arg | Ile | Trp | Lys | Asn | Tyr | Ala | Thr | Lys | Gly | Lys | Gln | Lys | Leu | Val |
| | 1100 | | | | 1105 | | | | | 1110 | | | | |

Thr Gly Phe Ser Ser Ile Gln Gly His Lys Pro Gly Ala Arg Asp
    1115                    1120                    1125

Leu Asn Ala Val Val Asp Trp Gln Gln Gln Ser Gly Tyr Leu Tyr
    1130                    1135                    1140

Ala Ser Gly Glu Thr Ser Thr Val Thr Leu Trp Asp Leu Glu Lys
    1145                    1150                    1155

Glu Gln Leu Val Arg Ser Val Pro Ser Glu Ser Glu Cys Gly Val
    1160                    1165                    1170

Thr Ala Leu Ser Ala Ser Gln Val His Gly Gly Gln Leu Ala Ala
    1175                    1180                    1185

Gly Phe Ala Asp Gly Ser Leu Arg Leu Tyr Asp Val Arg Ser Pro
    1190                    1195                    1200

Glu Pro Leu Val Cys Ala Thr Arg Pro His Gln Lys Val Glu Arg
    1205                    1210                    1215

Val Val Gly Leu Ser Phe Gln Pro Gly Leu Asp Pro Ala Lys Val
    1220                    1225                    1230

Val Ser Ala Ser Gln Ala Gly Asp Ile Gln Phe Leu Asp Leu Arg
    1235                    1240                    1245

Thr Thr Arg Asp Thr Tyr Leu Thr Ile Asp Ala His Arg Gly Ser
    1250                    1255                    1260

Leu Thr Ala Leu Ala Val His Arg His Ala Pro Ile Ile Ala Ser
    1265                    1270                    1275

Gly Ser Ala Lys Gln Leu Ile Lys Val Phe Ser Leu Gln Gly Glu
    1280                    1285                    1290

Gln Leu Gly Ile Ile Arg Tyr Tyr Pro Ser Phe Met Ala Gln Lys
    1295                    1300                    1305

Ile Gly Ser Val Ser Cys Leu Thr Phe His Pro Tyr Gln Val Leu
    1310                    1315                    1320

Leu Ala Ala Gly Ala Ala Asp Ser Phe Val Ser Ile Tyr Thr His
    1325                    1330                    1335

Asp Asn Ser Gln Ala Arg
    1340

```
<210> SEQ ID NO 33
<211> LENGTH: 2262
<212> TYPE: DNA
<213> ORGANISM: Arabidopsis thaliana

<400> SEQUENCE: 33
atgacgaaga ggagcaaagg agctaacgaa gataagctga tagaaaccaa aagcaaaaac      60
gtttctggaa aatctcagaa acagaagaaa ccagtagaag cagaaagctt aaaagaggaa     120
gaccttctac aagcatccgg aactgattct gattacgacg gagatagttt gcctggttct     180
ttgaattccg acgatttcga ctccgatttt tccgattcag aggatgatgg aacacatgaa     240
ggaacagaag atggagatgt agaattttcc gatgacgacg acgtgcttga gcatgatggg     300
tcaattgata acgaggatga tgatggaagt gaacatgtag gtagtgacaa taatgaggaa     360
catgggagtg atgaagattc tgagcgaggt gaagcggttg aagagagcga ttcctcagaa     420
gatgaggttc catctagaaa tacagttggg aatgttccct aaagtggta tgaagatgag      480 aaacatattg gttatgacct cactgggaag aagattacta agaaagaaaa acaagataaa     540
ctcgactctt ttcttgcaac tatagatgac tctaagactt ggcgcaaaat ttatgatgaa     600
```

-continued

```
tataatgacg aggacgttga gctgactaaa gaggagagca agatcgttca gagaatactc    660
aaaggggaag ctccacatgc ggactttgat ccatatgcac cttatgttga gtggttcaaa    720
catgatgatg caatacatcc actctcaagt gcaccagagc ccaagcgaag attcatccct    780
tcaaatggg aggccaaaaa ggttgttaag attgttagag caatacgtaa ggggtggatc     840
aagtttgata agcctgaaga gagcccaat gtatacccttt tatggggtga tgattcgaca    900
tctgatcaaa agagcaagca tttaacttat attcctccac ccaagcttaa attgccagga    960
cacgatgaat catacaatcc ttctttggaa tatattccaa cagaggagga gaaagcctca    1020
tatgagttga tgtttgagga agatcgtcca aaattcattc ctacaaggtt tacatctttg    1080
agaagcatcc ctgcgtatga gaatgcactg aaggagtctt ttgagcgttg tttggatcta    1140
tacctatgtc caagagttcg aaagaagaga ataaacatcg accctgaatc tttgaagcct    1200
aagctaccta gtaggaagga tcttagacct tatcctaact cctgttatct tgaatataaa    1260
ggccatacag gggctgttac ttcaatatcc actgatagtt ctggcgagtg atagccctca    1320
ggttcaactg atggatctgt ccgtatgtgg gaagtggaga ctggtagatg ccttaaggtc    1380
tggcagtttg acgaagctat catgtgtgtg gcttggaatc ctctttccag gcttccagtt    1440
ttagccgttg ccatgggacg agatttgttt tttctgaaca ctgaacttgg gactgatgag    1500
gaacaggaaa ttactaaaga gaggcttcac tcaggaaaca tcccagaacc agacgcatct    1560
gttgcagcaa ttgtaacctg gctacctgat gagttatatg gagggattaa gataagacat    1620
tttaagagca tatcgtctat tgactggcat cgtaaaggag actatctctc aacagtgatg    1680
gcatccgggg aaaacacgggg agtggtattg caccaactgt caaaacagaa aacacaaagg    1740
ctcccatttta agattcgtgg acttccagtc tgtacacttt ttcatcccag cctttcttac    1800
ttcttcgttg cgacaagaaa ggacgtgcgt gtttacaatc ttttgaagcc aggcgaggcc    1860
accaaaaagc ttgagacagg attgagagaa atctcatcaa tggcgattca tcctggtggt    1920
gataatctga tagtaggaag caaagaaggg aagatgtgtt ggtttgacat ggatctatct    1980
tcgaaaccat acaagactct caagaatcat cctaaagaca ttacaaatgt ggcagttcat    2040
cgatcatatc cgttatttgc ttcgtgctcg gaggattcaa cagcttatgt tttccatgga    2100
atggtgtata atgatctgaa ccagaatcct ctgattgtgc cattggagat tctaagaggt    2160
cattcttcaa aaggaggagt cttggactgc aagtttcatc cgagacaacc atggctattc    2220
actgcaggcg ctgactctat tatcaaactc tattgccact ag                       2262
```

<210> SEQ ID NO 34
<211> LENGTH: 753
<212> TYPE: PRT
<213> ORGANISM: Arabidopsis thaliana

<400> SEQUENCE: 34

Met Thr Lys Arg Ser Lys Gly Ala Asn Glu Asp Lys Leu Ile Glu Thr
1               5                   10                  15

Lys Ser Lys Asn Val Ser Gly Lys Ser Gln Lys Gln Lys Lys Pro Val
            20                  25                  30

Glu Ala Glu Ser Leu Lys Glu Glu Asp Leu Leu Gln Ala Ser Gly Thr
        35                  40                  45

Asp Ser Asp Tyr Asp Gly Asp Ser Leu Pro Gly Ser Leu Asn Ser Asp
    50                  55                  60

Asp Phe Asp Ser Asp Phe Ser Asp Ser Glu Asp Gly Thr His Glu
65                  70                  75                  80

Gly Thr Glu Asp Gly Asp Val Glu Phe Ser Asp Asp Asp Val Leu

-continued

```
                85                  90                  95
Glu His Asp Gly Ser Ile Asp Asn Glu Asp Asp Gly Ser Glu His
            100                 105                 110

Val Gly Ser Asp Asn Asn Glu Glu His Gly Ser Asp Glu Asp Ser Glu
            115                 120                 125

Arg Gly Glu Ala Val Glu Ser Asp Ser Ser Glu Asp Glu Val Pro
            130                 135                 140

Ser Arg Asn Thr Val Gly Asn Val Pro Leu Lys Trp Tyr Glu Asp Glu
145                 150                 155                 160

Lys His Ile Gly Tyr Asp Leu Thr Gly Lys Lys Ile Thr Lys Lys Glu
                165                 170                 175

Lys Gln Asp Lys Leu Asp Ser Phe Leu Ala Thr Ile Asp Asp Ser Lys
                180                 185                 190

Thr Trp Arg Lys Ile Tyr Asp Glu Tyr Asn Asp Glu Asp Val Glu Leu
                195                 200                 205

Thr Lys Glu Glu Ser Lys Ile Val Gln Arg Ile Leu Lys Gly Glu Ala
            210                 215                 220

Pro His Ala Asp Phe Asp Pro Tyr Ala Pro Tyr Val Glu Trp Phe Lys
225                 230                 235                 240

His Asp Asp Ala Ile His Pro Leu Ser Ser Ala Pro Glu Pro Lys Arg
                245                 250                 255

Arg Phe Ile Pro Ser Lys Trp Glu Ala Lys Lys Val Val Lys Ile Val
                260                 265                 270

Arg Ala Ile Arg Lys Gly Trp Ile Lys Phe Asp Lys Pro Glu Glu Glu
                275                 280                 285

Pro Asn Val Tyr Leu Leu Trp Gly Asp Asp Ser Thr Ser Asp Gln Lys
            290                 295                 300

Ser Lys His Leu Thr Tyr Ile Pro Pro Lys Leu Lys Leu Pro Gly
305                 310                 315                 320

His Asp Glu Ser Tyr Asn Pro Ser Leu Glu Tyr Ile Pro Thr Glu Glu
                325                 330                 335

Glu Lys Ala Ser Tyr Glu Leu Met Phe Glu Glu Asp Arg Pro Lys Phe
            340                 345                 350

Ile Pro Thr Arg Phe Thr Ser Leu Arg Ser Ile Pro Ala Tyr Glu Asn
                355                 360                 365

Ala Leu Lys Glu Ser Phe Glu Arg Cys Leu Asp Leu Tyr Leu Cys Pro
            370                 375                 380

Arg Val Arg Lys Lys Arg Ile Asn Ile Asp Pro Glu Ser Leu Lys Pro
385                 390                 395                 400

Lys Leu Pro Ser Arg Lys Asp Leu Arg Pro Tyr Pro Asn Ser Cys Tyr
                405                 410                 415

Leu Glu Tyr Lys Gly His Thr Gly Ala Val Thr Ser Ile Ser Thr Asp
            420                 425                 430

Ser Ser Gly Glu Trp Ile Ala Ser Gly Ser Thr Asp Gly Ser Val Arg
            435                 440                 445

Met Trp Glu Val Glu Thr Gly Arg Cys Leu Lys Val Trp Gln Phe Asp
450                 455                 460

Glu Ala Ile Met Cys Val Ala Trp Asn Pro Leu Ser Arg Leu Pro Val
465                 470                 475                 480

Leu Ala Val Ala Met Gly Arg Asp Leu Phe Phe Leu Asn Thr Glu Leu
                485                 490                 495

Gly Thr Asp Glu Glu Gln Glu Ile Thr Lys Glu Arg Leu His Ser Gly
            500                 505                 510
```

```
Asn Ile Pro Glu Pro Asp Ala Ser Val Ala Ala Ile Val Thr Trp Leu
        515                 520                 525
Pro Asp Glu Leu Tyr Gly Gly Ile Lys Ile Arg His Phe Lys Ser Ile
    530                 535                 540
Ser Ser Ile Asp Trp His Arg Lys Gly Asp Tyr Leu Ser Thr Val Met
545                 550                 555                 560
Ala Ser Gly Glu Thr Arg Gly Val Val Leu His Gln Leu Ser Lys Gln
                565                 570                 575
Lys Thr Gln Arg Leu Pro Phe Lys Ile Arg Gly Leu Pro Val Cys Thr
            580                 585                 590
Leu Phe His Pro Ser Leu Ser Tyr Phe Val Ala Thr Arg Lys Asp
        595                 600                 605
Val Arg Val Tyr Asn Leu Leu Lys Pro Gly Glu Ala Thr Lys Lys Leu
    610                 615                 620
Glu Thr Gly Leu Arg Glu Ile Ser Ser Met Ala Ile His Pro Gly Gly
625                 630                 635                 640
Asp Asn Leu Ile Val Gly Ser Lys Glu Gly Lys Met Cys Trp Phe Asp
                645                 650                 655
Met Asp Leu Ser Ser Lys Pro Tyr Lys Thr Leu Lys Asn His Pro Lys
            660                 665                 670
Asp Ile Thr Asn Val Ala Val His Arg Ser Tyr Pro Leu Phe Ala Ser
        675                 680                 685
Cys Ser Glu Asp Ser Thr Ala Tyr Val Phe His Gly Met Val Tyr Asn
    690                 695                 700
Asp Leu Asn Gln Asn Pro Leu Ile Val Pro Leu Glu Ile Leu Arg Gly
705                 710                 715                 720
His Ser Ser Lys Gly Gly Val Leu Asp Cys Lys Phe His Pro Arg Gln
                725                 730                 735
Pro Trp Leu Phe Thr Ala Gly Ala Asp Ser Ile Ile Lys Leu Tyr Cys
            740                 745                 750
His

<210> SEQ ID NO 35
<211> LENGTH: 2205
<212> TYPE: DNA
<213> ORGANISM: Brassica napus

<400> SEQUENCE: 35
atgacgaaga ggagcaaagg agctaacgaa gaccaagtga agaacccaa gagaaaaatc      60
gtccctttaa atctcagaa agaagatgtg aaaagtttga agaggaaga gaccttctc      120
ttagactccg gcactgattc tgattacgac ggagatagct tgtcaggctc tttgaactcc    180
gatgacttcg actccgacat cttcgaatcc gaggacgacg atgattcaca tagagagacg    240
gaaggtgatt caggtcacga gggctcagat gaagtggtag atagtgagga tggcgaggag    300
gaagatggga gtgatgatga aggttctgag caacgtgaag tagccgaaga gagcgattca    360
tcagaagatg aggttgctcc aaggaacaca gttggggatg ttccattgga atggtacaaa    420
gacgagaaac atatcggtta tgacatcact ggtaaaaaga tcgccaagaa ggagaaacga    480
gacaagcttg actcttttct tgcaactatg gatgactcca gaactggcg caaagtttac    540
gatgagtata atgatgagga agtggagctg actaaagagg agagcaaact cattcgtaga    600
atgctcaaag gagaagctcc acatgctgac tttgatccat atgcgcctta tgttgactgg    660
ttcaaatggg acgatgcgat acatccgctc tcaagtgcac cagaacctaa gcggaggttc    720
atcccttcta aatgggaagc caaaaagttg ttaagttggt tagagcgagg aagggtatc    780
```

```
aagtttgata agcctgaaga agagcccaac gtataccttt tatggggtga cgattcagct      840
tcagatcaaa agagcaagca cttgacttat attcctccac cgaaactaaa attgccagga      900
cacgaggaat catacaatcc ttctctggaa tacattccaa cagaggaaga gaaagcagct      960
tatgaattga tgtatgagga agatcgtcca aaattcattc ctaaaaggtt cacatctctg     1020
agaagcatcc cagcatatga gaatgcacta aaggagtctt ttgatcgttg tttggatcta     1080
tacctgtgtc caagagttcg aaagaagaga ataaacatcg atcctgaatc tttgaagcct     1140
aagctaccta gtaggaagga tcttagacct tatccaaact catgttacct tgaatataaa     1200
ggccatacag gagctgttac ttccgtatcc cctgattgtt ctggccagtg gatagcctca     1260
ggtttccgcg atggatctgt tcgtatatgg gaagtgggag actggagatg ccttaaggtc     1320
tggcagtttg atgaagctgt taagtgtgtt gcctggaatc ctcttcctga cttttccaatt   1380 ctagcggtcg ccatgggagt agatttgttt ttcctgaaca ctgaacttgg cactgatgag     1440
gaacaacaaa ggattgaaga gctgcttcgc ttagataacc ttccagaact tgatgaagct     1500
gctgcagcaa ttgcaaagtg gcttctagat gagaaatatc gagggatcaa gataagacac     1560
ttcaagaacc tatcatatat tgactggcat ccaagaggag actacctctc agcagtcatg     1620
ccaggcgggg aaacgcgagg tgttgtaata caccagctct cagcacattc aacaaaaagg     1680
ctcccaataa agatgcgtgg acttccagtg tgcacacttt tcatcccaa tcaccgtggc      1740 ttattcatca tcgccactaa aaagtacgtt cgtgtttaca atcttcacaa gaacggggag     1800
cctataaaga agcctgagac agggctgaga gaaatctcat caatggcgat tcatcctggt     1860
ggtgataatc tggtagttgg aagcaaagaa gggaagatgt gttggtttga catggacctg     1920
tcttcggaac cgtacaagat tctcaagaat catcctaaag acattaccaa tgtgggttt      1980 caccgttcgt atccgttgtt tgcttcgtgc tcggaggatt caacagctta tgtgttccat     2040
ggaaaggttt atagtgatct taatgagaat cctctgattg tgccgttgga gattctaaga     2100
ggccactctt caaaaggagg agtcttggac tgcaagtttc atccaaggca gccatggcta     2160
ttcacggcag gtggtgactc aattatcaaa ctctattgcc actga                     2205
```

<210> SEQ ID NO 36
<211> LENGTH: 734
<212> TYPE: PRT
<213> ORGANISM: Brassica napus

<400> SEQUENCE: 36

```
Met Thr Lys Arg Ser Lys Gly Ala Asn Glu Asp Gln Val Lys Glu Pro
1               5                   10                  15

Lys Arg Lys Ile Val Pro Leu Lys Ser Gln Lys Glu Asp Val Lys Ser
            20                  25                  30

Leu Lys Glu Glu Asp Leu Leu Leu Asp Ser Gly Thr Asp Ser Asp
        35                  40                  45

Tyr Asp Gly Asp Ser Leu Ser Gly Ser Leu Asn Ser Asp Asp Phe Asp
    50                  55                  60

Ser Asp Ile Phe Glu Ser Glu Asp Asp Asp Ser His Arg Glu Thr
65                  70                  75                  80

Glu Gly Asp Ser Gly His Glu Gly Ser Asp Glu Val Val Asp Ser Glu
            85                  90                  95

Asp Gly Glu Glu Glu Asp Gly Ser Asp Glu Gly Ser Glu Gln Arg
        100                 105                 110

Glu Val Ala Glu Glu Ser Asp Ser Ser Glu Asp Glu Val Ala Pro Arg
    115                 120                 125
```

-continued

Asn Thr Val Gly Asp Val Pro Leu Glu Trp Tyr Lys Asp Glu Lys His
    130                 135                 140

Ile Gly Tyr Asp Ile Thr Gly Lys Lys Ile Ala Lys Lys Glu Lys Arg
145                 150                 155                 160

Asp Lys Leu Asp Ser Phe Leu Ala Thr Met Asp Ser Lys Asn Trp
                165                 170                 175

Arg Lys Val Tyr Asp Glu Tyr Asn Asp Glu Val Glu Leu Thr Lys
            180                 185                 190

Glu Glu Ser Lys Leu Ile Arg Arg Met Leu Lys Gly Glu Ala Pro His
        195                 200                 205

Ala Asp Phe Asp Pro Tyr Ala Pro Tyr Val Asp Trp Phe Lys Trp Asp
    210                 215                 220

Asp Ala Ile His Pro Leu Ser Ser Ala Pro Glu Pro Lys Arg Arg Phe
225                 230                 235                 240

Ile Pro Ser Lys Trp Glu Ala Lys Lys Leu Leu Ser Trp Leu Glu Arg
                245                 250                 255

Gly Arg Gly Ile Lys Phe Asp Lys Pro Glu Glu Glu Pro Asn Val Tyr
            260                 265                 270

Leu Leu Trp Gly Asp Asp Ser Ala Ser Asp Gln Lys Ser Lys His Leu
        275                 280                 285

Thr Tyr Ile Pro Pro Pro Lys Leu Lys Leu Pro Gly His Glu Glu Ser
    290                 295                 300

Tyr Asn Pro Ser Leu Glu Tyr Ile Pro Thr Glu Glu Glu Lys Ala Ala
305                 310                 315                 320

Tyr Glu Leu Met Tyr Glu Asp Arg Pro Lys Phe Ile Pro Lys Arg
                325                 330                 335

Phe Thr Ser Leu Arg Ser Ile Pro Ala Tyr Glu Asn Ala Leu Lys Glu
            340                 345                 350

Ser Phe Asp Arg Cys Leu Asp Leu Tyr Leu Cys Pro Arg Val Arg Lys
        355                 360                 365

Lys Arg Ile Asn Ile Asp Pro Glu Ser Leu Lys Pro Lys Leu Pro Ser
    370                 375                 380

Arg Lys Asp Leu Arg Pro Tyr Pro Asn Ser Cys Tyr Leu Glu Tyr Lys
385                 390                 395                 400

Gly His Thr Gly Ala Val Thr Ser Val Ser Pro Asp Cys Ser Gly Gln
                405                 410                 415

Trp Ile Ala Ser Gly Phe Arg Asp Gly Ser Val Arg Ile Trp Glu Val
            420                 425                 430

Gly Asp Trp Arg Cys Leu Lys Val Trp Gln Phe Asp Glu Ala Val Lys
        435                 440                 445

Cys Val Ala Trp Asn Pro Leu Pro Asp Phe Pro Ile Leu Ala Val Ala
    450                 455                 460

Met Gly Val Asp Leu Phe Phe Leu Asn Thr Glu Leu Gly Thr Asp Glu
465                 470                 475                 480

Glu Gln Gln Arg Ile Glu Glu Leu Leu Arg Leu Asp Asn Leu Pro Glu
                485                 490                 495

Leu Asp Glu Ala Ala Ala Ala Ile Ala Lys Trp Leu Leu Asp Glu Lys
            500                 505                 510

Tyr Arg Gly Ile Lys Ile Arg His Phe Lys Asn Leu Ser Tyr Ile Asp
        515                 520                 525

Trp His Pro Arg Gly Asp Tyr Leu Ser Ala Val Met Pro Gly Gly Glu
    530                 535                 540

Thr Arg Gly Val Val Ile His Gln Leu Ser Ala His Ser Thr Lys Arg

```
                       545                 550                 555                 560
Leu Pro Ile Lys Met Arg Gly Leu Pro Val Cys Thr Leu Phe His Pro
                   565                 570                 575
Asn His Arg Gly Leu Phe Ile Ile Ala Thr Lys Lys Tyr Val Arg Val
               580                 585                 590
Tyr Asn Leu His Lys Asn Gly Glu Pro Ile Lys Lys Pro Glu Thr Gly
           595                 600                 605
Leu Arg Glu Ile Ser Ser Met Ala Ile His Pro Gly Gly Asp Asn Leu
       610                 615                 620
Val Val Gly Ser Lys Glu Gly Lys Met Cys Trp Phe Asp Met Asp Leu
625                 630                 635                 640
Ser Ser Glu Pro Tyr Lys Ile Leu Lys Asn His Pro Lys Asp Ile Thr
               645                 650                 655
Asn Val Gly Phe His Arg Ser Tyr Pro Leu Phe Ala Ser Cys Ser Glu
           660                 665                 670
Asp Ser Thr Ala Tyr Val Phe His Gly Lys Val Tyr Ser Asp Leu Asn
       675                 680                 685
Glu Asn Pro Leu Ile Val Pro Leu Glu Ile Leu Arg Gly His Ser Ser
   690                 695                 700
Lys Gly Gly Val Leu Asp Cys Lys Phe His Pro Arg Gln Pro Trp Leu
705                 710                 715                 720
Phe Thr Ala Gly Gly Asp Ser Ile Ile Lys Leu Tyr Cys His
               725                 730

<210> SEQ ID NO 37
<211> LENGTH: 1449
<212> TYPE: DNA
<213> ORGANISM: Arabidopsis thaliana

<400> SEQUENCE: 37
atggttggat ctttggaatc tgatcaaact ctttcaatgg ccaccttaat cgaaaaactc      60
gacatcttat ctgacgactt cgatccaacc gccgtagtca ccgaaccgtt acctcctccg     120
gtaactaatg aatcggagc tgataaagga ggaggaggag agaaagaga gatggttctc      180 ggtaggaata tacacacaac gtcactcgct gtaacggaac cggaggttaa cgatgaattc     240
accggagata agaagcttta tggctagt gttcttgctc gttaccggaa aactttggtt      300
gaacgaacca aaaaccattt aggttatcct tataacttgg atttcgacta tggtgcgctt     360
ggtcagttac aacattttc gattaataat cttggagatc cgtttattga agtaactat      420 ggtgtacact caagaccttt tgaagttggt gtgttggatt ggtttgctcg tctttgggag     480
attgagagag atgattattg gggttacatt accaattgtg gtactgaagg caaccttcat     540
ggcattttag tcgggaggga gatgtttccg gatgggatat tgtatgcgtc gcgtgaatcg     600
cattactcgg tgtttaaagc tgctcgaatg tatcgaatgg agtgtgagaa ggttgatacg     660
cttatgtcag gggagattga ttgtgatgat ttgaggaaga agttgttggc taataaagat     720
aaaccggcga ttcttaatgt taacatagga cgacggttaa aaggagctgt tgatgatctt     780
gaccttgtta tcaaaactct tgaagagtgt ggtttctcac atgataggtt ctatattcat     840
tgtgatggag ctttgtttgg acttatgatg ccttttgtca acgtgcacc gaaagtgacg     900 tttaataaac cgataggag tgtgagtgta tcggccaca aatttgtcgg tgtgccaatg     960
ccatgtggtg ttcagataac aagaatggaa catatcaaag tcctctccag taacgttgag   1020
taccttgctt caagggatgc aacaatcatg ggaagtcgta acgggcatgc tcctttgttc   1080
ctctggtaca ccttaaacag gaaaggttac aaaggattcc agaaagaagt tcagaaatgc   1140
```

```
ttgagaaacg cgcattacct caaagaccga cttcgtgaag ctgggattag cgccatgctt    1200
aatgagctta gcagcactgt ggtctttgaa cggcctaaag atgaagagtt tgttagaagg    1260
tggcagcttg cttgccaagg tgatatagct catgtggtgg ttatgccaag tgttacaatc    1320
gagaagcttg ataatttcct gaaagacctt gtcaaacaca gattgatctg gtacgaggat    1380
ggatctcagc ctccttgcct tgcatcggag gtaggaacca acaactgcat ctgtccagct    1440
cacaagtga                                                            1449

<210> SEQ ID NO 38
<211> LENGTH: 482
<212> TYPE: PRT
<213> ORGANISM: Arabidopsis thaliana

<400> SEQUENCE: 38

Met Val Gly Ser Leu Glu Ser Asp Gln Thr Leu Ser Met Ala Thr Leu
1               5                   10                  15

Ile Glu Lys Leu Asp Ile Leu Ser Asp Asp Phe Asp Pro Thr Ala Val
            20                  25                  30

Val Thr Glu Pro Leu Pro Pro Val Thr Asn Gly Ile Gly Ala Asp
        35                  40                  45

Lys Gly Gly Gly Gly Glu Arg Glu Met Val Leu Gly Arg Asn Ile
    50                  55                  60

His Thr Thr Ser Leu Ala Val Thr Glu Pro Glu Val Asn Asp Glu Phe
65                  70                  75                  80

Thr Gly Asp Lys Glu Ala Tyr Met Ala Ser Val Leu Ala Arg Tyr Arg
                85                  90                  95

Lys Thr Leu Val Glu Arg Thr Lys Asn His Leu Gly Tyr Pro Tyr Asn
            100                 105                 110

Leu Asp Phe Asp Tyr Gly Ala Leu Gly Gln Leu Gln His Phe Ser Ile
        115                 120                 125

Asn Asn Leu Gly Asp Pro Phe Ile Glu Ser Asn Tyr Gly Val His Ser
    130                 135                 140

Arg Pro Phe Glu Val Gly Val Leu Asp Trp Phe Ala Arg Leu Trp Glu
145                 150                 155                 160

Ile Glu Arg Asp Asp Tyr Trp Gly Tyr Ile Thr Asn Cys Gly Thr Glu
                165                 170                 175

Gly Asn Leu His Gly Ile Leu Val Gly Arg Glu Met Phe Pro Asp Gly
            180                 185                 190

Ile Leu Tyr Ala Ser Arg Glu Ser His Tyr Ser Val Lys Ala Ala
        195                 200                 205

Arg Met Tyr Arg Met Glu Cys Glu Lys Val Asp Thr Leu Met Ser Gly
    210                 215                 220

Glu Ile Asp Cys Asp Asp Leu Arg Lys Leu Leu Ala Asn Lys Asp
225                 230                 235                 240

Lys Pro Ala Ile Leu Asn Val Asn Ile Gly Thr Thr Val Lys Gly Ala
                245                 250                 255

Val Asp Asp Leu Asp Leu Val Ile Lys Thr Leu Glu Glu Cys Gly Phe
            260                 265                 270

Ser His Asp Arg Phe Tyr Ile His Cys Asp Gly Ala Leu Phe Gly Leu
        275                 280                 285

Met Met Pro Phe Val Lys Arg Ala Pro Lys Val Thr Phe Asn Lys Pro
    290                 295                 300

Ile Gly Ser Val Ser Val Ser Gly His Lys Phe Val Gly Cys Pro Met
305                 310                 315                 320
```

Pro Cys Gly Val Gln Ile Thr Arg Met Glu His Ile Lys Val Leu Ser
            325                 330                 335

Ser Asn Val Glu Tyr Leu Ala Ser Arg Asp Ala Thr Ile Met Gly Ser
            340                 345                 350

Arg Asn Gly His Ala Pro Leu Phe Leu Trp Tyr Thr Leu Asn Arg Lys
            355                 360                 365

Gly Tyr Lys Gly Phe Gln Lys Glu Val Gln Lys Cys Leu Arg Asn Ala
        370                 375                 380

His Tyr Leu Lys Asp Arg Leu Arg Glu Ala Gly Ile Ser Ala Met Leu
385                 390                 395                 400

Asn Glu Leu Ser Ser Thr Val Val Phe Glu Arg Pro Lys Asp Glu Glu
                405                 410                 415

Phe Val Arg Arg Trp Gln Leu Ala Cys Gln Gly Asp Ile Ala His Val
            420                 425                 430

Val Val Met Pro Ser Val Thr Ile Glu Lys Leu Asp Asn Phe Leu Lys
            435                 440                 445

Asp Leu Val Lys His Arg Leu Ile Trp Tyr Glu Asp Gly Ser Gln Pro
        450                 455                 460

Pro Cys Leu Ala Ser Glu Val Gly Thr Asn Asn Cys Ile Cys Pro Ala
465                 470                 475                 480

His Lys

<210> SEQ ID NO 39
<211> LENGTH: 807
<212> TYPE: DNA
<213> ORGANISM: Arabidopsis thaliana

<400> SEQUENCE: 39
atggctgatg aaatcaatga gataagggaa gagcaagaac agctcgcacc ctttgatcct      60
tccaagaaga aaagaagaa gaaggttgtg attcaggaac tgtcgagga cttagcagag      120 tcttcacaga ctgagaaatc tgattcattg cctgttaatg atggtcttga gagttcattt      180
actggaatga agaaaaagaa gaagaagcca actgaatcaa gcttattgaa caacgaaagt      240
gttgatgctg gggaagattt ggatgagatt gctaatgacg agcaagaggg ggaagaagga      300
atagttctac agcaacgtta cccctgggag ggaagtgaga gggattacat atatgacgag      360
cttcttggta gagtctttaa cattctccgt gaaaataatc cggagcttgc tggagatagg      420
cgtcgtacag ttatgaggcc tcctcaagtt cttcgtgagg ggacaaagaa gactgtcttt      480
gtcaacttca tggacctttg caagacgatg catcgtcaac cagatcatgt tatgcaatac      540
ttgcttgctg agttgggtac tagtggttcg cttgatgggc agcaaggtt ggttgttaag      600 ggaaggtttg cacctaagaa ttttgaagga attttgcggc gatatatcac tgactacgtc      660
atttgccttg gttgcaagag cccagacacc attctctcca aggagaaccg tctcttcttt      720
ctgagatgtg aaagtgtgg atctcaacga tctgtggctc cgatcaaaac agggtttgtt      780
gctcgtgtta gtcgcaggaa gacttga                                         807

<210> SEQ ID NO 40
<211> LENGTH: 268
<212> TYPE: PRT
<213> ORGANISM: Arabidopsis thaliana

<400> SEQUENCE: 40

Met Ala Asp Glu Ile Asn Glu Ile Arg Glu Glu Gln Glu Gln Leu Ala
1               5                   10                  15

```
Pro Phe Asp Pro Ser Lys Lys Lys Lys Lys Lys Val Val Ile Gln
            20                  25                  30
Glu Pro Val Glu Asp Leu Ala Glu Ser Ser Gln Thr Glu Lys Ser Asp
        35                  40                  45
Ser Leu Pro Val Asn Asp Gly Leu Glu Ser Ser Phe Thr Gly Met Lys
 50                  55                  60
Lys Lys Lys Lys Lys Pro Thr Glu Ser Ser Leu Leu Asn Asn Glu Ser
 65                  70                  75                  80
Val Asp Ala Gly Glu Asp Leu Asp Glu Ile Ala Asn Asp Glu Gln Glu
                85                  90                  95
Gly Glu Glu Gly Ile Val Leu Gln Arg Tyr Pro Trp Glu Gly Ser
            100                 105                 110
Glu Arg Asp Tyr Ile Tyr Asp Glu Leu Leu Gly Arg Val Phe Asn Ile
        115                 120                 125
Leu Arg Glu Asn Asn Pro Glu Leu Ala Gly Asp Arg Arg Thr Val
130                 135                 140
Met Arg Pro Pro Gln Val Leu Arg Glu Gly Thr Lys Lys Thr Val Phe
145                 150                 155                 160
Val Asn Phe Met Asp Leu Cys Lys Thr Met His Arg Gln Pro Asp His
                165                 170                 175
Val Met Gln Tyr Leu Leu Ala Glu Leu Gly Thr Ser Gly Ser Leu Asp
            180                 185                 190
Gly Gln Gln Arg Leu Val Val Lys Gly Arg Phe Ala Pro Lys Asn Phe
        195                 200                 205
Glu Gly Ile Leu Arg Arg Tyr Ile Thr Asp Tyr Val Ile Cys Leu Gly
    210                 215                 220
Cys Lys Ser Pro Asp Thr Ile Leu Ser Lys Glu Asn Arg Leu Phe Phe
225                 230                 235                 240
Leu Arg Cys Glu Lys Cys Gly Ser Gln Arg Ser Val Ala Pro Ile Lys
                245                 250                 255
Thr Gly Phe Val Ala Arg Val Ser Arg Arg Lys Thr
            260                 265
```

<210> SEQ ID NO 41
<211> LENGTH: 819
<212> TYPE: DNA
<213> ORGANISM: Brassica napus

<400> SEQUENCE: 41

```
atggctgacg aaaacaatga gatgaaggag gtcaaggaca agcaagaact cgcacccttt    60
gatccaacca agaagaagaa gaagaagaaa gttgtcattc aagatcccat cgaggaacca   120
actgaggcac aagcggagac atctgattca ttgtctgcta atgatggcct tgatggccct   180
tcttttggaa ccaagaagaa aaagaagaag aagcctgttg aatcaagctt attgaatgaa   240
gaaagtgttg atgttccaga agatttggaa gagaatgcta atgacgagga gatgcagag   300
ggaatagatt tgcagcagca gcagcaacgt taccctggg agggaagtga cagggattac   360
atgtatgacg agcttcttgg tagagtcttt aacattctcc gtgagaacaa tccggagctt   420
gctggagata ggcgtcgtac agttatgagg cctcctcaag ttcttcgtga agggacaaag   480
aagacagtgt ttgtcaactt tatggacctc tgcaagacga tgcatcgtca accagatcat   540
gtgatgaatt tcttgcttgc tgagctggga accagtggtt cgcttgatgg gcagcaaaga   600
ttggttgtca aggaagatt tgcacccaag aattttgaag ggatattgcg tcgttatgtc   660
actgagtacg tcatttgcct tggttgcaag agcccggaca caattctctc aaaggagaat   720
```

```
cgtctcttct ttctcagatg cgaaaagtgt ggatctggaa gatcagtggc gcagatcaaa    780
gctggttttg ttgctcgtgt tggtcgcagg aagacttga                           819
```

<210> SEQ ID NO 42
<211> LENGTH: 272
<212> TYPE: PRT
<213> ORGANISM: Brassica napus

<400> SEQUENCE: 42

```
Met Ala Asp Glu Asn Asn Glu Met Lys Glu Val Lys Asp Lys Gln Glu
1               5                   10                  15

Leu Ala Pro Phe Asp Pro Thr Lys Lys Lys Lys Lys Lys Val Val
            20                  25                  30

Ile Gln Asp Pro Ile Glu Glu Pro Thr Glu Ala Gln Ala Glu Thr Ser
        35                  40                  45

Asp Ser Leu Ser Ala Asn Asp Gly Leu Asp Gly Pro Ser Phe Gly Thr
    50                  55                  60

Lys Lys Lys Lys Lys Lys Pro Val Glu Ser Ser Leu Leu Asn Glu
65                  70                  75                  80

Glu Ser Val Asp Val Pro Glu Asp Leu Glu Glu Asn Ala Asn Asp Glu
                85                  90                  95

Glu Asp Ala Glu Gly Ile Asp Leu Gln Gln Gln Gln Arg Tyr Pro
            100                 105                 110

Trp Glu Gly Ser Asp Arg Asp Tyr Met Tyr Asp Glu Leu Leu Gly Arg
        115                 120                 125

Val Phe Asn Ile Leu Arg Glu Asn Asn Pro Glu Leu Ala Gly Asp Arg
    130                 135                 140

Arg Arg Thr Val Met Arg Pro Pro Gln Val Leu Arg Glu Gly Thr Lys
145                 150                 155                 160

Lys Thr Val Phe Val Asn Phe Met Asp Leu Cys Lys Thr Met His Arg
                165                 170                 175

Gln Pro Asp His Val Met Asn Phe Leu Leu Ala Glu Leu Gly Thr Ser
            180                 185                 190

Gly Ser Leu Asp Gly Gln Gln Arg Leu Val Val Lys Gly Arg Phe Ala
        195                 200                 205

Pro Lys Asn Phe Glu Gly Ile Leu Arg Arg Tyr Val Thr Glu Tyr Val
    210                 215                 220

Ile Cys Leu Gly Cys Lys Ser Pro Asp Thr Ile Leu Ser Lys Glu Asn
225                 230                 235                 240

Arg Leu Phe Phe Leu Arg Cys Glu Lys Cys Gly Ser Gly Arg Ser Val
                245                 250                 255

Ala Gln Ile Lys Ala Gly Phe Val Ala Arg Val Gly Arg Lys Thr
            260                 265                 270
```

<210> SEQ ID NO 43
<211> LENGTH: 27
<212> TYPE: DNA
<213> ORGANISM: Artificial Sequence
<220> FEATURE:
<223> OTHER INFORMATION: Primer

<400> SEQUENCE: 43

```
gcggccgatg tctacctcgt cgcaatc                                        27
```

<210> SEQ ID NO 44
<211> LENGTH: 29
<212> TYPE: DNA
<213> ORGANISM: Artificial Sequence

```
<220> FEATURE:
<223> OTHER INFORMATION: Primer

<400> SEQUENCE: 44
cccgggtgag gatccaaagc gcccataat                              29

<210> SEQ ID NO 45
<211> LENGTH: 33
<212> TYPE: DNA
<213> ORGANISM: Artificial Sequence
<220> FEATURE:
<223> OTHER INFORMATION: Primer

<400> SEQUENCE: 45
gcggccgcgc catcttatac agttgttgac cta                         33

<210> SEQ ID NO 46
<211> LENGTH: 36
<212> TYPE: DNA
<213> ORGANISM: Artificial Sequence
<220> FEATURE:
<223> OTHER INFORMATION: Primer

<400> SEQUENCE: 46
cccgggcaca tattcggcca tttgatccca ctctcc                      36

<210> SEQ ID NO 47
<211> LENGTH: 32
<212> TYPE: DNA
<213> ORGANISM: Artificial Sequence
<220> FEATURE:
<223> OTHER INFORMATION: Primer

<400> SEQUENCE: 47
gcggccgcaa agagtactgg agtcctgctg ag                          32

<210> SEQ ID NO 48
<211> LENGTH: 31
<212> TYPE: DNA
<213> ORGANISM: Artificial Sequence
<220> FEATURE:
<223> OTHER INFORMATION: Primer

<400> SEQUENCE: 48
cccgggccag aaagggcacc acccaacata g                           31

<210> SEQ ID NO 49
<211> LENGTH: 34
<212> TYPE: DNA
<213> ORGANISM: Artificial Sequence
<220> FEATURE:
<223> OTHER INFORMATION: Primer

<400> SEQUENCE: 49
gcggccgcat gagtcatgtc aacattaaca catg                        34

<210> SEQ ID NO 50
<211> LENGTH: 35
<212> TYPE: DNA
<213> ORGANISM: Artificial Sequence
<220> FEATURE:
<223> OTHER INFORMATION: Primer

<400> SEQUENCE: 50
gcggccgcat gttggaatct gtttctcctg agttg                       35
```

```
<210> SEQ ID NO 51
<211> LENGTH: 30
<212> TYPE: DNA
<213> ORGANISM: Artificial Sequence
<220> FEATURE:
<223> OTHER INFORMATION: Primer

<400> SEQUENCE: 51
cccgggctca tttaaaactt cattagcatc                                    30

<210> SEQ ID NO 52
<211> LENGTH: 33
<212> TYPE: DNA
<213> ORGANISM: Artificial Sequence
<220> FEATURE:
<223> OTHER INFORMATION: Primer

<400> SEQUENCE: 52
gcggccgcat gtttggctcg agcaggtcaa cac                                33

<210> SEQ ID NO 53
<211> LENGTH: 29
<212> TYPE: DNA
<213> ORGANISM: Artificial Sequence
<220> FEATURE:
<223> OTHER INFORMATION: Primer

<400> SEQUENCE: 53 cccggggcc atttccaagc tcctaacta                                      29

<210> SEQ ID NO 54
<211> LENGTH: 30
<212> TYPE: DNA
<213> ORGANISM: Artificial Sequence
<220> FEATURE:
<223> OTHER INFORMATION: Primer

<400> SEQUENCE: 54
gcggccgcat ggatgccaac ccagttgctg                                    30

<210> SEQ ID NO 55
<211> LENGTH: 27
<212> TYPE: DNA
<213> ORGANISM: Artificial Sequence
<220> FEATURE:
<223> OTHER INFORMATION: Primer

<400> SEQUENCE: 55
cccgggaacc acctcttgag ccgcagc                                       27

<210> SEQ ID NO 56
<211> LENGTH: 31
<212> TYPE: DNA
<213> ORGANISM: Artificial Sequence
<220> FEATURE:
<223> OTHER INFORMATION: Primer

<400> SEQUENCE: 56
gcggccgcat gtcgcattac atttcaagag g                                  31

<210> SEQ ID NO 57
<211> LENGTH: 28
<212> TYPE: DNA
<213> ORGANISM: Artificial Sequence
<220> FEATURE:
<223> OTHER INFORMATION: Primer

<400> SEQUENCE: 57
```
cccgggacgg gggcatctgc acgatatg                                    28

<210> SEQ ID NO 58
<211> LENGTH: 34
<212> TYPE: DNA
<213> ORGANISM: Artificial Sequence
<220> FEATURE:
<223> OTHER INFORMATION: Primer

<400> SEQUENCE: 58
gcgatcgcaa gacgacgatg atgacgacgg tgat                              34

<210> SEQ ID NO 59
<211> LENGTH: 31
<212> TYPE: DNA
<213> ORGANISM: Artificial Sequence
<220> FEATURE:
<223> OTHER INFORMATION: Primer

<400> SEQUENCE: 59
gcggccgccg ctgcagggcc agtccagcca c                                 31

<210> SEQ ID NO 60
<211> LENGTH: 39
<212> TYPE: DNA
<213> ORGANISM: Artificial Sequence
<220> FEATURE:
<223> OTHER INFORMATION: Primer

<400> SEQUENCE: 60
gcgatcgcaa agcggccgca tgttacgtcc tgtagaaac                         39

<210> SEQ ID NO 61
<211> LENGTH: 29
<212> TYPE: DNA
<213> ORGANISM: Artificial Sequence
<220> FEATURE:
<223> OTHER INFORMATION: Primer

<400> SEQUENCE: 61
ggcgcgcctc attgtttgcc tccctgctg                                    29

<210> SEQ ID NO 62
<211> LENGTH: 26
<212> TYPE: DNA
<213> ORGANISM: Artificial Sequence
<220> FEATURE:
<223> OTHER INFORMATION: Primer

<400> SEQUENCE: 62
cccgggatga ccatgattac gtcaag                                       26

<210> SEQ ID NO 63
<211> LENGTH: 31
<212> TYPE: DNA
<213> ORGANISM: Artificial Sequence
<220> FEATURE:
<223> OTHER INFORMATION: Primer

<400> SEQUENCE: 63
ggcgcgcctt acttgtacag ctcgtccatg c                                 31

<210> SEQ ID NO 64
<211> LENGTH: 21
<212> TYPE: DNA
<213> ORGANISM: Artificial Sequence

```
<220> FEATURE:
<223> OTHER INFORMATION: Primer

<400> SEQUENCE: 64
cagtcctgaa actatctgcg g                                              21

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
tacggcacgc tcatttaaaa c                                              21

<210> SEQ ID NO 66
<211> LENGTH: 21
<212> TYPE: DNA
<213> ORGANISM: Artificial Sequence
<220> FEATURE:
<223> OTHER INFORMATION: Primer

<400> SEQUENCE: 66
aacccttaca tgacatgctc g                                              21

<210> SEQ ID NO 67
<211> LENGTH: 21
<212> TYPE: DNA
<213> ORGANISM: Artificial Sequence
<220> FEATURE:
<223> OTHER INFORMATION: Primer

<400> SEQUENCE: 67
aatcacctgc ataacacgct c                                              21

<210> SEQ ID NO 68
<211> LENGTH: 21
<212> TYPE: DNA
<213> ORGANISM: Artificial Sequence
<220> FEATURE:
<223> OTHER INFORMATION: Primer

<400> SEQUENCE: 68
ggctttgatg atctgctgaa c                                              21

<210> SEQ ID NO 69
<211> LENGTH: 21
<212> TYPE: DNA
<213> ORGANISM: Artificial Sequence
<220> FEATURE:
<223> OTHER INFORMATION: Primer

<400> SEQUENCE: 69
aacacggcac tacaaagttg g                                              21

<210> SEQ ID NO 70
<211> LENGTH: 21
<212> TYPE: DNA
<213> ORGANISM: Artificial Sequence
<220> FEATURE:
<223> OTHER INFORMATION: Primer

<400> SEQUENCE: 70
tgtaatcatt aaaccgctcg g                                              21
```

```
<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71
atcacatggt gaagttcctc g                                              21

<210> SEQ ID NO 72
<211> LENGTH: 21
<212> TYPE: DNA
<213> ORGANISM: Artificial Sequence
<220> FEATURE:
<223> OTHER INFORMATION: Primer

<400> SEQUENCE: 72
agaattcgca taagcgagtt g                                              21

<210> SEQ ID NO 73
<211> LENGTH: 21
<212> TYPE: DNA
<213> ORGANISM: Artificial Sequence
<220> FEATURE:
<223> OTHER INFORMATION: Primer

<400> SEQUENCE: 73
ctttaatgga tggagctgct g                                              21

<210> SEQ ID NO 74
<211> LENGTH: 21
<212> TYPE: DNA
<213> ORGANISM: Artificial Sequence
<220> FEATURE:
<223> OTHER INFORMATION: Primer

<400> SEQUENCE: 74
tgcacttgtt atctgcactg c                                              21

<210> SEQ ID NO 75
<211> LENGTH: 21
<212> TYPE: DNA
<213> ORGANISM: Artificial Sequence
<220> FEATURE:
<223> OTHER INFORMATION: Primer

<400> SEQUENCE: 75
tttctggcat cacacaattt g                                              21

<210> SEQ ID NO 76
<211> LENGTH: 21
<212> TYPE: DNA
<213> ORGANISM: Artificial Sequence
<220> FEATURE:
<223> OTHER INFORMATION: Primer

<400> SEQUENCE: 76
tgtccctgta gattgctcca c                                              21

<210> SEQ ID NO 77
<211> LENGTH: 21
<212> TYPE: DNA
<213> ORGANISM: Artificial Sequence
<220> FEATURE:
<223> OTHER INFORMATION: Primer

<400> SEQUENCE: 77
```

```
ggcagtcaaa ctatcagcct g                                              21

<210> SEQ ID NO 78
<211> LENGTH: 1473
<212> TYPE: DNA
<213> ORGANISM: Brassica napus

<400> SEQUENCE: 78
atggttggag ctctggaatc ggatcaatca ttcgcaatgg ctgaaaaatt cgacatcttg    60
tctgaaggtt tcgatccaac ggctgtggcc cccgaaccgt tacctttgcc ggtaacaaac   120
ggaaccggag cagatcaaga ggaagataat ctgaaaaaga cgaaggtggt gacaaacgga   180
ggaggagaaa gagagatggt tctgggcagg aatgtgcaca cgacttccct cgccgtgacg   240
gagccagagt ctaacgacga attcactgga gacaaagaag cttacatggc tagcgttctc   300
gctcgttacc ggaaaacttt ggtcgaacga accaaatatc atctaggtta ccatataaac   360
ttggatttcg actacggtgc gcttgggcag ttgcagcatt tctccatcaa caatcttgga   420
gatccgttta tcgaaagcaa ctatggtgta cactccaggc cttttgaagt tggcgtcttg   480
gattggtttg ctcgtctttg ggagatagag agagatgatt attggggtta catcacaaac   540
tgtggtaccg aaggaaacct tcacggcatt ttagttgggc gagaagtgtt tcccgatggg   600
attttgtatg cgtcgagtga atctcattac tctgtgttta aagcagctcg tatgtatcga   660
atggagtgtg agaaggttga tacgcttatc tcaggggaga ttgactgtga tgatttcaga   720
cggaagctgt tggcaaacaa agataaacca gccattctta atgttaacat aggaacaact   780
gttaaaggag ctgttgatga cctcgacctt gtgatcaaaa ctcttgaaga gtgtggcttc   840
tcacatgaca ggttctatat acactgtgat ggagctttgt ttggacttat gatgcctttt   900
gtcaaacggg caccaaaagt cacgttcaat aagccgatag ggagtgtgag cgtgtcgggc   960
cacaaatttg tcggatgccc aatgccatgt ggtgttcaga taacaagaat gaaacacatc  1020
aaagtcctct ctaacaacgt cgagtatctc gcttctaggg atgcaacaat catgggaagc  1080
cgaaacgggc atgctccttt gttcctctgg tacaccttaa acaggaaagg gtacaaagga  1140
ttccagaagg aggttcagaa atgcctgaga atgcgcatt  acctcaaaga ccgactccgt  1200
gaagctggga tcagcgcgat gctcaatgag cttagcagca ctgtggtctt tgaacgtccc  1260
aaggaggaag agtttgtcag aaggtggcag cttgcttgtc aaggcgatat agctcatgtg  1320
gtggttatgc caagtgttac agtagagaag ctggatcatt ttctcaagga cctggtcgaa  1380
cacagattgg tttggtatga ggacggatct caaccaccat gccttgtaaa agatgtaggg  1440
atcaacaact gcatctgtcc agctcacaag tga                               1473

<210> SEQ ID NO 79
<211> LENGTH: 490
<212> TYPE: PRT
<213> ORGANISM: Brassica napus

<400> SEQUENCE: 79

Met Val Gly Ala Leu Glu Ser Asp Gln Ser Phe Ala Met Ala Glu Lys
1               5                   10                  15

Phe Asp Ile Leu Ser Glu Gly Phe Asp Pro Thr Ala Val Ala Pro Glu
            20                  25                  30

Pro Leu Pro Leu Pro Val Thr Asn Gly Thr Gly Ala Asp Gln Glu Glu
        35                  40                  45

Asp Asn Leu Lys Lys Thr Lys Val Val Thr Asn Gly Gly Gly Glu Arg
    50                  55                  60
```

```
Glu Met Val Leu Gly Arg Asn Val His Thr Thr Ser Leu Ala Val Thr
65                  70                  75                  80

Glu Pro Glu Ser Asn Asp Glu Phe Thr Gly Asp Lys Glu Ala Tyr Met
                85                  90                  95

Ala Ser Val Leu Ala Arg Tyr Arg Lys Thr Leu Val Glu Arg Thr Lys
            100                 105                 110

Tyr His Leu Gly Tyr Pro Tyr Asn Leu Asp Phe Asp Tyr Gly Ala Leu
        115                 120                 125

Gly Gln Leu Gln His Phe Ser Ile Asn Asn Leu Gly Asp Pro Phe Ile
    130                 135                 140

Glu Ser Asn Tyr Gly Val His Ser Arg Pro Phe Glu Val Gly Val Leu
145                 150                 155                 160

Asp Trp Phe Ala Arg Leu Trp Glu Ile Glu Arg Asp Asp Tyr Trp Gly
                165                 170                 175

Tyr Ile Thr Asn Cys Gly Thr Glu Gly Asn Leu His Gly Ile Leu Val
            180                 185                 190

Gly Arg Glu Val Phe Pro Asp Gly Ile Leu Tyr Ala Ser Ser Glu Ser
        195                 200                 205

His Tyr Ser Val Phe Lys Ala Ala Arg Met Tyr Arg Met Glu Cys Glu
    210                 215                 220

Lys Val Asp Thr Leu Ile Ser Gly Glu Ile Asp Cys Asp Asp Phe Arg
225                 230                 235                 240

Arg Lys Leu Leu Ala Asn Lys Asp Lys Pro Ala Ile Leu Asn Val Asn
                245                 250                 255

Ile Gly Thr Thr Val Lys Gly Ala Val Asp Asp Leu Asp Leu Val Ile
            260                 265                 270

Lys Thr Leu Glu Glu Cys Gly Phe Ser His Asp Arg Phe Tyr Ile His
        275                 280                 285

Cys Asp Gly Ala Leu Phe Gly Leu Met Met Pro Phe Val Lys Arg Ala
    290                 295                 300

Pro Lys Val Thr Phe Asn Lys Pro Ile Gly Ser Val Ser Val Ser Gly
305                 310                 315                 320

His Lys Phe Val Gly Cys Pro Met Pro Cys Gly Val Gln Ile Thr Arg
                325                 330                 335

Met Lys His Ile Lys Val Leu Ser Asn Asn Val Glu Tyr Leu Ala Ser
            340                 345                 350

Arg Asp Ala Thr Ile Met Gly Ser Arg Asn Gly His Ala Pro Leu Phe
        355                 360                 365

Leu Trp Tyr Thr Leu Asn Arg Lys Gly Tyr Lys Gly Phe Gln Lys Glu
    370                 375                 380

Val Gln Lys Cys Leu Arg Asn Ala His Tyr Leu Lys Asp Arg Leu Arg
385                 390                 395                 400

Glu Ala Gly Ile Ser Ala Met Leu Asn Glu Leu Ser Ser Thr Val Val
                405                 410                 415

Phe Glu Arg Pro Lys Glu Glu Phe Val Arg Arg Trp Gln Leu Ala
            420                 425                 430

Cys Gln Gly Asp Ile Ala His Val Val Met Pro Ser Val Thr Val
        435                 440                 445

Glu Lys Leu Asp His Phe Leu Lys Asp Leu Val Glu His Arg Leu Val
    450                 455                 460

Trp Tyr Glu Asp Gly Ser Gln Pro Pro Cys Leu Val Lys Asp Val Gly
465                 470                 475                 480
```

-continued

```
Ile Asn Asn Cys Ile Cys Pro Ala His Lys
            485                 490
```